(12) United States Patent
Tawil et al.

(10) Patent No.: US 11,564,894 B2
(45) Date of Patent: Jan. 31, 2023

(54) COMPOSITION COMPRISING AMINO ACID POLYMERS AND A BIOACTIVE AGENT AND METHOD OF PREPARING THEREOF

(71) Applicant: PHAGELUX (CANADA) INC., Montreal (CA)

(72) Inventors: Nancy Tawil, Cantley (CA); Ramaz Katsarava, Tbilisi (GE); David Tugushi, Tbilisi (GE); Vakhtang Beridze, Tbilisi (GE)

(73) Assignee: PHAGELUX (CANADA) INC., Montreal (CA)

( * ) Notice: Subject to any disclaimer, the term of this patent is extended or adjusted under 35 U.S.C. 154(b) by 253 days.

(21) Appl. No.: 16/992,643

(22) Filed: Aug. 13, 2020

(65) Prior Publication Data

US 2020/0368176 A1    Nov. 26, 2020

Related U.S. Application Data

(63) Continuation-in-part of application No. 15/188,783, filed on Jun. 21, 2016, now Pat. No. 10,772,964.

(51) Int. Cl.
| | | |
|---|---|---|
| *A61K 9/70* | (2006.01) | |
| *A61K 33/38* | (2006.01) | |
| *A61K 35/76* | (2015.01) | |
| *A61K 47/02* | (2006.01) | |
| *A61K 9/00* | (2006.01) | |
| *A61K 9/14* | (2006.01) | |
| *A61K 31/635* | (2006.01) | |
| *A61K 31/785* | (2006.01) | |
| *A61K 47/34* | (2017.01) | |
| *A61L 26/00* | (2006.01) | |
| *A61P 17/00* | (2006.01) | |
| *C12N 7/00* | (2006.01) | |
| *A61K 45/06* | (2006.01) | |

(52) U.S. Cl.
CPC .......... *A61K 9/7069* (2013.01); *A61K 9/0014* (2013.01); *A61K 9/0024* (2013.01); *A61K 9/143* (2013.01); *A61K 9/7007* (2013.01); *A61K 31/635* (2013.01); *A61K 31/785* (2013.01); *A61K 33/38* (2013.01); *A61K 35/76* (2013.01); *A61K 47/02* (2013.01); *A61K 47/34* (2013.01); *A61L 26/0019* (2013.01); *A61L 26/0066* (2013.01); *A61P 17/00* (2018.01); *C12N 7/00* (2013.01); *A61K 45/06* (2013.01); *A61L 2300/104* (2013.01); *C12N 2795/00021* (2013.01); *C12N 2795/00032* (2013.01)

(58) Field of Classification Search
CPC .... A61K 9/7069; A61K 9/7007; A61K 33/38; A61K 35/76; A61K 47/02; A61K 45/06; A61K 9/0014; A61K 9/0024; A61K 9/143; A61K 31/635; A61K 31/785; A61K 47/34; A61L 2300/104; A61L 26/0019; A61L 26/0066; C12N 2795/00021; C12N 2795/00032; C12N 7/00; A61P 17/00

See application file for complete search history.

(56) References Cited

U.S. PATENT DOCUMENTS

| | | |
|---|---|---|
| 5,710,233 A | 1/1998 | Meckel et al. |
| 6,503,538 B1 | 1/2003 | Chu et al. |
| 6,703,040 B2 | 3/2004 | Katsarava et al. |
| 7,304,122 B2 | 12/2007 | Chu et al. |
| 7,408,018 B2 | 8/2008 | Chu et al. |
| 7,649,022 B2 | 1/2010 | Gomurashvili et al. |
| 7,794,706 B2 | 9/2010 | Carpenter et al. |
| 7,863,406 B2 | 1/2011 | Chu et al. |
| 8,445,627 B2 | 5/2013 | Katsarava et al. |
| 2002/0015720 A1* | 2/2002 | Katsarava ............. A61K 47/34 424/426 |
| 2006/0024357 A1 | 2/2006 | Carpenter et al. |
| 2006/0286064 A1 | 12/2006 | Turnell et al. |
| 2007/0106035 A1 | 5/2007 | Gomurashvili et al. |
| 2010/0040664 A1 | 2/2010 | Katsarava et al. |

FOREIGN PATENT DOCUMENTS

| | | |
|---|---|---|
| FR | 2344583 | 10/1977 |
| GE | P 2012 5618 B | 8/2012 |

OTHER PUBLICATIONS

Translation of Georgian Patent P 2012 5618 B, cited in "Foreign Patent Documents" section.
Partial European Search Report and provisional opinion dated Apr. 11, 2019 for European Patent application 16813797.4 corresponding to the present application.
Whole prosecution history of U.S. Appl. No. 15/188,783, filed Jun. 21, 2016, from which the present application is a CIP.

\* cited by examiner

*Primary Examiner* — Rabon A Sergent

(57) ABSTRACT

A method of treating, reducing or preventing bacterial infection in a wound, the method comprising: applying a film on the wound, the film including a biodegradable polymer with bacteriophages dispersed therein, wherein the polymer is a poly (ester amide urea).

27 Claims, 10 Drawing Sheets

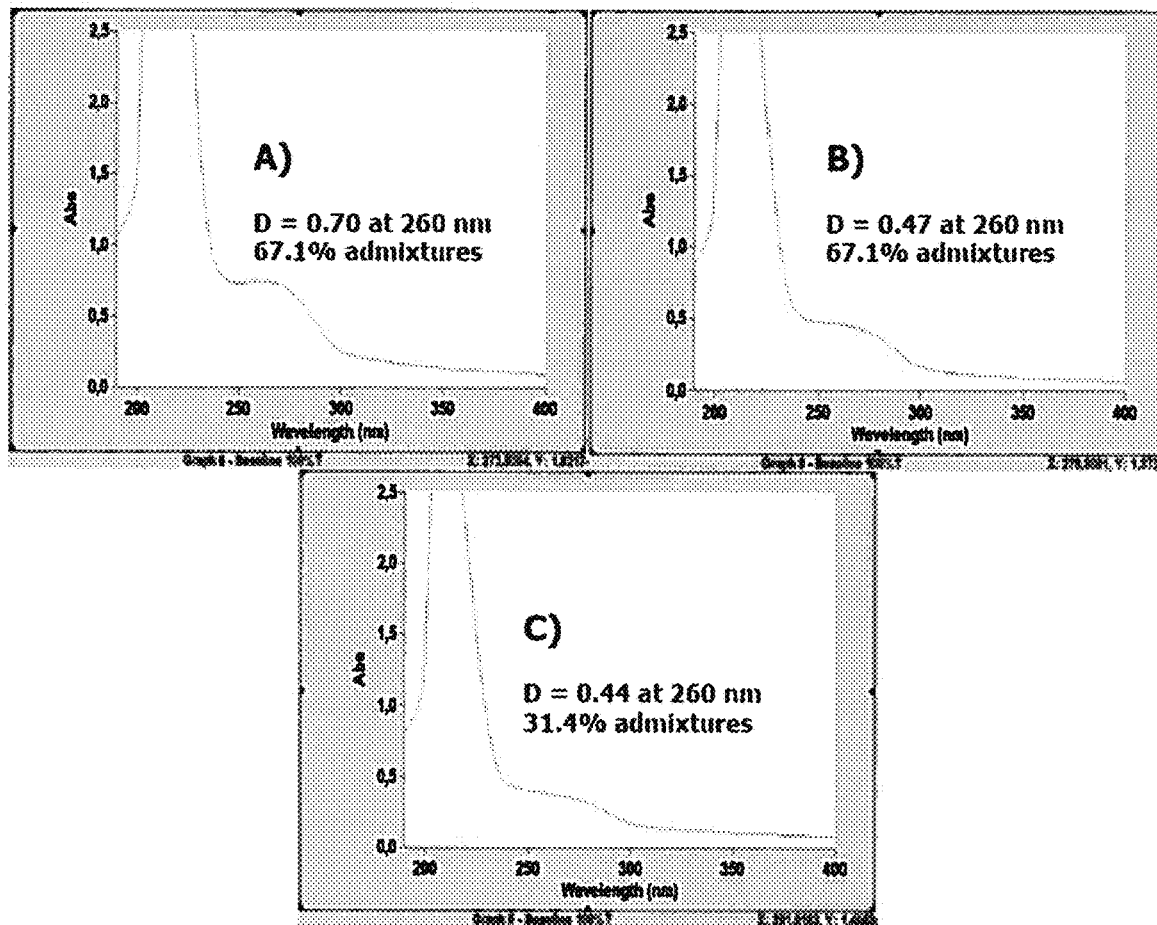
FIG. 1A. UV spectrum of Staphylophage (Serial preparation of Biochimpharm,LLC). Dilution 10x; admixtures are assumed to be 100%
FIG. 1B. UV spectrum of $MgCO_3$/Staphylophage,$F_0$ obtained after step 2. Dilution 10x; 67.1% of admixtures were removed after Step 2.
FIG. 1C. UV spectrum of MgCO3/Staphylophage,F1 obtained after step 3. Dilution 5x; 31.4% of admixtures were removed after Step 3.

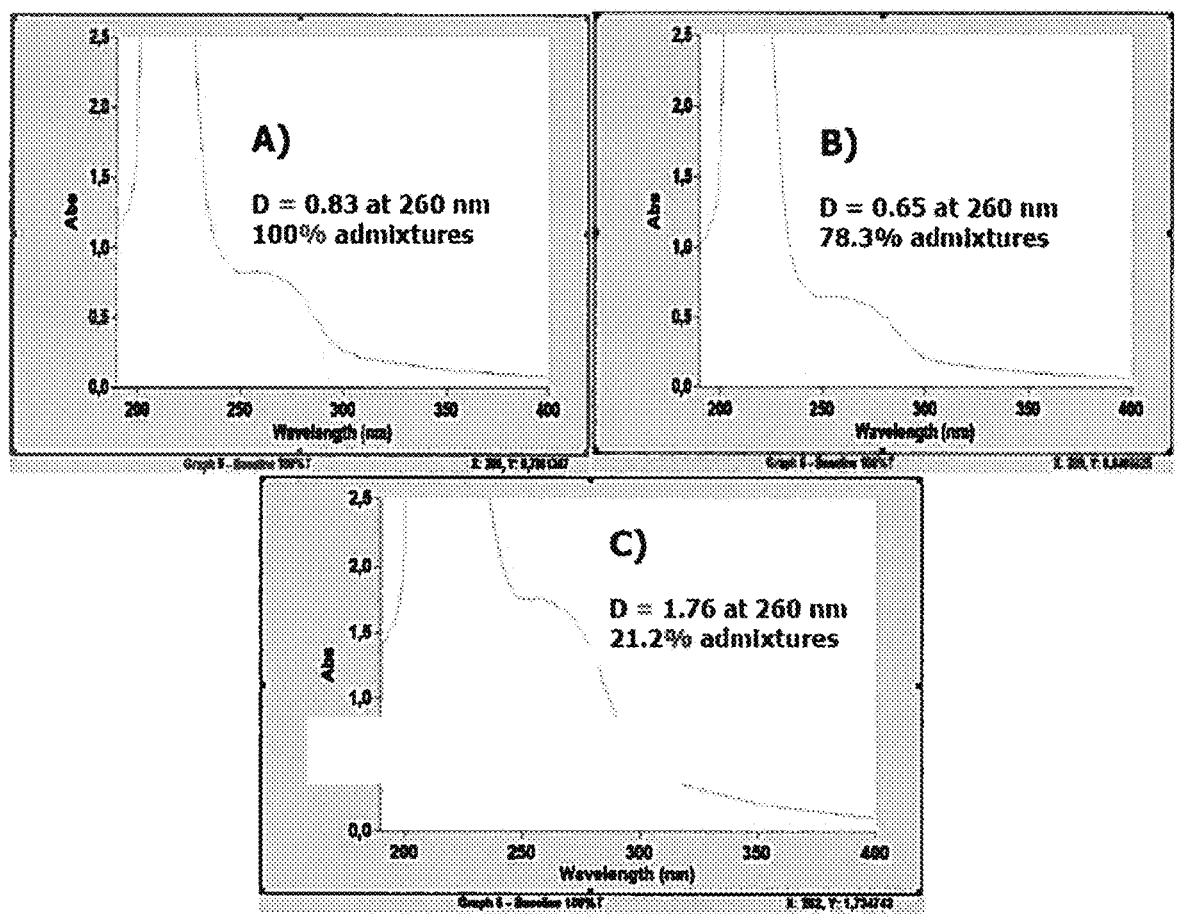
FIG. 2A. Staphylophage (Serial preparation of Biochimpharm,LLC). Dilution 10x; admixtures were assumed to be 100%.
FIG. 2B. $CaCO_3$/Staphylophage,$F_0$ obtained after step 2. Dilution 10x; 78.3% of admixtures were removed after Step 2.
FIG. 2C. CaCO3/Staphylophage,$F_1$ obtained after step 3. No Dilution; 21.2% of admixtures were removed after Step 3.

FIG. 3. Perforated polymeric film

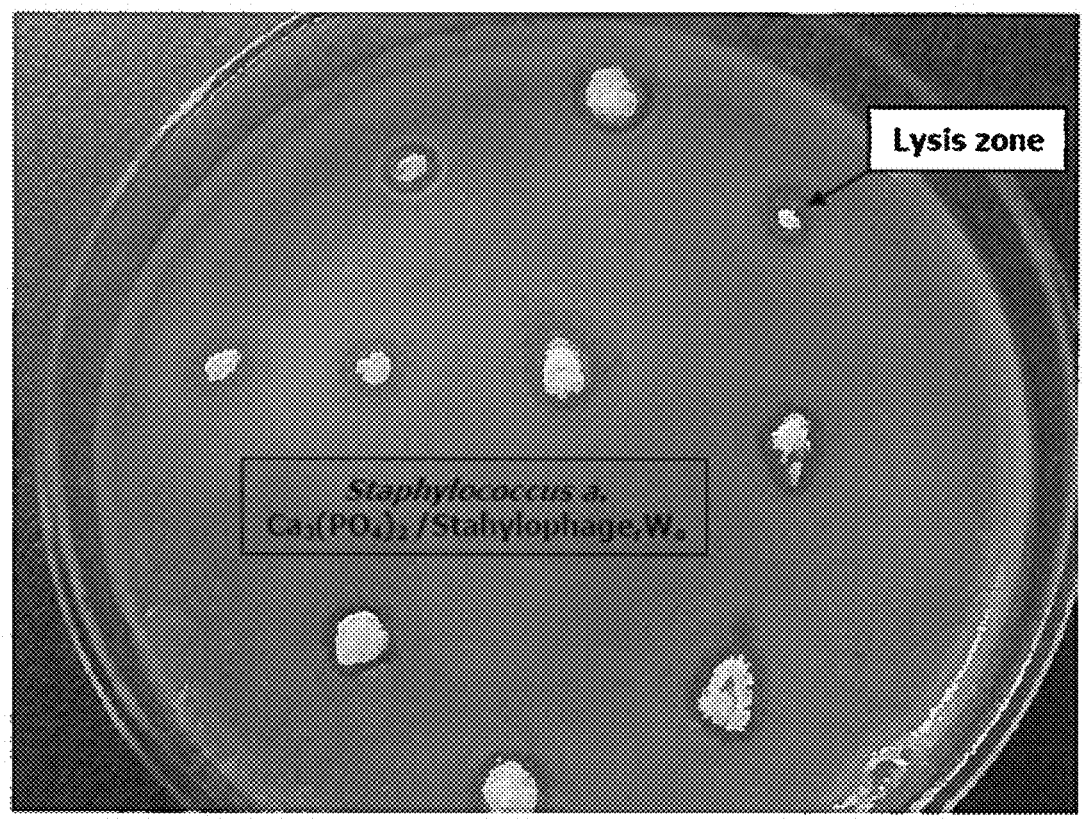
FIG. 4. Bactericidal activity of Staphylophage adsorbed on $Ca_3(PO_4)_2$, the $Ca_3(PO_4)_2$/Staphylophage, $W_0$ obtained after Step 1 and 2, on agar loan.

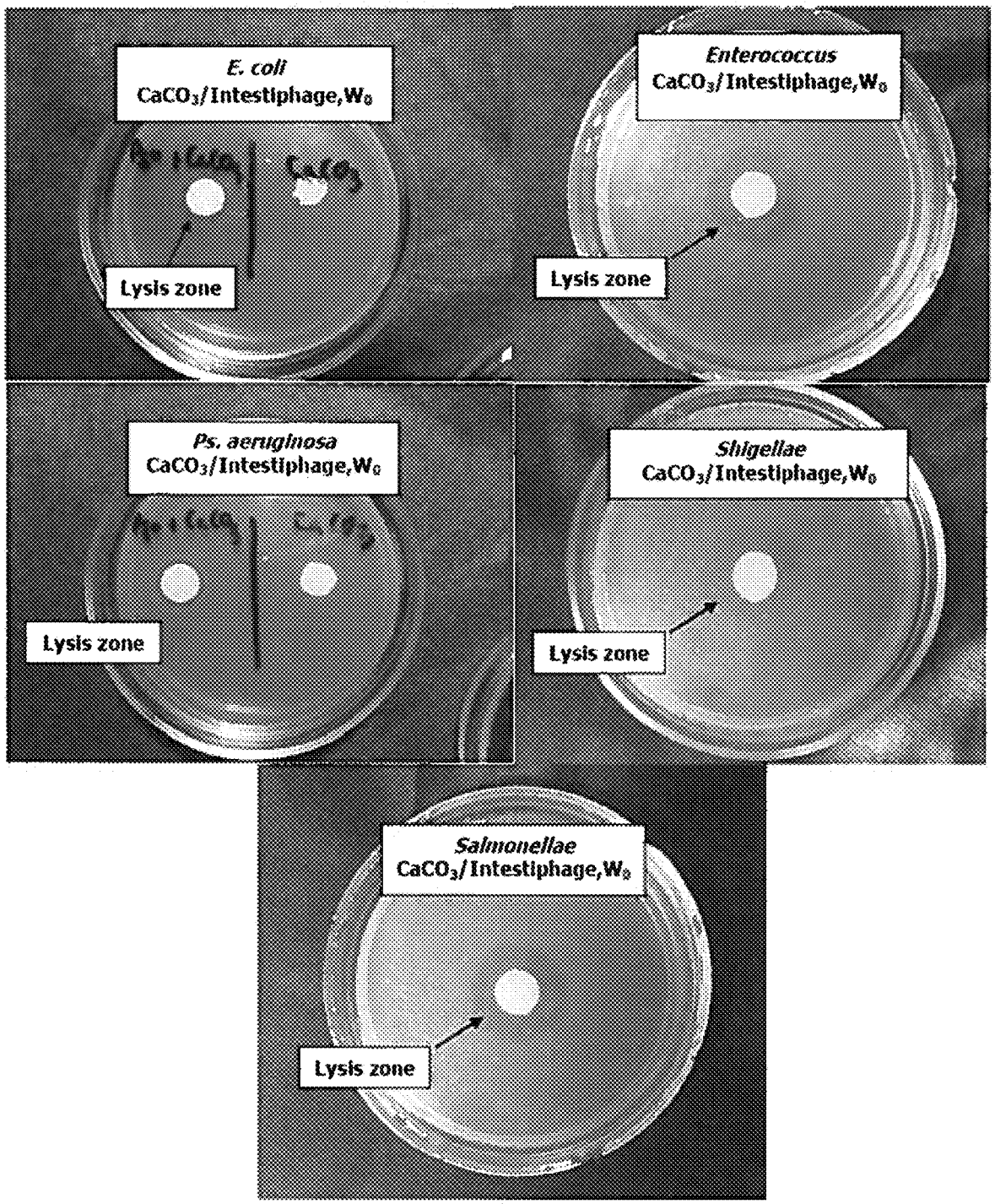
FIG. 5. Bactericidal activity of Intestiphage adsorbed on $CaCO_3$, the $CaCO_3$/Intestiphage, W0 obtained after Step 1 and 2, on agar loan.

COMPOSITION COMPRISING AMINO ACID POLYMERS AND A BIOACTIVE AGENT AND METHOD OF PREPARING THEREOF

FIELD OF THE INVENTION

The present invention relates to compositions comprising amino acid polymers and a bioactive agent and method of preparing thereof. Also, the present invention relates to the field of wound treatment, and is more particularly concerned with a method for treating a wound with a bacteriophages containing thin films.

BACKGROUND

Millions of people worldwide suffer abrasions and acute and chronic wounds each year. Wound dressings are designed with care so that their application will not infect or inflame a wound. Additionally, many wound dressings are designed to provide therapeutic benefits. For example, wound dressings comprising a polymer and bactericidal substances are commonly used in the treatment of superficial wounds. Additional wound dressings utilized for wound healing may further include at least one additional bioactive agent (e.g., pain relievers or bactericidal substances) released in a controlled manner as a result of diffusion, enzymatic degradation (e.g., proteolytic degradation), surface erosion, bulk erosion, or combinations thereof.

Many wound dressings comprising a polymer and at least one bioactive agent can result in positive clinical outcomes when used to treat superficial wounds. However, management of deep wounds in poorly vascularized tissues (e.g., trophic ulcers and bedsores) remains challenging for many patients. As used herein, "patient" refers to humans and other animals (e.g., mammals).

Deep wound infections are often difficult to treat and frequently become infected by multiple pathogenic organisms due to insufficient immune response in areas with minimal vasculature. Antibiotics may penetrate poorly into deep wounds, making eradication of infection extremely difficult.

While wound dressings comprising a polymer and at least one antibiotic may be used in the treatment of both superficial wounds and deep wounds, their efficacy may be increasingly limited by the development of antibiotic resistance at the wound site. Recently, there has been interest in using bactericidal substances such as silver sulfadiazine (and related diazine derivatives of sulfanilamide), furagin (and/or pharmaceutically acceptable salts thereof) and chlorhexidine (and/or pharmaceutically acceptable salts thereof) in addition to or in place of antibiotics in antibacterial wound dressings. However, utilization of such substances may be limited by their inherent toxicity, particularly in patients with underlying kidney or liver disease.

Bactericidal substances of natural origin, including highly specific viruses that can infect bacteria, referred to herein as bacteriophages, may present a promising alternative treatment. Bacteriophages are also referred to as "phages" herein. Bacteriophages have been reported to be effective in treating skin infections caused by *Pseudomonas* bacteria, *Staphylococcus* bacteria, *Klebsiella* bacteria, *Proteus* bacteria, *Escherichia coli*, and other pathogenic bacterial species. Bacteriophage tends to be highly specific for certain bacteria, so bacteriophage therapy may be targeted to kill specific pathogens without disturbing normal bacterial flora.

Polymers mixed with bacteriophage may be superior to liquid preparations of bacteriophage for the treatment of deep and chronic wounds due to the potential for controlled release of the bacteriophage. However, many currently available polymer-bacteriophage compositions comprise immobilized bacteriophage with reduced bactericidal activity or polymers that are not biodegradable, necessitating deliberate removal of the wound dressing. Thus, there remains a need in the art for polymers that can be prepared under mild conditions without using toxic catalysts and that can degrade by erosion into neutral byproducts, such as normal products of human metabolism. In some embodiments, the aforementioned polymers may be useful in the treatment of both superficial and deep wounds.

SUMMARY OF THE INVENTION

In a broad aspect, there is provided a method of treating, reducing or preventing bacterial infection in a wound, the method comprising: applying a flexible film on the wound, the film including a biodegradable polymer with bacteriophages dispersed therein, wherein the polymer is a poly(ester amide urea) comprising the following two blocks with random distribution thereof:

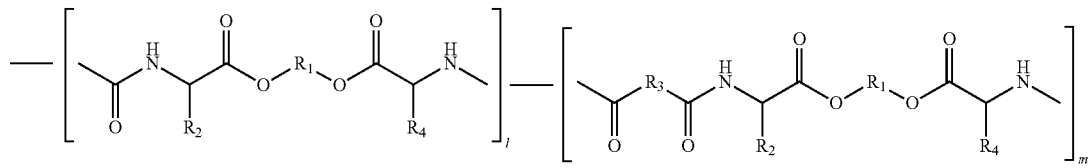

wherein
the ratio of l:m ranges from 0.01:0.99 to 0.99:0.01, l+m=1, $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

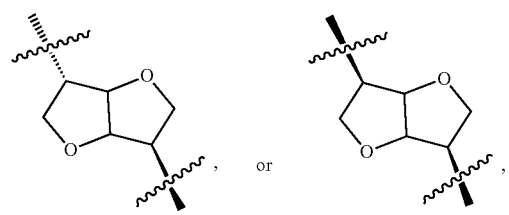

$R_3$ is $C_1$-$C_{12}$ alkylene,
$R_2$ and $R_4$ are independently chosen from the side chains of L- and D-amino acids so that the carbon to which $R_2$ or $R_4$ is attached has L or D chirality.

Typically, the film is a dry solid film.

There may also be provided a method wherein $R_1$ is —$(CH_2)_6$—, $R_3$ is —$(CH_2)_8$—, and both $R_2$ and $R_4$ are the side chain of L-leucine.

There may also be provided a method wherein the film further includes salt particles dispersed in the polymer.

There may also be provided a method wherein at least part of the bacteriophages is adsorbed on the salt particles.

There may also be provided a method wherein the salt particles include $CaCO_3$ particles.

There may also be provided a method wherein the film further includes a buffer.

There may also be provided a method wherein the buffer is TMN (Tris-$MgCl_2$—NaCl) buffer.

There may also be provided a method wherein the film further includes at least one of silversulfadiazine, silver nitrate and nanocrystalline silver.

There may also be provided a method wherein the film further includes an antibiotic.

There may also be provided a method wherein the film is applied for a duration of between 1 day and 20 days.

There may also be provided a method wherein the film is applied for a duration of between 3 and 7 days.

There may also be provided a method further comprising removing the film after the duration and applying another similar film on the wound.

There may also be provided a method further comprising delivering a predetermined fraction of the bacteriophages in the wound within a predetermined rapid delivery period immediately after applying the film, the predetermined rapid delivery period being smaller than 4 hours, and afterwards releasing at least part of the remaining bacteriophages in the wound at a rate smaller than within the predetermined rapid delivery period.

There may also be provided a method further comprising gradually delivering at least part of the bacteriophages in the wound at a controlled delivery rate, the controlled delivery rate being controlled by a volume and composition of a wound exudate produced by the wound while the film is applied.

There may also be provided a method wherein the controlled delivery rate increases for an increase is volumic production rate of the wound exudate.

There may also be provided a method wherein the controlled delivery rate increases with an increase in elastase and metalloproteinases quantity present in the wound exudate as a result of cell lysis within the wound.

There may also be provided a method wherein the film includes an enzyme operative to degrade the film.

There may also be provided a method wherein the enzyme is selected from elastase and a metalloproteinase.

There may also be provided a method wherein the bacteriophages are present in the film at 500,000 PFU/cm^2 or more.

There may also be provided a method wherein the film is non-woven and non-porous.

There may also be provided a method wherein the film is between 100 μm and 1000 μm thick.

There may also be provided a method wherein the wound is a pressure ulcer.

There may also be provided a method wherein the wound is a burn wound.

There may also be provided a method wherein a bactericide is applied to the wound before the film is applied.

There may also be provided a method wherein the bactericide includes at least one of an antibiotic, silversulfadiazine, silver nitrate and nanocrystalline silver.

There may also be provided a method wherein the wound contains at least one of antibiotic-resistant and silver-resistant bacteria, the bacteriophages being specific for the at least one of antibiotic-resistant and silver-resistant bacteria.

There may also be provided a method wherein the film is substantially transparent when wet.

In another broad aspect, there is provided a method of treating, reducing or preventing bacterial infection in a wound, the method comprising: applying a film on the wound, the film including bacteriophages dispersed in a biodegradable polymer, wherein the polymer is selected from (1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond, (4) a poly (ester amide urethane) wherein at least one diol, at least one diacid, and at least one amino acid are linked together through an ester bond, an amide bond, and a urethane bond, (5) a poly (ester urea) wherein at least one diol and at least one amino acid are linked together through an ester bond and a urea bond, and (6) a poly (ester urethane) wherein at least one diol and at least one amino acid are linked together through an ester bond and a urethane bond, further wherein the at least one diol is a compound of formula:

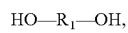

$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

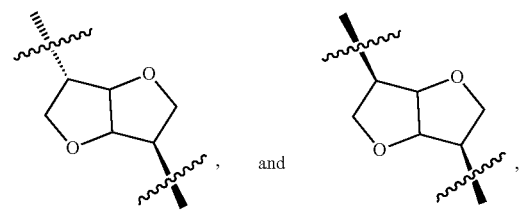

the at least one diacid is a compound of formula:

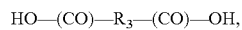

$R_3$ is $C_1$-$C_{12}$ alkylene,
the at least one amino acid is chosen from a naturally occurring amino acid and non-naturally occurring amino acid.

The various additional features mentioned in the first method provided above also apply to the present method.

Advantageously, in some embodiments, the proposed film produces or eliminates toxic organic by-products during the manufacturing process, for example by using triphosgene as one of the base reactants, which also advantageously provides a bacteriophage friendly environment.

BRIEF DESCRIPTION OF THE DRAWINGS

FIG. 1A-C depicts the UV spectra of Staphylophage, $MgCO_3$/Staphylophage,$F_0$ obtained after step 2 (Example 4), and $MgCO_3$/Staphylophage,F1 obtained after step 3 (Example 4), respectively.

FIG. 2A-C depicts the UV spectra of Staphylophage, CaCO$_3$/Staphylophage, F$_0$ obtained after step 2 (Example 4), and CaCO$_3$/Staphylophage, F1 obtained after step 3 (Example 4), respectively.

FIG. 3 depicts the appearance of an exemplary perforated polymeric film.

FIG. 4 shows a representative example of the antibacterial activity of Staphylophage adsorbed on CaCO$_3$, the wet solid after Step 1 and 2 (Example 4), in a double agar overlay assay.

FIG. 5 shows representative examples of the antibacterial activity of Intestiphage adsorbed on CaCO$_3$, the wet solid after Step 1 and 2 (Example 4), in a double agar overlay assay.

DETAILED DESCRIPTION

Figure 6A:
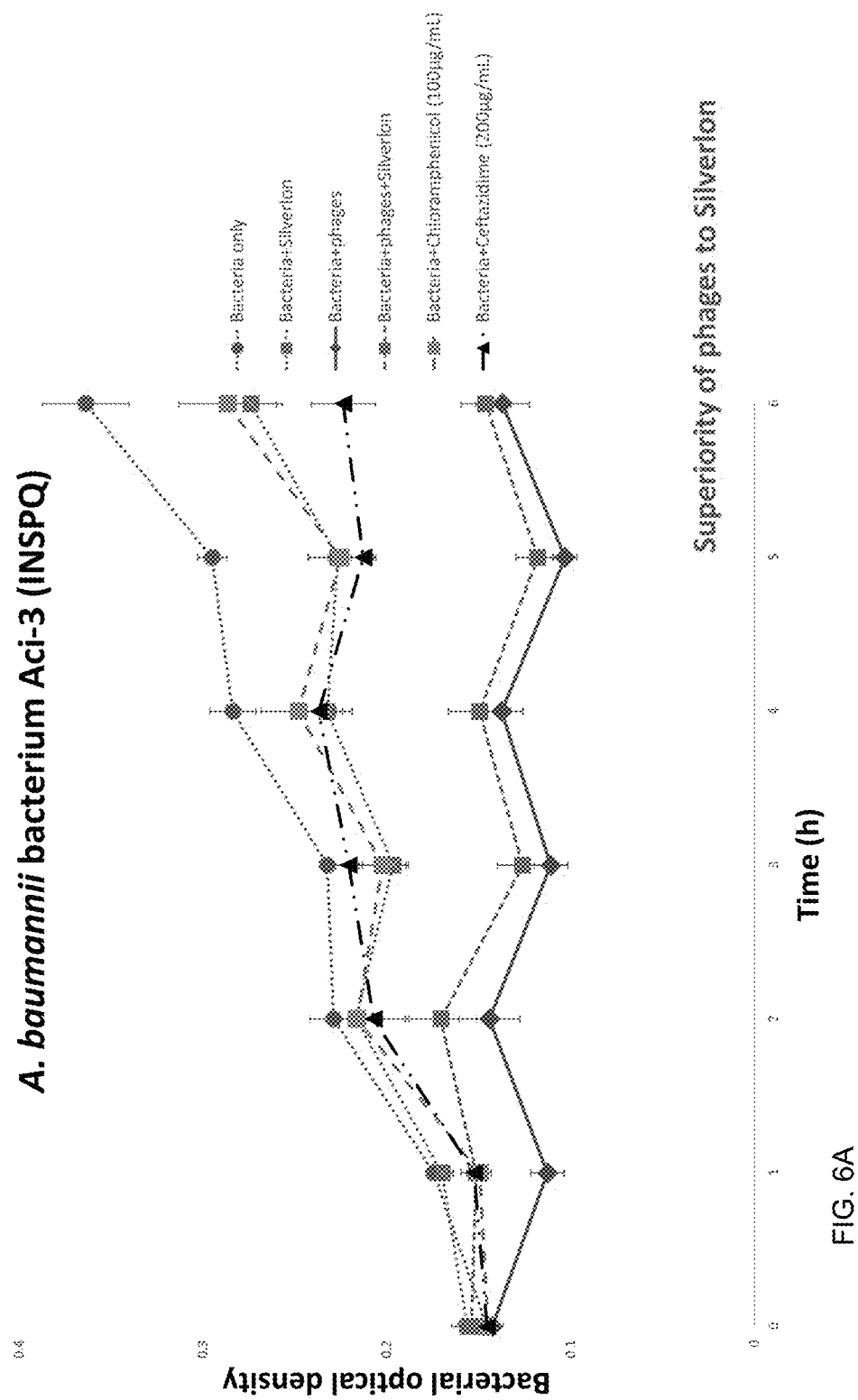
FIG. 6A-D compares the effect on bacterial growth of bacteriophages and Silverlon™ taken alone or in combination on 4 bacterial strains.

Disclosed herein are: (1) a polymer that can be biodegradable; (2) a composition comprising the polymer, a bioactive agent, and optionally a filler; and (3) methods of preparation thereof. Also disclosed herein is a composition in a powdery form comprising a bacteriophage.

Definitions and Abbreviations

A dash ("-") that is not between two letters or symbols is used to indicate a point of attachment for a substituent. For example, —(CH$_2$)$_6$— is attached on each end through a carbon atom.

Unless clearly indicated otherwise, use of the terms "a," "an," and the like refers to one or more.

The term "alkylene" herein refers to a bivalent hydrocarbon group selected from linear and branched saturated hydrocarbon groups comprising, for example, from 1 to 18 carbon atoms, such as from 1 to 12, further such as from 1 to 10, even further such as from 1 to 6, carbon atoms. Non-limiting examples of alkylene include —CH$_2$—, —(CH$_2$)$_2$—, —(CH$_2$)$_6$—, and —(CH$_2$)$_8$—. When "alkylene" is interrupted by at least one oxygen, it means that at least one pair of neighboring carbons in an alkylene is separated by one oxygen, such as in the ether groups —CH$_2$—O—CH$_2$—, —CH$_2$—CH$_2$—O—CH$_2$—CH$_2$—, and —CH$_2$—O—CH$_2$—CH$_2$—O—CH$_2$—CH$_2$—.

The term "cycloalkylene" herein refers to a bivalent hydrocarbon group selected from saturated cyclic hydrocarbon groups, comprising monocyclic and polycyclic (e.g., bicyclic and tricyclic) groups, wherein the two points of attachment are on the cyclic ring. For example, the cycloalkyl group may comprise from 3 to 12 carbon atoms, such as from 3 to 8, further such as from 3 to 6, from 3 to 5, or from 3 to 4, carbon atoms. Non-limiting examples of cycloalkylene include

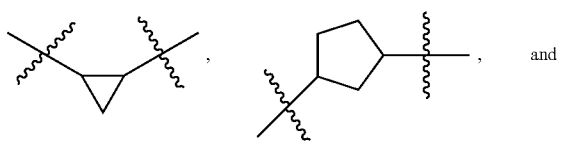

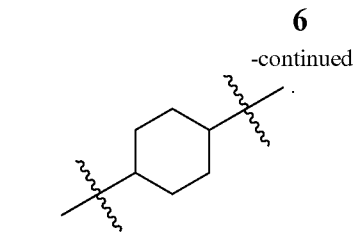

The term "cycloalkylalkylene" herein refers to a bivalent hydrocarbon group wherein a saturated cyclic hydrocarbon group, chosen from monocyclic and polycyclic (e.g., bicyclic and tricyclic) groups, is substituted by at least one hydrocarbon group chosen from linear and branched saturated hydrocarbon group comprising, for example, from 1 to 18 carbon atoms, and wherein at least one of the two points of attachment is on the at least one hydrocarbon group chosen from linear and branched saturated hydrocarbon groups. Non-limiting examples of cycloalkylalkylene include

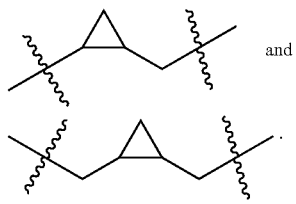

As used herein, the terms "L-amino acid" and "D-amino acid" (or D-enantiomer) refers to amino acid stereoisomers. All known naturally occurring amino acids except for glycine, which adopts a single conformation, can exist in two isomeric states. L-amino acids and D-amino acids are analogous to left-handed and right-handed enantiomers. L-amino acids are primarily utilized in mammalian cells to produce proteins.

As used herein, a "patient" refers to a human or other animal, for example a mammal. In some embodiments, the patient is a mammal, and in other specific embodiments, the patient is human.

As used herein, a compound that is "poorly soluble" in a solvent is a compound that is "slightly soluble," "very slightly soluble," or "practically insoluble" in the solvent according to the definitions provided in the United States Pharmacopeia (USP). The USP classifications for solubility are listed in Supplemental Table 1 below.

SUPPLEMENTAL TABLE 1

USP Definitions of Solubility

| Description form (Solubility definition) | Parts of solvent required for one part of solute | Solubility range (mg/mL) | Solubility assigned (mg/mL) |
|---|---|---|---|
| Very soluble (VS) | <1 | >1,000 | 1,000 |
| Freely soluble (FS) | from 1 to 10 | 100-1,000 | 100 |
| Soluble | from 10 to 30 | 33-100 | 33 |
| Sparingly soluble (SPS) | from 30 to 100 | 10-33 | 10 |
| Slightly soluble (SS) | from 100 to 1,000 | 1-10 | 1 |
| Very slightly soluble (VSS) | from 1,000 to 10,000 | 0.1-1 | 0.1 |
| Practically insoluble (PI) | >10,000 | <0.1 | 0.01 |

As used herein, a "polymer blend" is a mixture comprising at least two polymers, wherein the two polymers are not the same.

Polymers and Polymer Blends

In some embodiments, the disclosure provides an amino acid based polymer that can be biodegradable.

Amino acid based polymers that can be biodegradable are suitable for preparing a composition further comprising at least one bioactive agent, such as bacteriophage. For example, in some embodiments, bacteriophage is dispersed, mixed, dissolved, homogenized, or covalently bonded in a composition further comprising an amino acid based polymer.

The amino acid based polymers can be solubilized in chloroform, an organic solvent which may not inactivate the at least one bioactive agent such as bacteriophage during the preparation of the composition.

In some embodiments, the polymer can be solubilized in an organic solvent. For example, in some embodiments, the polymer can be solubilized in chloroform, dichloromethane, or ethyl acetate.

Other biodegradable polymers, including commercially available poly(lactide/glycolide) copolymers, are also soluble in chloroform. However, these biodegradable polymers can be used but are less suitable for preparing a composition further comprising at least one bioactive agent, such as the at least one bioactive agent disclosed herein, since they may have some limitations compared to amino acid based biodegradable polymers, which are listed in Table 1 below:

TABLE 1

Amino acid based biodegradable polymers vs. poly(lactide/glycolide) copolymers

| Amino acid based biodegradable polymers (Properties achieved in some embodiments) | Poly(lactide/glycolide) copolymers (General properties) |
|---|---|
| Polycondensation synthesis without using any toxic catalyst | Ring-opening polymerization using toxic metalorganic catalysts |
| Synthesis under normal atmospheric conditions at room temperature | Synthesis via ring-opening polymerization under extra-dry conditions at 195-230° C. |
| Higher hydrophilicity and, hence, better compatibility with tissues | Hydrophobic polymers, relatively poor compatibility with tissues |
| Longer shelf-life | Thermodynamically unstable polymers, depolymerize on storage |
| A wide range of material properties including elasticity desirable for wound dressings | Narrow range of desirable material properties, poor elasticity |
| A high range of biodegradation rates that can be regulated by impregnating enzymes | A narrow range of biodegradation rates, poor possibility to regulate them by impregnating enzymes |
| A variable hydrophobicity/hydrophilicity balance suitable for constructing a drug sustained/controlled release devices | Low variability of hydrophobicity/hydrophilicity balance suitable for constructing a drug sustained/controlled release devices |
| High nutritious properties owing to release of α-amino acids upon biodegradation | Poor nutritious properties (no amino acid released upon biodegradation) |
| Lower acidic or neutral medium after ultimate biodegradation* | Higher acidic medium after ultimate biodegradation[1] |

Notes on the * in the table: After ultimate biodegradation of poly(glycolic acid), poly(lactic acid)s, or poly(lactic-co-glycolic acid), glycolic and lactic acids are released that have $pK_a$ 3.83 and 3.86, accordingly. After ultimate biodegradation of poly(ester amide)s, e.g. on the basis of sebacic acid, neutral α-amino acids (zwitterionic compounds) and fatty diols along with sebacic acid are released; the latter has $pK_{a1}$ 4.72 and $pK_{a2}$ 5.45 that is by approximately one unit of $pK_a$ lower when compared to glycolic and lactic acids. After ultimate biodegradation of amino acid based poly(ester urea)s, the medium should be close to physiological since normal products of metabolism-carbon dioxide and α-amino acids along with neutral fatty diols are released. The preparation of poly(ester amide)s is described in R. Katsarava, V. Beridze, N. Arabuli, D. Kharadze, C. C. Chu, C. Y. Won. Amino acid based bioanalogous polymers. Synthesis and study of regular poly(ester amide)s based on bis(α-amino acid) α,ω-alkylene diesters and aliphatic dicarboxylic acids. *J. Polym. Sci.: Part A: Polym. Chem.* 37, 391-407 (1999)

In addition, biodegradation of poly(glycolic acid) and poly(lactic acid)s may lead to the production of much higher quantities of acidic products per unit weight of the polymers are released compared to poly(ester amide)s. For example:

after biodegradation of 1.0 g of poly(glycolic acid), 1.31 g (0.017 mole) of glycolic acid is released, after biodegradation of 1.0 g of poly(lactic acid), 1.25 g (0.014 mole) of lactic acid is released, after biodegradation of 1.0 g of poly(ester amide) composed of phenylalanine, sebacic acid and 1,6-hexanediol, only 0.35 g (0.0017 mole) of sebacic acid is released, and after biodegradation of 1.0 g of co-poly(ester urea amide), which can be useful, for example, for preparing bacteriophage containing composition, a negligible quantity—0.09 g (0.00044 mole) of sebacic acid is released.

after biodegradation of co-poly(ester urea urethane), normal products of metabolism—carbon dioxide and α-amino acids along with neutral fatty diols are released (i.e., no acidic component is released).

A highly acidic medium may be harmful to some bioactive agents such as bacteriophage. Therefore, poly(lactide/glycolide) polyesters may be less promising than amino acid based polymers that can be bio-degradable for preparing a composition further comprising at least one bioactive agent such as bacteriophage.

In addition, polymers provided herein may be synthesized using organic solvents that are compatible with bacteriophage. For example, polymers provided herein may be synthesized using organic solvents such as chloroform, dichloromethane, and ethyl acetate as opposed to dimethylformamide (DMF), dimethylacetamide (DMA), and dimethylsulfoxide (DMSO). The organic solvents DMF, DMA, and DMSO, which have previously been used in the synthesis of bio-degradable amino acid based polymers, are not compatible with bacteriophage, rendering polymers produced using these solvents less suitable for the preparation of compositions comprising bacteriophage.

In addition, in some embodiments, polymers provided herein do not comprise L-phenylalanine, an amino acid found in some previous polymeric blends used for the preparation of compositions further comprising at least one bioactive agent. The presence of L-phenylalanine in a polymer may led to adverse events in patients suffering from phenylketonuria.

Exemplary amino acids used to produce polymers described herein include, but are not limited to, L-glycine, L-alanine, L-valine, L-leucine, L-isoleucine, L-proline, L-methionine, L-phenylalanine, L-tryptophan, and D isomers thereof.

Provided herein is a polymer chosen from (1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond, (3) a poly (ester amide urethane urea) wherein at least one diol, at least one diacid, and at least one amino acid are linked together through an ester bond, an amide bond, a urethane bond, and a urea bond, (4) a poly (ester amide urethane) wherein at least one diol, at least one diacid, and at least one amino acid are linked together through an ester bond, an amide bond, and a urethane bond, (5) a poly (ester urea) wherein at least one diol and at least one amino acid are linked together through an ester bond and a urea bond (in other words, at least one diol, a carbonic acid, and at least one amino acid are linked together through an ester bond and a urea bond), and (6) a poly (ester urethane) wherein at least one diol and at least one amino acid are linked together through an ester bond and a urethane bond, further wherein the at least one diol is a compound of formula HO—R$_1$—OH, wherein R$_1$ is chosen from an alkylene optionally interrupted by at least one oxygen, a cycloalkylene, a cycloalkylalkylene,

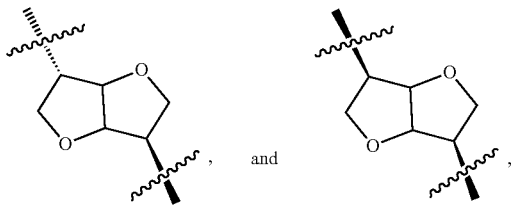

the at least one diacid is a compound of formula HO—(CO)—R$_3$—(CO)—OH, wherein R$_3$ is an alkylene, and the at least one amino acid is chosen from a naturally occurring amino acid or a non-naturally occurring amino acid.

Further provided herein is a polymer chosen from (1) a poly (ester amide urea) wherein at least one diol, at least one diacid, and at least one amino acid are linked together through an ester bond, an amide bond, and a urea bond;

(2) a poly (ester urethane urea) wherein at least one diol and at least one amino acid are linked together through an ester bond, a urethane bond, and a urea bond;

(3) a poly (ester amide urethane urea) wherein at least one diol, at least one diacid, and at least one amino acid are linked together through an ester bond, an amide bond, a urethane bond, and a urea bond;

(4) a poly (ester amide urethane) wherein at least one diol, at least one diacid, and at least one amino acid are linked together through an ester bond, an amide bond, and a urethane bond;

(5) a poly (ester urea) wherein at least one diol and at least one amino acid are linked together through an ester bond and a urea bond (in other words, at least one diol, a carbonic acid, and at least one amino acid are linked together through an ester bond and a urea bond); and (6) a poly (ester urethane) wherein at least one diol and at least one amino acid are linked together through an ester bond and a urethane bond, further wherein the at least one diol is a compound of formula HO—R$_1$—OH, wherein R$_1$ is chosen from C$_1$-C$_{12}$ alkylene optionally interrupted by at least one oxygen, C$_3$-C$_8$ cycloalkylene, C$_3$-C$_{10}$ cycloalkylalkylene,

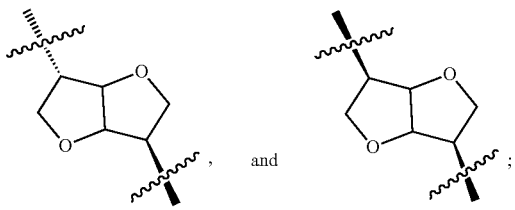

the at least one diacid is a compound of formula HO—(CO)—R$_3$—(CO)—OH, wherein R$_3$ is chosen from C$_1$-C$_2$ alkylene; and the at least one amino acid is a naturally occurring amino acid or a non-naturally occurring amino acid, such as an L-amino acid or D-amino acid, further such as L-glycine, L-alanine, L-valine, L-leucine, L-isoleucine, L-proline, L-methionine, L-phenylalanine, or L-tryptophan, or D isomers thereof.

In some embodiments, R$_1$ is chosen from C$_2$-C$_{12}$ alkylene optionally interrupted by at least one oxygen, C$_3$-C$_8$ cycloalkylene, C$_3$-C$_{10}$ cycloalkylalkylene,

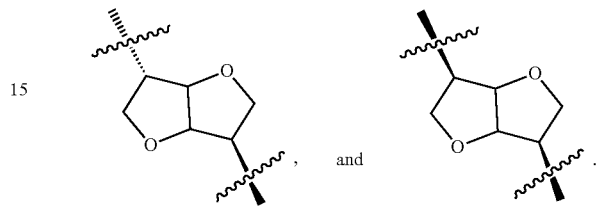

In some embodiments, R$_3$ is chosen from C$_2$-C$_{12}$ alkylene.

In some embodiments, the polymer is selected from (1) a poly (ester amide urea) wherein at least one diol, at least one diacid, and at least one amino acid are linked together through an ester bond, an amide bond, and a urea bond;

(2) a poly (ester urethane urea) wherein at least one diol and at least one amino acid are linked together through an ester bond, a urethane bond, and a urea bond;

(3) a poly (ester amide urethane urea) wherein at least one diol, at least one diacid, and at least one amino acid are linked together through an ester bond, an amide bond, a urethane bond, and a urea bond; and (4) a poly (ester amide urethane) wherein at least one diol, at least one diacid, and at least one amino acid are linked together through an ester bond, an amide bond, and a urethane bond, further wherein the at least one diol is a compound of formula HO—R$_1$—OH, wherein R$_1$ is chosen from C$_1$-C$_{12}$ alkylene optionally interrupted by at least one oxygen, C$_3$-C$_8$ cycloalkylene, C$_3$-C$_{10}$ cycloalkylalkylene,

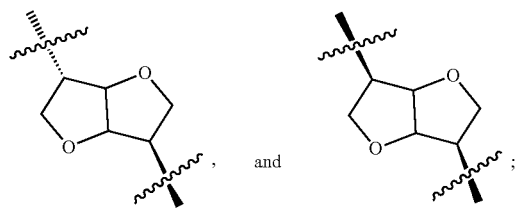

the at least one diacid is a compound of formula HO—(CO)—R$_3$—(CO)—OH, wherein R$_3$ is C$_1$-C$_2$ alkylene; and the at least one amino acid is a naturally occurring amino acid or non-naturally occurring amino acid, such as L-amino acid or D-amino acid, further such as L-valine, L-leucine, L-isoleucine, L-methionine, or L-phenylalanine, or D isomers thereof.

In some embodiments, R$_1$ is chosen from C$_2$-C$_{12}$ alkylene optionally interrupted by at least one oxygen, C$_3$-C$_8$ cycloalkylene, C$_3$-C$_{10}$ cycloalkylalkylene,

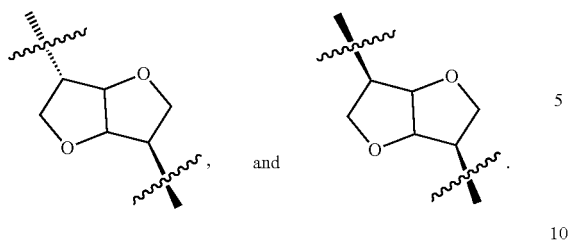

In some embodiments, $R_3$ is chosen from $C_2$-$C_{12}$ alkylene.

In some embodiments, the polymer is grindable. In some embodiments, the grindable polymer is poly (ester urea). In some embodiments, the grindable polymer is poly (ester urea) with low molecular weight, such as 5-6 kDa weight average.

In some embodiments, the polymer is the poly (ester amide urea). In some embodiments, the poly (ester amide urea) comprises the following two blocks with random distribution thereof:

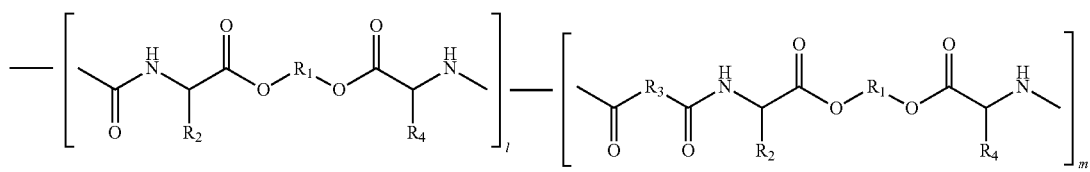

wherein
the range of l:m ratio is from 0.01:0.99 to 0.99:0.01, l+m=1, such as 0.05:0.95 to 0.95:0.05, and further such as 0.10:0.90 to 0.90:0.10;
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

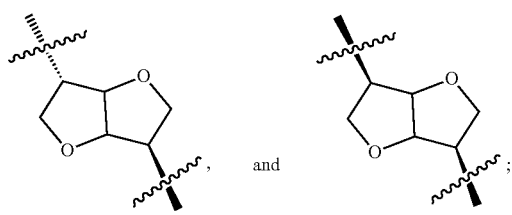

$R_3$ is chosen from $C_1$-$C_2$ alkylene; and
$R_2$ and $R_4$ are independently chosen from the side chains of L- and D-amino acids such that the carbon to which $R_2$ or $R_4$ is attached has L or D chirality. For example, $R_2$ and $R_4$ are independently chosen from —CH(CH$_3$)$_2$, —CH$_2$CH(CH$_3$)$_2$, —CH(CH$_3$)CH$_2$CH$_3$, and —CH$_2$C$_6$H$_5$. $R_2$ and $R_4$ can also be independently chosen from —(CH$_2$)$_3$CH$_3$ and —(CH$_2$)$_3$SCH$_3$, such that the carbons to which they are attached have R or S chirality.

In some embodiments, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

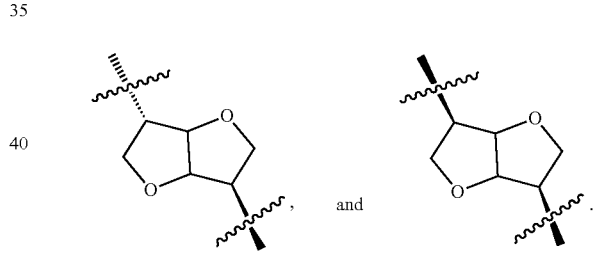

In some embodiments, $R_3$ is chosen from $C_2$-$C_{12}$ alkylene.

In some embodiments of the poly (ester amide urea), $R_1$ is —(CH$_2$)$_6$—. In some embodiments of the poly(ester amide urea), $R_3$ is —(CH$_2$)$_8$—. In some embodiments of the poly (ester amide urea), $R_2$ and $R_4$ are chosen from the side chain of L-leucine.

In some embodiments, the polymer is the poly (ester urethane urea). In some embodiments, the poly (ester urethane urea) comprises the following two blocks with random distribution thereof:

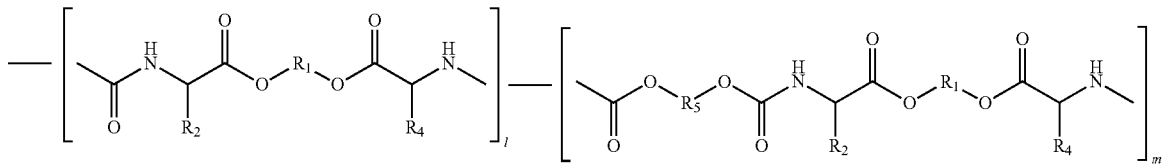

wherein
the ratio of l:m ranges from 0.01:0.99 to 0.99:0.01, l+m=1, such as 0.05:0.95 to 0.95:0.05, and further such as 0.10:0.90 to 0.90:0.10;

$R_1$ and $R_5$ are independently chosen from $C_1$-$C_{12}$ alkylene optionally interrupted by at least one oxygen, $C_3$-$C_8$ cycloalkylene, $C_3$-$C_{10}$ cycloalkylalkylene,

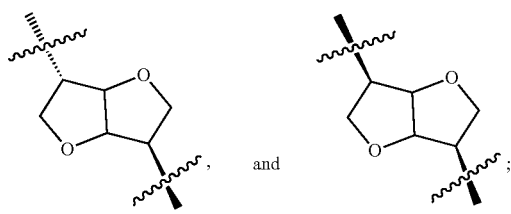

and $R_2$ and $R_4$ are independently chosen from the side chains of L- and D-amino acids such that the carbon to which $R_2$ or $R_4$ is attached has L or D chirality. For example, $R_2$ and $R_4$ are independently chosen from —CH(CH$_3$)$_2$, —CH$_2$CH(CH$_3$)$_2$, —CH(CH$_3$)CH$_2$CH$_3$, and —CH$_2$C$_6$H$_5$. $R_2$ and $R_4$ can also be independently chosen from —(CH$_2$)$_3$CH$_3$ and —(CH$_2$)$_3$SCH$_3$, with the carbons to which they are attached having R or S chirality.

In some embodiments, $R_1$ and $R_5$ are independently chosen from $C_2$-$C_{12}$ alkylene optionally interrupted by at least one oxygen, $C_3$-$C_8$ cycloalkylene, $C_3$-$C_{10}$ cycloalkylalkylene,

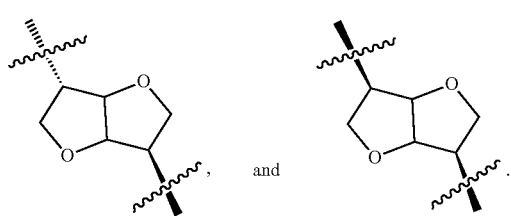

In some embodiments of the poly (ester urethane urea), $R_1$ is —(CH$_2$)$_6$—. In some embodiments of the poly (ester urethane urea), $R_3$ is —(CH$_2$)$_8$—. In some embodiments of the poly (ester urethane urea), $R_2$ and $R_4$ are chosen from the side chain of L-leucine.

In some embodiments, the polymer is the poly (ester amide urethane urea). In some embodiments, the poly (ester amide urethane urea) comprises the following three blocks with random distribution thereof:

wherein
the ratio of l:m:k ranges from 0.05:0.05:0.90 to 0.90:0.05: 0.05, l+m+k=1;

$R_1$ and $R_5$ are independently chosen from $C_1$-$C_{12}$ alkylene optionally interrupted by at least one oxygen, $C_3$-$C_8$ cycloalkylene, $C_3$-$C_{10}$ cycloalkylalkylene,

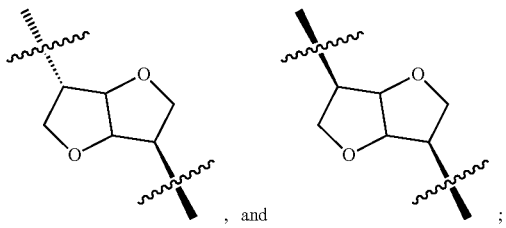

$R_3$ is $C_1$-$C_{12}$ alkylene; and $R_2$ and $R_4$ are independently chosen from the side chains of L- and D-amino acids such that the carbon to which $R_2$ or $R_4$ is attached has L or D chirality. For example, $R_2$ and $R_4$ are independently chosen from —CH(CH$_3$)$_2$, —CH$_2$CH(CH$_3$)$_2$, —CH(CH$_3$)CH$_2$CH$_3$, and —CH$_2$C$_6$H$_5$; $R_2$ and $R_4$ are independently chosen from —(CH$_2$)$_3$CH$_3$ and —(CH$_2$)$_3$SCH$_3$, with the carbons to which they are attached having R or S chirality.

In some embodiments, $R_1$ and $R_5$ are independently chosen from $C_2$-$C_{12}$ alkylene optionally interrupted by at least one oxygen, $C_3$-$C_8$ cycloalkylene, $C_3$-$C_{10}$ cycloalkylalkylene,

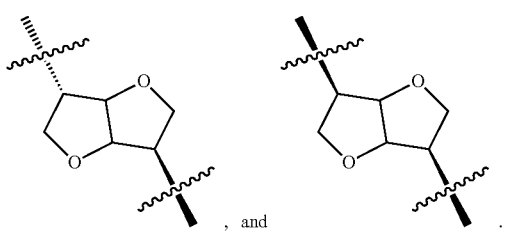

In some embodiments, $R_3$ is chosen from $C_2$-$C_{12}$ alkylene.

In some embodiments of the poly (ester amide urethane urea), $R_1$ is —(CH$_2$)$_6$—. In some embodiments of the poly (ester amide urethane urea), $R_3$ is —(CH$_2$)$_8$—. In some embodiments of the poly (ester amide urethane urea), $R_2$ and $R_4$ are chosen from the side chain of L-leucine.

In some embodiments, the polymer is the poly (ester amide urethane). In some embodiments, the poly (ester amide urethane) comprises the following two blocks with random distribution thereof:

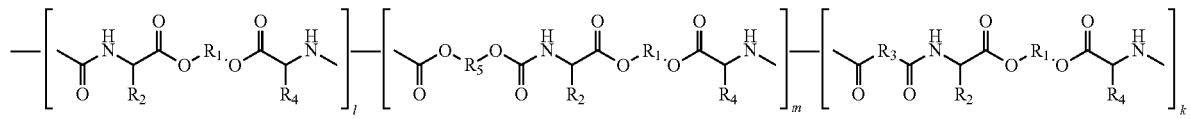

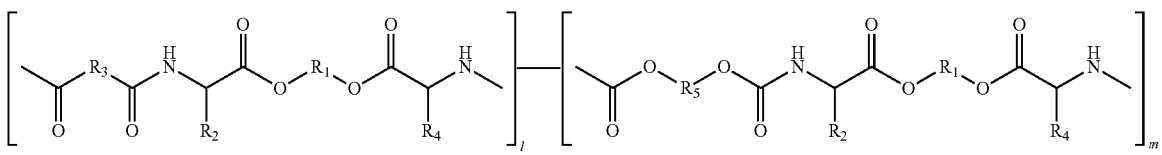

wherein
the ratio of l:m ranges from 0.01:0.99 to 0.99:0.01, l+m=1, such as 0.05:0.95 to 0.95:0.05, and further such as 0.10:0.90 to 0.90:0.10;

$R_1$ and $R_5$ are independently chosen from $C_1$-$C_{12}$ alkylene optionally interrupted by at least one oxygen, $C_3$-$C_8$ cycloalkylene, $C_3$-$C_{10}$ cycloalkylalkylene,

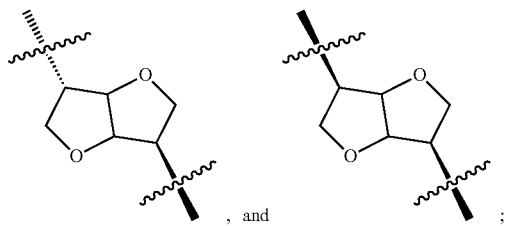

, and ;

$R_3$ is $C_1$-$C_{12}$ alkylene; and
$R_2$ and $R_4$ are independently chosen from the side chains of L- and D-amino acids such that the carbon to which $R_2$ or $R_4$ is attached has L or D chirality. For example, $R_2$ and $R_4$ are independently chosen from —CH(CH$_3$)$_2$, CH$_2$CH(CH$_3$)$_2$, CH(CH$_3$)CH$_2$CH$_3$, and CH$_2$C$_6$H$_5$; $R_2$ and $R_4$ can also be independently chosen from (CH$_2$)$_3$CH$_3$ and (CH$_2$)$_3$SCH$_3$, with the carbons to which they are attached having R or S chirality.

In some embodiments, $R_1$ and $R_5$ are independently chosen from $C_2$-$C_{12}$ alkylene optionally interrupted by at least one oxygen, $C_3$-$C_8$ cycloalkylene, $C_3$-$C_{10}$ cycloalkylalkylene,

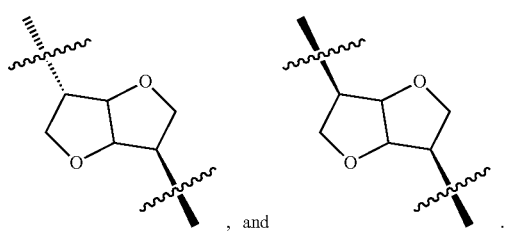

, and .

In some embodiments, $R_3$ is chosen from $C_2$-$C_{12}$ alkylene.

In some embodiments of the poly (ester amide urethane), $R_1$ is —(CH$_2$)$_6$—.

In some embodiments of the poly (ester amide urethane), $R_3$ is —(CH$_2$)$_8$—. In some embodiments of the poly (ester amide urethane), $R_2$ and $R_4$ are chosen from the side chain of L-leucine.

Also provided herein is a polymer blend comprising a first polymer and a second polymer, wherein the first polymer is chosen from:
(1) a poly (ester amide urea) wherein at least one diol, at least one diacid, and at least one amino acid are linked together through an ester bond, an amide bond, and a urea bond;

(2) a poly (ester urethane urea) wherein at least one diol and at least one amino acid are linked together through an ester bond, a urethane bond, and a urea bond;
(3) a poly (ester amide urethane urea) wherein at least one diol, at least one diacid, and at least one amino acid are linked together through an ester bond, an amide bond, a urethane bond, and a urea bond;
(4) a poly (ester amide urethane) wherein at least one diol, at least one diacid, and at least one amino acid are linked together through an ester bond, an amide bond, and a urethane bond;
(5) a poly (ester urea) wherein at least one diol and at least one amino acid are linked together through an ester bond and a urea bond (in other words, at least one diol, a carbonic acid, and at least one amino acid are linked together through an ester bond and a urea bond); and
(6) a poly (ester urethane) wherein at least one diol and at least one amino acid are linked together through an ester bond and a urethane bond, further wherein the at least one diol is a compound of formula HO—$R_1$—OH, wherein $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

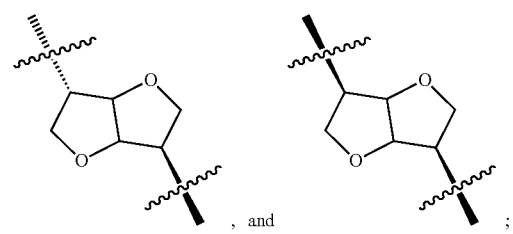

, and ;

the at least one diacid is a compound of formula HO—(CO)—$R_3$—(CO)—OH, wherein $R_3$ is chosen from $C_1$-$C_2$ alkylene; and
the at least one amino acid is a naturally occurring amino acid or a non-naturally occurring amino acid, such as an L-amino acid or D-amino acid, further such as L-glycine, L-alanine, L-valine, L-leucine, L-isoleucine, L-proline, L-methionine, L-phenylalanine, or L-tryptophan, or D isomers thereof; and the second polymer is a poly (ester amide) wherein at least one diol, at least one diacid and at least one amino acid are linked together through an ester bond and an amide bond, wherein the at least one diol is a compound of formula HO—$R_1$—OH, wherein $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

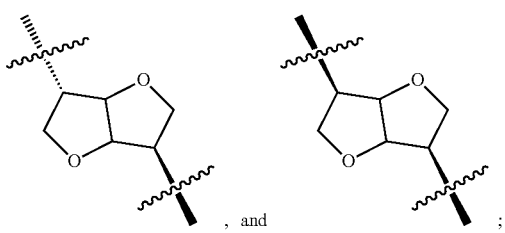

, and ;

the at least one diacid is a compound of formula HO—(CO)—R$_3$—(CO)—OH, wherein R$_3$ is chosen from C$_1$-C$_{12}$ alkylene; and the at least one amino acid is a naturally occurring amino acid or a non-naturally occurring amino acid, such as an L-amino acid or D-amino acid, further such as L-glycine, L-alanine, L-valine, L-leucine, L-isoleucine, L-proline, L-methionine, L-phenylalanine, or L-tryptophan, or D isomers thereof, or the second polymer is a polymer chosen from (1) a poly (ester amide urea) wherein at least one diol, at least one diacid, and at least one amino acid are linked together through an ester bond, an amide bond, and a urea bond;

(2) a poly (ester urethane urea) wherein at least one diol and at least one amino acid are linked together through an ester bond, a urethane bond, and a urea bond;

(3) a poly (ester amide urethane urea) wherein at least one diol, at least one diacid, and at least one amino acid are linked together through an ester bond, an amide bond, a urethane bond, and a urea bond;

(4) a poly (ester amide urethane) wherein at least one diol, at least one diacid, and at least one amino acid are linked together through an ester bond, an amide bond, and a urethane bond;

(5) a poly (ester urea) wherein at least one diol and at least one amino acid are linked together through an ester bond and a urea bond (in other words, at least one diol, a carbonic acid, and at least one amino acid are linked together through an ester bond and a urea bond); and (6) a poly (ester urethane) wherein at least one diol and at least one amino acid are linked together through an ester bond and a urethane bond, further wherein the at least one diol is a compound of formula HO—R$_1$—OH, wherein R$_1$ is chosen from C$_1$-C$_{12}$ alkylene optionally interrupted by at least one oxygen, C$_3$-C$_8$ cycloalkylene, C$_3$-C$_{10}$ cycloalkylalkylene,

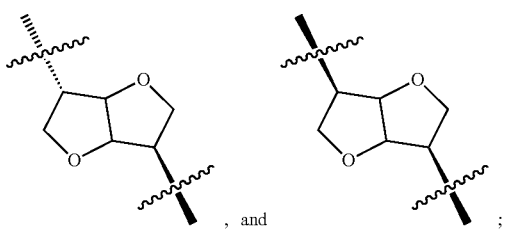

, and ;

the at least one diacid is a compound of formula HO—(CO)—R$_3$—(CO)—OH, wherein R$_3$ is chosen from C$_1$-C$_{12}$ alkylene; and the at least one amino acid is a naturally occurring amino acid or a non-naturally occurring amino acid, such as an L-amino acid or D-amino acid, further such as L-glycine, L-alanine, L-valine, L-leucine, L-isoleucine, L-proline, L-methionine, L-phenylalanine, or L-tryptophan, or D isomers thereof, wherein the first polymer and the second polymer are not the same.

In some embodiments of the polymer blend, R$_1$ for the first polymer is chosen from C$_2$-C$_{12}$ alkylene optionally interrupted by at least one oxygen, C$_3$-C$_8$ cycloalkylene, C$_3$-C$_{10}$ cycloalkylalkylene,

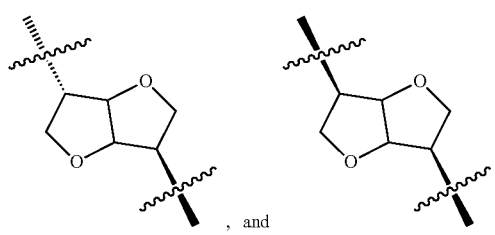

, and .

In some embodiments of the polymer blend, R$_1$ for the second polymer is chosen from C$_2$-C$_{12}$ alkylene optionally interrupted by at least one oxygen, C$_3$-C$_8$ cycloalkylene, C$_3$-C$_{10}$ cycloalkylalkylene,

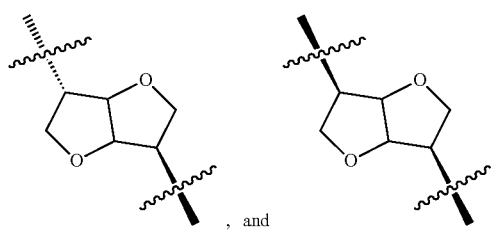

, and in the second polymer.

In some embodiments of the polymer blend, R$_3$ for the first polymer is chosen from C$_2$-C$_{12}$ alkylene.

In some embodiments of the polymer blend, R$_3$ for the second polymer is chosen from C$_2$-C$_{12}$ alkylene.

In some embodiments of the polymer blend, the second polymer is a poly(ester amide). In some embodiments of the polymer blend, the second polymer is a poly(ester amide), wherein the at least one amino acid includes L-leucine. In some embodiments of the polymer blend, the second polymer is a poly(ester amide), wherein the at least one diol includes 1,6-hexanediol. In some embodiments of the polymer blend, the second polymer is a poly(ester amide), wherein the at least one diacid includes sebacic acid.

In some embodiments of the polymer blend, the second polymer is a poly(ester amide), wherein the at least one diol includes 1,6-hexanediol, the at least one diacid includes sebacic acid, and the at least one amino acid includes L-leucine.

In some embodiments of the polymer blend, the second polymer is a poly(ester amide), wherein the at least one amino acid is L-leucine. In some embodiments of the polymer blend, the second polymer is a poly(ester amide), wherein the at least one diol is 1,6-hexanediol. In some embodiments of the polymer blend, the second polymer is a poly(ester amide), wherein the at least one diacid is sebacic acid.

In some embodiments of the polymer blend, the second polymer is a poly(ester amide), wherein the at least one diol is 1,6-hexanediol, the at least one diacid is sebacic acid, and the at least one amino acid is L-leucine.

In some embodiments of the polymer blend, the first polymer is a poly(ester urea). In some embodiments of the polymer blend, the first polymer is a poly(ester urea), wherein the at least one diol includes 1,6-hexanediol. In some embodiments of the polymer blend, the first polymer is a poly(ester urea), wherein the at least one diacid includes carbonic acid. In some embodiments of the polymer blend, the first polymer is a poly(ester urea), wherein the at least one amino acid includes L-leucine.

In some embodiments of the polymer blend, the first polymer is a poly(ester urea), wherein the at least one amino acid includes L-leucine, the at least one diol includes 1,6-hexanediol, and the at least one diacid includes carbonic acid.

In some embodiments of the polymer blend, the first polymer is a poly(ester urea), wherein the at least one diol is 1,6-hexanediol. In some embodiments of the polymer blend, the first polymer is a poly(ester urea), wherein the at least one diacid is carbonic acid. In some embodiments of the polymer blend, the first polymer is a poly(ester urea), wherein the at least one amino acid is L-leucine.

In some embodiments of the polymer blend, the first polymer is a poly(ester urea), wherein the at least one amino acid is L-leucine, the at least one diol is 1,6-hexanediol, and the at least one diacid is carbonic acid.

In some embodiments of the polymer blend, the first polymer is a poly(ester urea) and the second polymer is a poly(ester amide). In some embodiments of the polymer blend, the first polymer is a poly(ester urea), wherein the at least one diol includes 1,6-hexanediol, the at least one diacid includes carbonic acid, and the at least one amino acid includes L-leucine, and the second polymer is a poly(ester amide). In some embodiments of the polymer blend, the first polymer is a poly(ester urea) and the second polymer is a poly(ester amide), wherein the at least one diol includes 1,6-hexanediol, the at least one diacid includes sebacic acid, and the at least one amino acid includes L-leucine. In some embodiments of the polymer blend, the first polymer is a poly(ester urea), wherein the at least one diol includes 1,6-hexanediol, the at least one diacid includes carbonic acid, and the at least one amino acid includes L-leucine, and the second polymer is a poly(ester amide), wherein the at least one diol includes 1,6-hexanediol, the at least one diacid includes sebacic acid, and the at least one amino acid includes L-leucine.

In some embodiments of the polymer blend, the first polymer is a poly(ester urea) and the second polymer is a poly(ester amide). In some embodiments of the polymer blend, the first polymer is a poly(ester urea), wherein the at least one diol is 1,6-hexanediol, the at least one diacid is carbonic acid, and the at least one amino acid is L-leucine, and the second polymer is a poly(ester amide). In some embodiments of the polymer blend, the first polymer is a poly(ester urea) and the second polymer is a poly(ester amide), wherein the at least one diol is 1,6-hexanediol, the at least one diacid is sebacic acid, and the at least one amino acid is L-leucine. In some embodiments of the polymer blend, the first polymer is a poly(ester urea), wherein the at least one diol is 1,6-hexanediol, the at least one diacid is carbonic acid, and the at least one amino acid is L-leucine, and the second polymer is a poly(ester amide), wherein the at least one diol is 1,6-hexanediol, the at least one diacid is sebacic acid, and the at least one amino acid is L-leucine.

In some embodiments of the polymer blend, the first polymer is a poly(ester urea) and the second polymer is a poly(ester amide), wherein the poly(ester urea) comprises repeating units of:

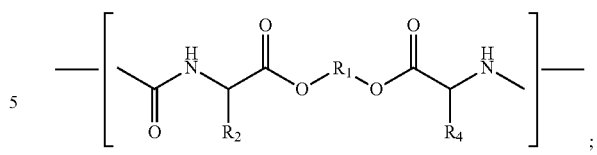

and the poly(ester amide) comprises repeating units of:

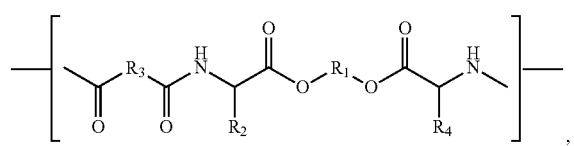

wherein $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

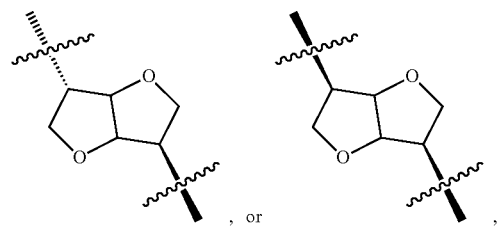

$R_3$ is $C_1$-$C_{12}$ alkylene, $R_2$ and $R_4$ are independently chosen from the side chains of L- and D-amino acids so that the carbon to which $R_2$ or $R_4$ is attached has L or D chirality.

In some embodiments of the polymer blend, the ratio of the first polymer to the second polymer ranges from 0.01:0.99 to 0.99:0.01, such as 0.05:0.95 to 0.95:0.05, further such as 0.30:0.70 to 0.70:0.30, and further such as 0.4:0.6 to 0.6:0.4.

In some embodiments of the polymer blend, the ratio of the first polymer to the second polymer is 0.4:0.6.

In some embodiments of the polymer blend, the ratio of the first polymer to the second polymer is 0.4:0.6, wherein the first polymer is a poly(ester urea) and the second polymer is a poly(ester amide). In some embodiments of the polymer blend, the ratio of the first polymer to the second polymer is 0.4:0.6, wherein the first polymer is a poly(ester urea), wherein the at least one diol is 1,6-hexanediol, the at least one diacid is carbonic acid, and the at least one amino acid is L-leucine, and the second polymer is a poly(ester amide), wherein the at least one diol is 1,6-hexanediol, the at least one diacid is sebacic acid, and the at least one amino acid is L-leucine.

Further provided is a process for preparing a diester,

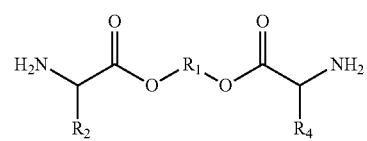

comprising:
heating a mixture comprising

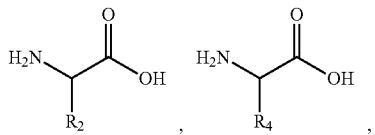

HO—$R_1$—OH, at least one acid that is not an amino acid, and cyclohexane,
wherein
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

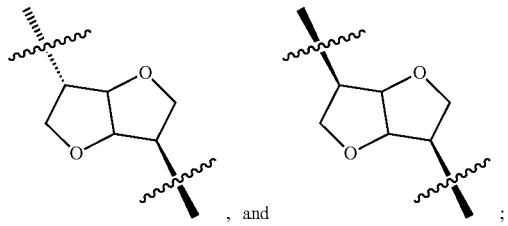

, and

;

$R_2$ and $R_4$ are independently chosen from the side chains of L- and D-amino acids such that the carbon to which $R_2$ or $R_4$ is attached has L or D chirality. For example, $R_2$ and $R_4$ are independently chosen from —$CH(CH_3)_2$, $CH_2CH(CH_3)_2$, $CH(CH_3)CH_2CH_3$, and $CH_2C_6H_5$; $R_2$ and $R_4$ can also be independently chosen from ($CH_2)_3CH_3$ and ($CH_2)_3SCH_3$, with the carbons to which they are attached having R or S chirality;
the at least one acid that is not an amino acid is chosen from inorganic and organic acids such as sulfonic, sulfuric, and hydrochloric acids, including toluene sulfonic acid (o-toluene, m-toluene, and p-toluene-sulfonic acids and methane sulfonic acid.
In some embodiments, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

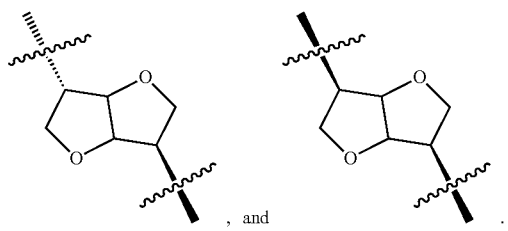

, and

.

In some embodiments, $R_2$ and $R_4$ both are the side chain of L-leucine.
In some embodiments, $R_1$ is —($CH_2)_6$—.
In some embodiments, the at least one acid is p-toluenesulfonic acid monohydrate.
A person of ordinary skill in the art will appreciate that additional steps may be required to prepare a diester wherein $R_2$ or $R_4$ may interfer with diester formation. For example, protection and deprotection steps known in the art be utilized when $R_2$ or $R_4$ is, for example, the side chain of a poly-functional amino acid, such as L-arginine, L-aspartic acid, L-cysteine, L-glutamate, L-histidine, L-lysine, L-tyrosine, L-serine, and D isomers thereof.

The process provided herein for preparing a diester utilizes cyclohexane, a less toxic organic solvent than toluene or benzene, organic solvents used in some previously disclosed processes for producing monomers and intermediates for the synthesis of amino acid based polymers. Cyclohexane demonstrates similar azeotrope properties to benzene under the reaction conditions described herein.

Further provided is a process of preparing the polymers disclosed herein, comprising:

a. mixing a salt of the diester and at least one base in water;
b. mixing at least two bis-electrophiles in an organic solvent;
c. mixing the mixtures from step a and b and stirring vigorously; and
d. obtaining the organic layer including the polymer disclosed herein, wherein the at least two bis-electrophiles are a mixture of diacid chloride of formula Cl(CO)—$R_3$—(CO)Cl and tri-phosgene with a molar ratio of the diacid chloride:triphosgene ranging from 0.95:(0.05/3) to 0.05:(0.95/3) for preparing poly(ester amide urea), or a mixture of dichloroformate of formula Cl(CO)—O—$R_5$—O—(CO)Cl and triphosgene with molar ratio of the dichloroformate:triphosgene ranging from 0.95:(0.05/3) to 0.05:(0.95/3) for preparing poly(ester urethane urea), or a mixture of diacid chloride of formula Cl(CO)—$R_3$—(CO)Cl, di-chloroformate of formula Cl(CO)—O—$R_5$—O—(CO)Cl, and tri-phosgene with molar ratio of the diacid chloride:dichloroformate:triphosgene ranging from 0.90:0.05:(0.05/3) to 0.05:0.05:(0.90/3) for preparing poly(ester amide urethane urea), or a mixture of diacid chloride of formula Cl(CO)—$R_3$—(CO)Cl and di-chloroformate of formula Cl(CO)—O—$R_5$—O—(CO)Cl with molar ratio of the diacid chloride:dichloroformate ranging from 0.95:0.05 to 0.05:0.95 for preparing poly(ester amide urethane), wherein $R_1$ and $R_5$ are independently chosen from $C_1$-$C_{12}$ alkylene optionally interrupted by at least one oxygen, $C_3$-$C_8$ cycloalkylene, $C_3$-$C_{10}$ cycloalkylalkylene,

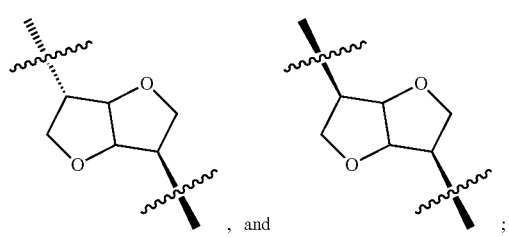

, and

;

and
$R_3$ is $C_1$-$C_{12}$ alkylene.
In some embodiments, $R_1$ and $R_5$ are independently chosen from $C_2$-$C_{12}$ alkylene optionally interrupted by at least one oxygen, $C_3$-$C_8$ cycloalkylene, $C_3$-$C_{10}$ cycloalkylalkylene,

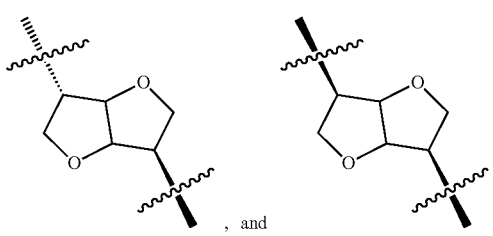

In some embodiments, $R_3$ is $C_2$-$C_{12}$ alkylene.

In some embodiments, the organic solvent is chloroform, dichloromethane, or ethyl acetate. In some embodiments, the at least one base is an inorganic base, such as sodium carbonate. In some embodiments, the organic solvent is amylene-stabilized. For example, in some embodiments, the chloroform, dichloromethane, or ethyl acetate is amylene-stabilized.

In some embodiments, the organic layer obtained in step d is further washed with water one or more times.

In some embodiments, the organic layer obtained after the organic layer obtained in step d is further washed with water one or more times may be used directly for preparing the second composition described below without separation of the polymer.

Alternatively, the poly (ester amide urea) can be prepared by a process comprising
a. mixing triphosgene, diacid HO(CO)—$R_3$—(CO)OH, and at least one organic base in an organic solvent,
b. mixing a salt of the diester and at least one base in water,
c. mixing the mixtures from step a and b and stirring vigorously, and
d. obtaining an organic layer, wherein $R_3$ is the same as defined above, wherein the diester has the following formula:

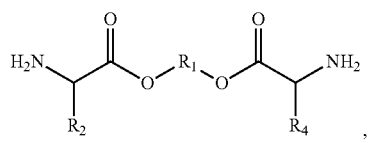

wherein
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

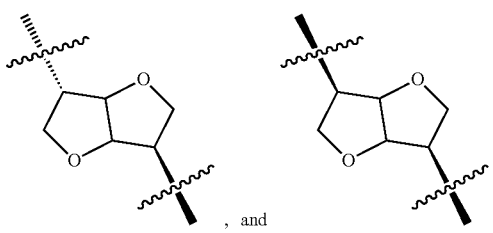

$R_3$ is $C_1$-$C_2$ alkylene; and
$R_2$ and $R_4$ are independently chosen from the side chains of L- and D-amino acids such that the carbon to which $R_2$ or $R_4$ is attached has L or D chirality. For example, $R_2$ and $R_4$ are independently chosen from —CH(CH$_3$)$_2$, CH$_2$CH(CH$_3$)$_2$, CH(CH$_3$)CH$_2$CH$_3$, and CH$_2$C$_6$H$_5$; $R_2$ and $R_4$ can also be independently chosen from (CH$_2$)$_3$CH$_3$ and (CH$_2$)$_3$SCH$_3$, with the carbons to which they are attached having R or S chirality.

In some embodiments, $R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

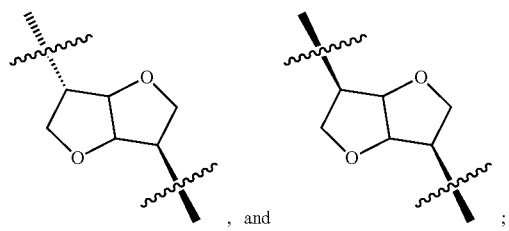

In some embodiments, $R_3$ is $C_2$-$C_{12}$ alkylene.

In some embodiments, the salt of the diester is p-toluenesulfonic acid salt of the diester. In some embodiments, the salt of the diester is a p-toluenesulfonic acid salt of bis-(L-leucine)-1,6-hexylene diester. In some further embodiments, the p-toluenesulfonic acid salt of bis-(L-leucine)-1,6-hexylene diester is prepared by direct condensation of L-leucine with 1,6-hexanediol in the presence of p-toluenesulfonic acid monohydrate in refluxed cyclohexane, wherein the ratio of L-leucine to 1,6-hexanediol to p-toluenesulfonic acid monohydrate is 2:1:X, wherein X is greater than 2.

In some embodiments, the at least one base is an inorganic base, such as sodium carbonate. In some embodiments, the at least one organic base is pyridine.

In some embodiments, the organic solvent is chloroform, dichloromethane, or ethyl acetate. In some embodiments, the organic solvent is amylene-stabilized. For example, in some embodiments, the chloroform, dichloromethane, or ethyl acetate is amylene-stabilized.

In some embodiments, the poly (ester amide urea) is retained in the organic layer obtained in step d.

In some embodiments, the organic layer obtained in step d is further washed with water at least one time.

In some embodiments, the organic layer obtained after the organic layer obtained in step d is further washed with water one or more times may be used directly for preparing the second composition described below without separation of the polymer.

In some embodiments, mixing the mixtures from step a and b and stirring vigorously results in interfacial polycondensation. In some embodiments, the by-products of the interfacial polycondensation are highly water soluble and are retained in water phase. In some embodiments, the by-products of the interfacial polycondensation include sodium chloride and sodium p-toluenesulfonate.

Alternatively, the poly (ester urethane urea) can be prepared by a process comprising
a. mixing triphosgene, diol HO—$R_5$—OH, and at least one organic base in an organic solvent,
b. mixing a salt of the diester and at least one base in water,
c. mixing the mixtures from step a and b and stirring vigorously, and
d. obtaining an organic layer, wherein
the diester has the following formula:

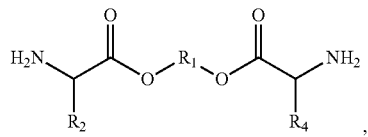

wherein
R$_1$ and R$_5$ are independently chosen from C$_1$-C$_{12}$ alkylene optionally interrupted by at least one oxygen, C$_3$-C$_8$ cycloalkylene, C$_3$-C$_{10}$ cycloalkylalkylene,

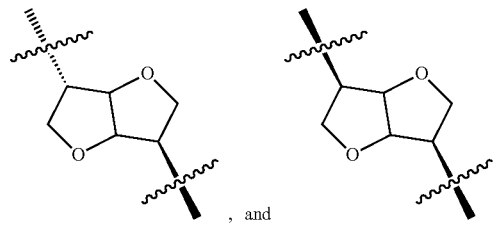

, and ;

and
R$_2$ and R$_4$ are independently chosen from the side chains of L- and D-amino acids such that the carbon to which R$_2$ or R$_4$ is attached has L or D chirality. For example, R$_2$ and R$_4$ are independently chosen from —CH(CH$_3$)$_2$, CH$_2$CH(CH$_3$)$_2$, CH(CH$_3$)CH$_2$CH$_3$, and CH$_2$C$_6$H$_5$; R$_2$ and R$_4$ can also be independently chosen from (CH$_2$)$_3$CH$_3$ and (CH$_2$)$_3$SCH$_3$, with the carbons to which they are attached having R or S chirality.

In some embodiments, R$_1$ and R$_5$ are independently chosen from C$_2$-C$_{12}$ alkylene optionally interrupted by at least one oxygen, C$_3$-C$_8$ cycloalkylene, C$_3$-C$_{10}$ cycloalkylalkylene,

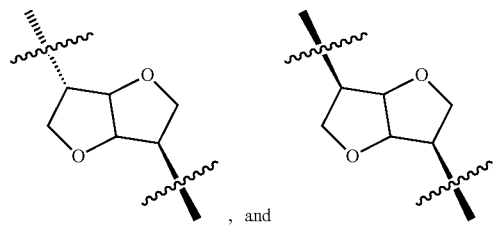

, and .

In some embodiments, the salt of the diester is p-toluenesulfonic acid salt of the diester. In some embodiments, the salt of the diester is a p-toluenesulfonic acid salt of bis-(L-leucine)-1,6-hexylene diester. In some further embodiments, the p-toluenesulfonic acid salt of bis-(L-leucine)-1,6-hexylene diester is prepared by direct condensation of L-leucine with 1,6-hexanediol in the presence of p-toluenesulfonic acid monohydrate in refluxed cyclohexane, wherein the ratio of L-leucine to 1,6-hexanediol to p-toluenesulfonic acid monohydrate is 2:1:X, wherein X is greater than 2.

In some embodiments, the at least one base is an inorganic base, such as sodium carbonate. In some embodiments, the at least one organic base is pyridine.

In some embodiments, the organic solvent is chloroform, dichloromethane, or ethyl acetate. In some embodiments, the organic solvent is amylene-stabilized. For example, in some embodiments, the chloroform, dichloromethane, or ethyl acetate is amylene-stabilized.

In some embodiments, the poly (ester urethane urea) is retained in the organic layer obtained in step d.

In some embodiments, the organic layer obtained after the organic layer obtained in step d is further washed with water one or more times may be used directly for preparing the second composition described below without separation of the polymer.

In some embodiments, the organic layer obtained in step d is further washed with water at least one time.

In some embodiments, mixing the mixtures from step a and b and stirring vigorously results in interfacial polycondensation. In some embodiments, the by-products of the interfacial polycondensation are highly water soluble and are retained in water phase. In some embodiments, the by-products of the interfacial polycondensation include sodium chloride and sodium p-toluenesulfonate.

Poly (ester urea) can be prepared by a process comprising
a. mixing a salt of the diester and at least one base in water,
b. mixing triphosgene in an organic solvent,
c. mixing the mixtures from step a and b and stirring vigorously, and
d. obtaining an organic layer including the poly (ester urea), wherein
the diester has the following formula:

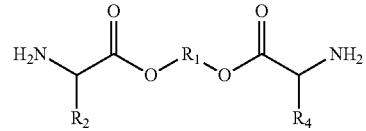

wherein
R$_1$ is chosen from C$_1$-C$_{12}$ alkylene optionally interrupted by at least one oxygen, C$_3$-C$_8$ cycloalkylene, C$_3$-C$_1$ cycloalkylalkylene,

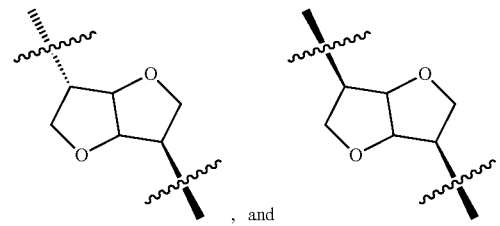

, and ;

and
R$_2$ and R$_4$ are independently chosen from the side chains of L- and D-amino acids such that the carbon to which R$_2$ or R$_4$ is attached has L or D chirality. For example, R$_2$ and R$_4$ are independently chosen from —CH(CH$_3$)$_2$, CH$_2$CH(CH$_3$)$_2$, CH(CH$_3$)CH$_2$CH$_3$, and CH$_2$C$_6$H$_5$; R$_2$ and R$_4$ can also be independently chosen from (CH$_2$)$_3$CH$_3$ and (CH$_2$)$_3$SCH$_3$, with the carbons to which they are attached having R or S chirality.

In some embodiments, R$_1$ is chosen from C$_2$-C$_{12}$ alkylene optionally interrupted by at least one oxygen, C$_3$-C$_8$ cycloalkylene, C$_3$-C$_{10}$ cycloalkylalkylene,

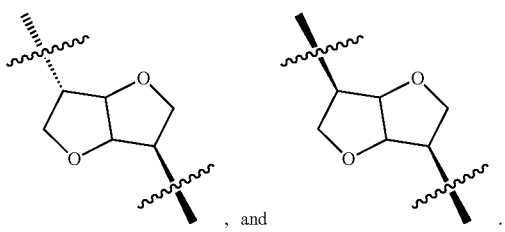

In some embodiments, the salt of the diester is p-toluenesulfonic acid salt of the diester. In some embodiments, the salt of the diester is a p-toluenesulfonic acid salt of bis-(L-leucine)-1,6-hexylene diester. In some further embodiments, the p-toluenesulfonic acid salt of bis-(L-leucine)-1,6-hexylene diester is prepared by direct condensation of L-leucine with 1,6-hexanediol in the presence of p-toluenesulfonic acid monohydrate in refluxed cyclohexane, wherein the ratio of L-leucine to 1,6-hexanediol to p-toluenesulfonic acid monohydrate is 2:1:X, wherein X is greater than 2.

In some embodiments, the organic solvent is chloroform, dichloromethane, or ethyl acetate. In some embodiments, the at least one base is an inorganic base, such as sodium carbonate. In some embodiments, the organic solvent is amylene-stabilized. For example, in some embodiments, the chloroform, dichloromethane, or ethyl acetate is amylene-stabilized.

In some embodiments, the organic layer obtained in step d is further washed with water.

In some embodiments, the organic layer obtained after the organic layer obtained in step d is further washed with water one or more times may be used directly for preparing the second composition described below without separation of the polymer.

Processes for preparing polymers described herein may be completed more quickly than some previously disclosed processes for preparing amino acid based polymers. As a non-limiting example, some previously disclosed amino acid based polymers required 14 to 16 hours to synthesize via solution polycondensation, whereas synthesis of a polymer as described herein may be completed in 15 to 20 minutes.

In some embodiments, processes for preparing polymers described herein do not utilize harmful organic solvents such benzene and toluene, which are required for the synthesis of some previously disclosed biodegradable amino acid based polymers.

In some embodiments, processes for preparing polymers described herein do not utilize organic solvents such as DMF, DMA, and DMSO, which are required for the synthesis of some previously disclosed biodegradable amino acid based polymers. DMF, DMA, and DMSO are not compatible with some bioactive agents, including bacteriophage.

In some embodiments, processes for preparing polymers described herein utilize cost-effective and readily-purchasable reagents such as sebacoyl chloride and triphosgene.

In some embodiments, amino acid based polymers prepared by processes described herein do not need to be separated from the resulting reaction solution prior to preparing a composition comprising the polymer and at least one bioactive agent, such as bacteriophage.

In some embodiments, amino acid based polymers prepared by processes described herein do not require purification prior to preparing a composition comprising the polymer and at least one bioactive agent, such as bacteriophage.

In addition, the polymers described herein may be suitable for preparing bacteriophage-containing compositions for use in wound healing because polymers described herein can be solubilized in chloroform, an organic solvent that does not inactivate bacteriophages when exposure thereto is relatively short, and the ultimate products of their degradation (carbon dioxide, α-amino acids, and neutral fatty diols) can be normal products of human metabolism. Additionally, the ultimate products of their degradation may activate macrophages to produce growth factors that could accelerate and improve wound healing. This is in contrast to many wound dressing materials (e.g., poly(lactide/glycolide) copolymers) that degrade into acidic products that may be harmful to bacteriophages and mammalian cells. Degradation of the polymers described herein may result from hydrolysis of ester bonds in the polymer backbone.

Polymers provided herein can be formed as non-woven porous materials. As a non-limiting example, salt leaching may be used to prepare polymeric films of high porosity. The non-woven porous polymeric materials can be applied to wounds in place of a gauze. In some embodiments, a non-woven porous polymeric material of the disclosure is soaked in liquid bacteriophage and used as a wound dressing.

In some embodiments, the non-woven porous polymeric material may expedite wound healing.

In some embodiments, the non-woven porous polymeric material adheres to the wound site. In some embodiments, adherence of the non-woven porous polymeric material to the wound site results in at least partial suppression of inflammation.

Non-woven porous or non-porous polymeric materials provided herein (as described above or below) do not require removal from the wound site because the materials are biodegradable. In some embodiments, the non-woven porous or non-porous polymeric material may be at least partially degraded during the wound healing process. For example, the non-woven porous polymeric material may be 0.1%, 0.5%, 1%, 5%, 10%, 15%, 20%, 25%, 30%, 35%, 40%, 45%, 50%, 55%, 60%, 65%, 70%, 75%, 80%, 85%, 90%, 95%, 99%, 99.5%, 99.9% or 100% degraded during the wound healing process.

In some embodiments, the non-woven porous polymeric material may be completely degraded during the wound healing process.

Also provided herein is a process for preparing a non-woven porous polymeric material comprising the steps of:
a. mixing a polymer of the disclosure in a mixture comprising at least one salt and an organic solvent;
b. casting the resulting mixture from step a onto a hydrophobic surface;
c. evaporating the organic solvent to obtain a film; and
d. leaching the at least one salt from the film.

In some embodiments, the organic solvent is chloroform, dichloromethane, or ethyl acetate.

In some embodiments, the salt is sodium chloride.

In some embodiments, the mixture is cast between two glass plates and dried for approximately 24 hours.

In some embodiments, drying occurs due to solvent evaporation.

In some embodiments, salt leaching occurs as a result of immersing the film in water for an effective period of time (e.g., 1, 12, 24, or 36 hours).

Compositions

Bacteriophages are polyelectrolytes that have an internal charge dipole.

Provided herein is a first composition in a powdery form comprising at least one bacteriophage.

Also provided herein is a first composition comprising at least one bacteriophage and at least one inorganic salt. In some embodiments, the composition is in the form of dry powder.

Inorganic salts are generally considered to be non-immunogenic. As a result, compositions comprising at least one bacteriophage and at least one inorganic salt may be less likely to provoke an immune response in a patient than previously published phage delivery technologies, which generally utilized phage stabilizing additives that may be immunogenic. As a non-limiting example, gelatin may cause an immune response in some patients.

In some embodiments, the at least one inorganic salt is selected from inorganic salts having poor water solubility, such as calcium salts, magnesium salts, strontium salts, and barium salts, and particularly such as calcium salts and magnesium salts.

In some embodiments, the at least one inorganic salt is selected from calcium carbonate, calcium phosphate, magnesium carbonate, and magnesium phosphate.

Compositions comprising at least one bacteriophage and at least one inorganic salt may protect bacteriophage, which are known to be pH-sensitive, when the compositions are used to treat wounds. As a non-limiting example, a composition comprising at least one bacteriophage and at least one poorly soluble carbonate salt may protect bacteriophage in wound environments that are more acidic than the surrounding tissue. As a result, compositions comprising at least one bacteriophage and at least one inorganic salt may be more therapeutically effective than compositions comprising at least one bacteriophage and no inorganic salts to buffer the wound environment.

In some embodiments, the at least one inorganic salt is a mixture of $MgCO_3$ and $CaCO_3$. In some embodiments, the weight ratio of $MgCO_3$ to $CaCO_3$ ranges from 5:95 to 95:5, such as the ratio is 5:95. The at least one inorganic salt such as calcium and magnesium salts may, in some embodiments, positively influence wound healing by stabilizing and activating the bacteriophage.

In some embodiments, the first composition further comprises at least one other bioactive agent. In some embodiments, the at least one other bioactive agent is selected from: antiseptics, anti-infectives, antibiotics, pain relievers, antibacterials, antiprotozoal agents, and antiviral agents, analgesics, anti-inflammatory agents including steroids and non-steroidal anti-inflammatory agents including COX-2 inhibitors and anti-neoplastic agents, contraceptives, CNS active drugs, hormones, enzymes, hemostatics, proteases, collagenases, and vaccines. Examples of those bioactive agents can be found in other parts of this disclosure. In some embodiments, the first composition is in the form of a spray or patch or film. In other embodiments, the first composition is in the form of a gel or an ointment.

The first composition in dry powder form comprising at least one bacteriophage and at least one inorganic salt can be used to treat infected wounds and cavities. These preparations could also be used to treat osteomyelitis and to fill/reconstruct bone tissues, and could be used in a variety of dental products.

The first composition can be also used in food processing to provide food safety. For example, $CaCO_3$ and $Ca_3(PO_4)_2$ with adsorbed phages (against *Salmonella, Escherichia coli*, etc.) can be very useful in food processing since the salts themselves are widely used as food additives.

The first composition can be also used in livestock against pathogenic bacteria, e.g. pathogenic *E. coli, Salmonella*, etc. These preparations can be added to feed, and carbonate salts can protect the phages from inactivation by the action of acidic media of gastric juice. The first composition can further be used in agriculture to treat plants.

Further provided is a process for preparing the first composition, comprising:
    mixing and holding (incubating) the at least one inorganic salt and the at least one bacteriophage;
    filtrating the suspension obtained to produce the at least one bacteriophage adsorbed (immobilized) wet solid product;
    washing the obtained wet solid product with saline solution optionally; and
    drying the obtained wet solid product through vacuum drying, freeze drying, lyophilization, or spray-drying to obtain the first composition.

In some embodiments, the at least one salt is selected from inorganic salts as disclosed herein. In some embodiments, the at least one salt and at least one bacteriophage in the form of liquid is mixed in an appropriate w/v (g/mL) ratio such as a ratio of 1:10. In some embodiments, the process for preparing the first composition is carried out at room temperature and under sterile conditions.

Also provided is a first composition comprising at least one bacteriophage and components from buffer. In some embodiments, the first composition is in a powdery form. In some embodiments, the buffer comprises at least one inorganic salt. In some embodiments, the buffer is TMN (Tris-$MgCl_2$—NaCl) buffer. In some embodiments, the buffer is Dulbecco's Phosphate Buffered Saline with $MgCl_2$ and $CaCl_2$. Also provided is a process for preparing the first composition comprising 1) mixing at least one bacteriophage and at least one buffer, and 2) drying the mixture through vacuum drying, freeze drying, lyophilization, or spray-drying. In some embodiments, the mixture is dried through freeze drying.

Further provided is a second composition comprising at least one polymer described herein, at least one bioactive agent, and, in some embodiments, at least one filler. For example, in some embodiments of the second composition, the at least one polymer is an amino acid based polymer as described herein. In some embodiments of the second composition, the at least one polymer is a polymer blend as described herein. The second composition may be applied to an internal or external surface of the body to deliver an effective amount of the at least one bioactive agent.

In some embodiments of the second composition, the bioactive agent is selected from bacteriophage and phage product. Non-limiting examples of phage product include endolysin, phage proteins, and phage enzymes.

In some embodiments of the second composition, the bioactive agent comprises one or more of an antiseptic, an anti-infective (e.g., a bacteriophage), a bacteriophage-derived product (e.g., endolysin, phage protein, or phage enzyme), an antibiotic, an antibacterial, an antiprotozoal agent, an antiviral, an analgesic, an anti-inflammatory agent (e.g., steroids or non-steroidal anti-inflammatory agents such as COX-2 inhibitors), an anti-neoplastic agent, a contraceptive, a central nervous system (CNS) active drug, an hormone, an enzyme, or a vaccine.

In some embodiments of the second composition, the bioactive agent comprises one or more of a phage stabilizing additive, a fibrinolytic enzyme, a metabolic process stimulating agent, a vasodilator, a pain killer, mono- and disaccharides, polysaccharides and mucopolysaccharides, an anti-protozoa drug, an anti-fungal drug, a hemostatic, a vitamin, an anti-inflammatory steroid, or an anti-inflammatory non-steroid drug.

Non-limiting examples of the enzymes include those that can catalyze the hydrolysis (erosion) of the polymer disclosed herein. The hydrolysis (erosion) of the polymers disclosed herein can be important for the release of the at least one bioactive agent into the surrounding tissues. At least one enzyme may also be used, as a non-limiting example, to treat wounds and abrasions by removing the dead or infected skin from the site of injury. Non-limiting examples of the at least one enzyme include papain, collagenase, elastase, fibrinolysin, hyaluronidase, trypsin, α-chymotrypsin and lipase. In some embodiments of the second composition, the at least one enzyme is selected from trypsin, α-chymotrypsin and lipase.

Non-limiting examples of antibiotics include fluoroquinolones (e.g., tetracycline, ciprofloxacin, and levofloxacin), monoxycarbolic acid antibiotics (e.g., mupirocin), aminoglycosides (e.g., neomycin), macrolide antibiotics (e.g., erythromycin), bacitracin, Polymyxin, and mixtures thereof. Additional non-limiting examples of antibiotics include silver salts (e.g., silver sulfadiazine and silver nitrate), chlorohexidine, and mafenide acetate.

A non-limiting example of a phage stabilizing additive is calcium gluconate.

Non-limiting examples of fibrinolytic enzymes include hyaluronidase and fibrinolysin.

A non-limiting example of a metabolic process simulating agent is methyluracyl.

Non-limiting examples of vasodilators include sodium hydrocarbonate and L-arginine.

Exemplary pain relievers include, but are not limited to, benzocaine, lidocaine, tetracaine, pramocaine, dibucaine, and mixtures thereof.

A non-limiting example of an anti-protozoa drug is metronidazole.

A non-limiting example of an anti-fungal drug is clotrimazolum.

A non-limiting example of a hemostatic is thrombin.

A non-limiting example of an anti-inflammatory steroid is prednisolone.

A non-limiting example of an anti-inflammatory non-steroid drug is sodium diclofenac (Voltaren).

In some embodiments of the second composition, the second composition comprises at least one antibiotic selected from silver salts (e.g., silver sulfadiazine and silver nitrate), chlorohexidine, and mafenide acetate.

In some embodiments of the second composition, the second composition comprises calcium gluconate as a phage stabilizing additive.

In some embodiments of the second composition, the second composition comprises at least one fibrinolytic enzyme selected from hyaluronidase and fibrinolysin. In some embodiments, the composition comprises methyluracyl as a metabolic process simulating agent.

In some embodiments of the second composition, the second composition comprises sodium hydrocarbonate or L-arginine as a vasodilator.

In some embodiments of the second composition, the second composition comprises benzocaine.

In some embodiments of the second composition, the second composition comprises metronidazole.

In some embodiments of the second composition, the second composition comprises clotrimazolum.

In some embodiments of the second composition, the second composition comprises thrombin.

In some embodiments of the second composition, the second composition comprises prednisolone.

In some embodiments of the second composition, the second composition comprises sodium diclofenac.

In some embodiments of the second composition, the at least one filler is selected from inorganic salts, sucrose, and gelatin. In some embodiments of the second composition, the inorganic salts include calcium salts, magnesium salts, strontium salts, and barium salts. In some embodiments of the second composition, the at least one filler is selected from calcium salts and magnesium salts. In some embodiments of the second composition, the at least one filler is selected from calcium carbonate, calcium phosphate, magnesium carbonate, and magnesium phosphate. In some embodiments of the second composition, the at least one filler is selected from calcium carbonate and magnesium carbonate. In some embodiments, the at least one filler is a mixture of calcium carbonate and magnesium carbonate.

In some embodiments of the second composition, the at least one polymer is selected from poly (ester amide urea), poly (ester urethane urea), poly (ester amide urethane urea), and poly (ester amide urethane).

In some embodiments, the second composition comprises at least one polymer selected from poly (ester amide urea), poly (ester urethane urea), poly (ester amide urethane urea), and poly (ester amide urethane), at least one bacteriophage or phage product, calcium carbonate, magnesium carbonate, benzocaine, ciprofloxacin, and an enzyme such as chymotrypsin. In some embodiments, the second composition comprises a poly (ester amide urea), at least one bacteriophage or phage product, calcium carbonate, magnesium carbonate, benzocaine, ciprofloxacin, and an enzyme such as chymotrypsin.

In some embodiments of the second composition, the at least one polymer is a polymer blend as described herein. In some embodiments of the second composition, the at least one polymer is a polymer blend wherein the first polymer is a poly(ester urea) and the second polymer is a poly(ester amide). In some embodiments of the second composition, the first polymer is a poly(ester urea), wherein the at least one diol is 1,6-hexanediol, the at least one diacid is carbonic acid, and the at least one amino acid is L-leucine, and the second polymer is a poly(ester amide), wherein the at least one diol is 1,6-hexanediol, the at least one diacid is sebacic acid, and the at least one amino acid is L-leucine.

In some embodiments of the second composition, the second composition comprises a poly(ester urea), a poly (ester amide), at least one bacteriophage or phage product, calcium carbonate, magnesium carbonate, benzocaine, ciprofloxacin, and an enzyme such as chymotrypsin.

In some embodiments of the second composition, the at least one polymer is grindable. In some embodiments, the second composition comprising a grindable polymer is in the form of fine powder suitable for application in a spray wound dressing.

The second composition described herein may also possess desirable mechanical properties for wound dressings, including tissue-like elasticity. In some embodiments, the second composition described herein may possess sufficient plasticity to form a film, which can be manually deformed to fit tightly to an irregular biological surface (e.g., a concave wound surface).

In some embodiments of the second composition, the second composition is in the form of a perforated film, a patch, a film or a spray. In other embodiments of the second composition, the second composition is in the form of an unperforated film, a gel, a hydrogel, or an ointment. In some embodiments of the second composition, the film form of the second composition may be a single layer or multiple layers. The person skilled in this art will appreciate that patches and perforated films can be of any practical dimension. Additionally, the patches and perforated films disclosed herein can be designed in virtually any size or shape, as may be useful for one or more specific applications. Additionally, films made from the second composition described herein may be readily separable by gentle manual force, desirably leaving each sheet of film intact upon separation.

In some embodiments of the second composition, the second composition is in the form of a non-woven porous material. As a non-limiting example, salt leaching may be used to prepare non-woven porous materials.

In some embodiments of the second composition, the second composition in the form of a non-woven porous material adheres to the wound site. In some embodiments, adherence of the non-woven porous material to the wound site results in at least partial suppression of inflammation.

Also provided herein is a process for preparing a non-woven porous polymeric material comprising the steps of:
 a. mixing a polymer of the disclosure in a mixture comprising at least one salt and an organic solvent;
 b. casting the resulting mixture from step a onto a hydrophobic surface;
 c. evaporating the organic solvent to obtain a film; and
 d. leaching the at least one salt from the film.

In some embodiments of the second composition, the second composition may be used to provide a coating on a support material, which may or may not be biodegradable, such as a fibrous or non-fibrous three-dimensional construct or a woven support. Constructs prepared with the second composition may be part of devices including a support material to be used as, for example, bandages for wounds or burn dressings.

In some embodiments, constructs comprising the second composition may be surgically implanted. Constructs according to the present disclosure may also be formed into devices for wound packing, such as gel foams, or may be used as components in surgical appliances, such as Penrose drains, indwelling catheters, catheters for peritoneal dialysis, and any other appliances that are in contact with body cavities, the blood circulation, or the lymphatic circulation and are used to treat both infection and potential infections.

Additional non-limiting embodiments include constructs for oral hygiene such as gum implants (e.g., for periodontal disease or dental caries). Such constructs may contain at least one or more bioactive agent released in a controlled manner upon erosion of the construct. Suitable selections of particular bioactive agents and effective amounts thereof will be readily apparent to the person skilled in the art in view of the intended site of implantation.

Further provided is a method of treating a patient having an ulcerative wound comprising inserting into the wound or covering the wound with the second composition as disclosed herein.

In some embodiments, the wound is open or infected.

In some embodiments, the at least one bacteriophage in the second composition is specific for bacteria found in the wound.

Further provided is a process for preparing the second composition, comprising:
 a. mixing the first composition described herein with a mixture comprising an organic solvent and at least one polymer disclosed herein; optionally adding at least one another bioactive agent;
 b. casting the resulting mixture from step a onto a hydrophobic surface; and
 c. removing the organic solvent to obtain a film containing the second composition.

In some embodiments, the organic solvent is dichloromethane.

In some embodiments, the mixture comprises 13% w/v polymer.

In some embodiments, mixing in step a is performed slowly at a speed of 100 rpm or lower.

In some embodiments, mixing in step a is accomplished using a friction type homogenizer with pestle at a speed of 100 rpm or lower. In some embodiments, mixing in step a occurs for 10 minutes.

In some embodiments, the hydrophobic surface is a Teflon petri dish.

In some embodiments, removal of the organic solvent occurs via evaporation. In some embodiments, removal of the organic solvent occurs via evaporation over the course of four days.

In some further embodiments, a vacuum-drier is used to remove excess solvent. In some embodiments, the vacuum-drier operates at 37° C.

Alternatively, provided is a process for preparing the second composition, comprising
 a. mixing a liquid comprising at least one bacteriophage with a mixture comprising an organic solvent and at least one polymer disclosed herein; optionally adding at least one filler selected from the inorganic salts disclosed above and at least one another bioactive agent;
 b. casting the resulting mixture from step a onto a hydrophobic surface; and
 c. removing the organic solvent to obtain a film containing the second composition.

In some embodiments, the organic solvent is chloroform. In other embodiments, the organic solvent is dichloromethane or ethyl acetate. In some embodiments, the mixture comprising an organic solvent and at least one polymer further comprises additional bioactive agent chosen from antiseptics, anti-infectives, such as bacteriophages, antibiotics, antibacterials, antiprotozoal agents, and antiviral agents, analgesics, anti-inflammatory agents including steroids and non-steroidal anti-inflammatory agents including COX-2 inhibitors, anti-neoplastic agents, contraceptives, CNS active drugs, hormones, hemostatics, enzymes, proteases, and vaccines.

Alternatively, provided herein in a process for preparing the second composition comprising
 a. mixing the at least one bioactive agent with a mixture comprising an organic solvent and at least one polymer described herein;
 b. casting the resulting mixture from step a onto a hydrophobic surface; and
 c. removing the organic solvent to obtain a film.

In some embodiments, the second composition comprises poly (ester amide urea), at least one or more bacteriophage, calcium carbonate, magnesium carbonate, benzocaine, ciprofloxacin, and chymotrypsin.

Also provided herein is a wound dressing comprising the first composition or the second composition disclosed herein.

Also provided herein is an implantable surgical device comprising the first composition or the second composition disclosed herein.

Also provided herein is a food or animal feed additive comprising the first composition or the second composition disclosed herein.

Also provided herein is a method of treating agricultural crops comprising administering the first composition or the second composition disclosed herein. In some embodiments, the first composition or the second composition is administered by spraying the composition on the agricultural crops.

EXAMPLES

The present application refers to a number of documents, the contents of which are hereby incorporated by reference to the extent they disclose suitable, conventional methods known to those skilled in the field. Also, the present application claims priority from U.S. patent application Ser. No. 15/188,783 filed Jun. 21, 2016, which is also hereby incorporated by reference in its entirety.

The following examples are intended for illustration purposes only and should not be construed as limiting the scope of the disclosure or the claims appended hereto in any way.

All exemplary preparations should be performed under sterile conditions with sterile glass-ware and storage vessels. In addition, a chemical hood with good ventilation or a biological hood should be used when performing exemplary preparations described below.

Example 1: Preparation of bis-(alpha-amino acid)-alkylene diester: General Procedure

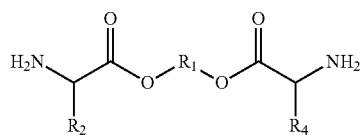

A mixture of

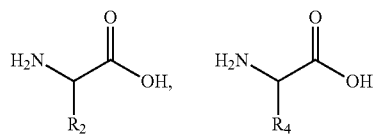

(R2 and R4 are defined as before, which can be the same or different, both amino acids together are 2 moles), HO—R1—OH (R1 is defined as before, 1 mole), and p-TsOH monohydrate (2 moles) is refluxed in cyclohexane.

Examples for

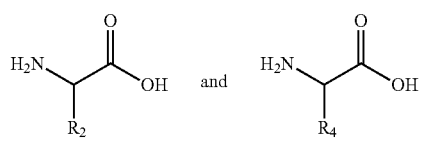

include L-amino acids, such as L-leucine.

Examples for HO—$R_1$—OH can be any aliphatic diol, including α,ω-alkylene diols like HO—$(CH_2)_k$—OH (i.e. non-branched), branched diols (e.g., 1,2-propylene glycol), cyclic diols (e.g. dianhydrohexitols and cyclohexanediol), or oligomeric diols based on ethylene glycol such as diethylene glycol, triethylene glycol, tetraethylene glycol, or poly(ethylene glycol)s). A further example of HO—R—OH can be 1,6-hexanediol.

One exemplary diester is bis(L-leucine)-1,6-hexylene diester with the following structure:

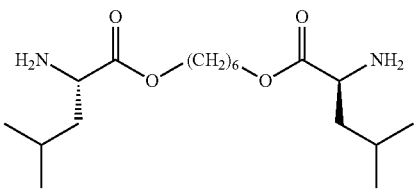

Di-p-toluenesulfonic acid salt of bis-(L-leucine)-1,6-hexylene diester may be prepared by refluxing a mixture of L-leucine (2 moles), 1,6-hexanediol (1 mole), and p-TsOH monohydrate (2 or more moles) in cyclohexane.

Example 2: Preparation of Bis-Electrophilic Monomers

A. Diacid Chlorides

Diacid chloride of formula Cl(CO)—$R_3$—(CO)Cl can be prepared as follows: gently heating (such as heating at 40-50° C.) free di-acids (OH(CO)—$R_3$—(CO)OH) with excess of chlorinating agent that is thionyl chloride, or 2 moles of chlorinating agent what is phosphorus pentachloride $PCl_5$ (2 moles per 1 mole of di-acid), without using any catalyst and organic solvent; additional heating at 40-50° C. for 12 h after complete dissolution of solid diacid; removing the excess thionyl chloride or phosphorus oxychloride ($POCl_3$) at 40-50° C. under reduced pressure. R3 is as defined before.

This procedure can result in pure, polycondensation grade di-acid chlorides which are used in the preparation of the polymers disclosed herein directly, without additional purification.

B. Preparation of Dichloroformate of Diols

Di-chloroformate Cl(CO)—O—$R_5$—O—(CO)Cl can be prepared as follows: gently heating (40-50° C.) the HO—$R_5$—OH with excess phosgene (6-8 moles per 1 mole of diol) in tetrahydrofuran (THF) solution until complete dissolution of solid diol; additional heating at 40-50° C. for 12 h; removing THF and excess phosgene at 40-50° C. under reduced pressure. This procedure results in pure, polycondensation grade di-chloroformates which are used in the preparation of the polymers disclosed herein directly, without additional purification. $R_5$ is as defined before.

Example 3: Preparation of the Polymers

General Procedures for the Synthesis of the Polymers Via Interfacial Polycondensation Poly(ester urea), poly(ester urethane), poly(ester amide urea), poly(ester urethane urea), poly(ester amide urethane), and poly(ester amide urethane urea) are prepared using the following protocol.

2.0 mol of di-p-toluenesulfonic acid salt of bis(L-amino acid)-alkylene diester is added to a reactor suitable for interfacial polycondensation. 15.0 L of water is then added to the reactor with stirring. To the obtained suspension of di-p-toluenesulfonic acid salt of bis(L-amino acid)-alkylene diester in water, 6.0 mol of anhydrous sodium carbonate is added with stirring at room temperature for approximately 30-40 min. Hereafter, the aqueous solution of di-p-toluenesulfonic acid salt of bis(L-amino acid)-alkylene diester and anhydrous sodium carbonate is referred to as the first solution.

In a separate reaction vessel, 2.0 mol of bis-electrophilic monomer or a mixture of at least two bis-electrophilic monomers, totaling 2.0 mol of bis-electrophilic monomer, is dissolved in 6.5 L of amylene-stabilized chloroform. Hereafter, the solution of bis-electrophilic monomer in amylene-stabilized chloroform is referred to as the second solution. Other solvents may be used in place of amylene-stabilized chloroform, including but not limited to, amylene-stabilized methylene chloride, dichloromethane, and ethyl acetate, among others.

The second solution is quickly added to the first solution at 15-20° C. to produce a water/organic mixture. The water/organic mixture is vigorously stirred for approximately 15-20 minutes. After the cessation of stirring, the mixture is allowed to separate, resulting in a two-layer system. The lower layer, comprising polymer in chloroform, is separated and washed 3 times (3×6 L) with distilled water to remove the salts (sodium chloride, sodium carbonate/bicarbonate, and sodium p-toluene sulfonate). The chloroform layer is separated after each wash step. After washing, the chloroform layer is dried over anhydrous $Na_2SO_4$ (0.8-1.0 kg) and filtered off. The obtained chloroform layer is stored for the subsequent applications, including, but not limited to, the preparation of bacteriophage containing bio-composites.

When preparing poly(ester amide urea), the second solution contains two bis-electrophilic monomers, i.e., a diacid chloride and tri-phosgene, at a molar ratio ranging from 0.95:(0.05/3) to 0.05:(0.95/3).

When preparing poly(ester urethane urea), the second solution contains a mixture of two bis-electrophilic monomers, i.e., a dichloroformate of a diol and tri-phosgene, at a molar ratio ranging from 0.95:(0.05/3) to 0.05:(0.95/3).

When preparing poly(ester amide urethane urea), the second solution contains a mixture of three bis-electrophilic monomers, a diacid chloride, a dichloroformate of a diol, and tri-phosgene, at a molar ratio ranging from 0.9:0.05:(0.05/3) to 0.05:0.05:(0.9/3).

When preparing poly(ester amide urethane), the second solution contains a mixture of two bis-electrophilic monomers, i.e., a diacid chloride and a dichloroformate of a diol, at a molar ratio ranging from 0.99:0.01 to 0.01:0.99, such as 0.05:0.95 to 0.95:0.05, and further such as 0.10:0.90 to 0.90:0.10.

In alternative procedures, the polymer is isolated after the polycondensation reaction by placing the obtained chloroform layer in a glass vessel and removing the solvent (chloroform) by distillation under atmospheric pressure. As will be recognized by those skilled in the art, "atmospheric pressure" may be relative depending on geographic location, and the exact transition point may vary slightly depending on ambient conditions, for example, geographic location or temperature.

Subsequently, 6.0 Ls of hot water (70-80° C.) are added to the formed mass to obtain a polymer solution. The resulting rubbery polymer is removed from the glass vessel and placed between plates, which is squeezed to remove residual water. The plates are placed in an oven equipped with a fan and dried at 100° C. For further drying, the polymer is moved to a vacuum-drier and dried at 100° C.

The polymer is weighed at regular intervals and dried until the polymer weight did not change over the course of multiple weighing times.

A. Poly(Ester Amide Urea)

Di-p-toluenesulfonic acid salt of bis(L-leucine)-1,6-hexylene diester (1.378 g, 2.0 mol) was added to a reactor suitable for interfacial polycondensation. Water (15.0 L) was added to the reactor with stirring. To the obtained suspension, anhydrous sodium carbonate (0.636 kg, 6.0 mol) was added and stirred at room temperature for approximately 30-40 min (the first solution). In a separate vessel, triphosgene (0.1682 kg, 1.7/3 mol) and sebacoyl chloride (i.e., $ClCO-(CH_2)_8-COCl$, 0.0717 kg, 0.3 mol) were dissolved in 6.5 L of amylene-stabilized chloroform (the second solution). The second solution was rapidly added to the first solution at room temperature to produce a water/organic mixture.

The water/organic mixture was stirred vigorously for about 15-20 min. Following cessation of stirring, the mixture was allowed to separate completely, resulting in a two-layer system. The lower layer containing poly(ester urea amide) in chloroform was separated and washed 3 times (3×6 L) with distilled water to remove the salts (sodium chloride, sodium carbonate/bicarbonate, and sodium p-toluene-sulfonate). The chloroform layer was separated after each wash step.

After washing, the chloroform layer was separated again, dried over anhydrous $Na_2SO_4$ (0.8-1.0 kg), and filtered off. The solution was then diluted up to the desired concentration, 0.6 kg of the polymer in 8.0 L of chloroform. The filtered solution contained ca. 0.78 kg of the polymer in ca. 6.5 L of chloroform. To obtain the desirable concentration (0.6 kg in 8.0 L), 2.75 L of amylene-stabilized chloroform was added to 5.25 L of the polymer solution. The resulting solution contains 0.6 kg of the polymer in 8.0 L chloroform and is ready for preparing the composition.

In one instance, the polymer was isolated right after the polycondensation reaction according to the following procedure: the obtained chloroform layer after filtering off $Na_2SO_4$ was placed in glass vessel and the solvent (chloroform) was removed by distillation under atmospheric pressure (ca. 5.5-6.0 LL chloroform is collected). Afterwards, 6.0 Ls of hot water (ca. 70-80° C.) were added to the formed mass. The resulting rubbery polymer was removed from the glass vessel and placed onto the Teflon® plates, squeezed to remove and pour out the residual water, the plates was placed in an oven equipped with a fan and dried at 100° C. For a final drying the polymer was moved to a vacuum-drier and dried at 100° C. up to constant weight. Yield: 0.743 kg (95%). Mw=45-55 kDa, Polydispersity (Mw/Mn)=1.6-1.8 (gel phase chromatography; a solution of LiBr (0.1 M) in N,N-dimethylformamide was used as an eluent at a flow rate 1.0 mL/min).

B. Poly(Ester Urea Urethane)

In a similar example, poly(ester urea urethane) can be prepared by interfacial polycondensation of di-p-toluenesulfonic acid salt of bis-(L-leucine)-1,6-hexylene diester (1.0 mole) with a mixture of di-chloroformate of 1,6-hexanediol/triphosgene at a molar ratio 0.15:(0.85/3).

C. One-Pot Synthesis of Poly(Ester Urea Amide)s—General Procedure 2.0 mole of di-p-toluenesulfonic acid salt of bis(L-amino acid)-alkylene diester is placed in a reactor for interfacial polycondensation. 15.0 L of water is added on stirring. To the obtained suspension 0.636 kg (6.0 mol) of anhydrous sodium carbonate is added and stirred at room temperature for about 30-40 min (The 1st solution).

In a separate vessel, x mole of dicarboxylic acid (of general formula HOCO—(CH$_2$)y-COOH) and 2 x mole of dry pyridine in 6.5 L of amylene-stabilized chloroform (2+5x)/3 mole [2x mole for in situ synthesis of a mole of di-acid chloride which forms (ester amide) blocks+(2−x)/3 mole which forms (ester urea) blocks] of triphosgene is added and stirred for an appropriate time (The 2nd solution).

To the 1st solution is quickly added the 2nd solution at 15-20° C. and the water/organic mixture is vigorously stirred for about 15-20 min. The stirrer is stopped and the mixture is allowed to separate, resulting in two layer system. The lower layer, containing the polymer in chloroform, is separated, washes 3-times (3×6 L) with distilled water to remove the salts—sodium chloride, sodium carbonate/bicarbonate, and sodium p-toluene sulfonate; the chloroform layer is separated after each portion of washing with water. After washing, the chloroform layer is separated again, dried over anhydrous Na$_2$SO$_4$ (0.8-1.0 kg) and filtered off. The obtained chloroform solution is stored for the subsequent use.

D. One-Pot Synthesis of Poly (Ester Urethane Urea)—General Procedure 2.0 mole of di-p-toluenesulfonic acid salt of bis(L-amino acid)-alkylene diester is placed in a reactor for interfacial polycondensation. 15.0 L of water is added on stirring. To the obtained suspension is added anhydrous sodium carbonate (0.636 kg, 6.0 mol) of and stirred at room temperature for about 30-40 min (The 1$^{st}$ solution).

In a separate vessel, x mole of alkylenediol (of general formula HO—(CH$_2$)$_x$—OH) and 2x mole of dry pyridine in 6.5 L of amylene-stabilized chloroform (2+x)/3 mole [2x/3 mole for in situ synthesis of x mole bis-chloroformate which forms (ester urethane) blocks+(2−x)/3 mole which forms (ester urea) blocks] of triphosgene was added and stirred for an appropriate time (The 2$^{nd}$ solution).

To the 1$^{st}$ solution is added the 2$^{nd}$ solution i quickly at 15-20° C. and the water/organic mixture is vigorously stirred for about 15-20 min. The stirrer is stopped and the mixture is allowed to separate, resulting in two layer system. The lower layer, containing the polymer in chloroform, is separated, is washed 3-times (3×6 L) with distilled water to remove the salts—sodium chloride, sodium carbonate/bicarbonate, and sodium p-toluene sulfonate; the chloroform layer is separated after each portion of washing with water. After washing, the chloroform layer is separated again, is dried over anhydrous Na$_2$SO$_4$ (0.8-1.0 kg) and filtered off. The obtained chloroform solution is stored for the subsequent use.

E. Grindable Poly (Ester Urea)

2.0 mole of di-p-toluenesulfonic acid salt of bis(L-leucine)-1,6-hexylene diester was placed in a reactor for interfacial polycondensation. Water (15.0 L) was added to the reactor on stirring. To the obtained suspension was added 0.636 kg (6.0 mol) of anhydrous sodium carbonate. The resulting mixture was stirred at room temperature for about 30-40 min (The 1st solution).

1.9 mole triphosgene (5 mol % deficient as compared with bis(L-leucine)-1,6-hexylene diester above) was dissolved in 6.5 L of amylene-stabilized chloroform in a separate vessel (The 2nd solution).

To the 1st solution was the 2nd solution quickly at 15-20° C. and the water/organic mixture was vigorously stirred for about 15-20 min. The stirrer was stopped and the mixture was allowed to separate, resulting in two layer system. The lower layer, containing poly (ester urea) in chloroform, was separated, washed 3-times (3×6 L) with distilled water to remove the salts—sodium chloride, sodium carbonate/bicarbonate, and sodium p-toluene sulfonate.

The chloroform layer was separated after each portion of washing with water. After washing, chloroform layer was separated again, dried over anhydrous Na$_2$SO$_4$ (0.8-1.0 kg) and filtered off. The obtained chloroform solution was stored for the subsequent use. The obtained poly(ester urea) labeled as LMW-1L6 was of low-molecular-weight (M$_w$=5-6 KDa) and was grindable in solid state.

Example 4: Preparation of Powdery Bacteriophages (the First Composition)

Powdery salts with immobilized bacteriophages were prepared by the incubation of at least one salt in a liquid preparation of at least one bacteriophage and subsequent drying using vacuum-drying, freeze-drying, or spray-drying methods.

The at least one salt (i.e., absorbent) was selected from, for example, MgCO$_3$, CaCO$_3$, and Ca$_3$(PO$_4$)$_2$. The average particle size of MgCO$_3$, CaCO$_3$, and Ca$_3$(PO$_4$)$_2$ is 200, 50, and 5 µm, respectively.

The at least one bacteriophage was selected from, for example, *Staphylococcus aureus*, Pyophage (a cocktail of five phages: *E. coli, Proteus, Staphylococcus aureus, Streptococcus*, and *Pseudomonas aeruginosa*) and Intestiphage (a cocktail of seven phages: *E. coli, Proteus, Staphylococcus aureus, Streptococcus, Pseudomonas aeruginosa, Shigella*, and *Salmonella*). All were prepared by Biochimpharm, LLC, Tbilisi, Ga.

Step 1. Incubation of the Solid Adsorbents and Phages

To 0.3 kg of powdery adsorbent (MgCO$_3$, CaCO$_3$, Ca$_3$(PO$_4$)$_2$) was added 3.0 L (w/v ration 1:10) of liquid bacteriophage (*Staphylococcus*, Pyophage, or Intestiphage) preparation at room temperature. The mixture was thoroughly homogenized by stirring for 20-30 min. The stirring was stopped and the mixture was kept at room temperature for an additional 30 min without agitation.

Step 2. Filtration of the Obtained Suspension, Obtaining (Wet) "Phage-Adsorbed" Solid Product The suspension obtained in Step 1 was filtered off under sterile conditions. The filtrates (F) are referred below as Salt/Bacteriophage,F$_0$:

MgCO$_3$/Staphylophage,F$_0$
CaCO$_3$/Staphylophage,F$_0$
Ca$_3$(PO$_4$)$_2$/Staphylophage,F$_0$
CaCO$_3$/Pyophage,F$_0$
Ca$_3$(PO$_4$)$_2$/Pyophage,F$_0$
CaCO$_3$/intestiphage,F$_0$ The filtrates were analyzed for Plaque Forming Units (PFU) to determine which portions of phages were adsorbed by solid adsorbents and which portion was lost with the filtrates.

The phage-containing (phage-immobilized) wet solid products that was obtained on the filter contained about 0.7 L (20-23) % of the initial liquid. The obtained wet solid products were moved to sterile glass vessels. These wet (W) solids were referred below as Salt/Bacteriophage,W$_0$:

MgCO$_3$/Staphylophage,W$_0$
CaCO$_3$/Staphylophage,W$_0$
Ca$_3$(PO$_4$)$_2$/Staphylophage,W$_0$ (see FIG. 4 for the activity of this wet solid)
CaCO$_3$/Pyophage,W$_0$
Ca$_3$(PO$_4$)$_2$/Pyophage,W$_0$
CaCO$_3$/intestiphage,W$_0$ (see FIG. 5 for the activity of this wet solid)

The wet solids obtained were used for:
(i) quantitative analysis (PFU determination after desorption of phages),
(ii) washing (see Step 3), and
(iii) drying (see Step 4).

Analysis

Analysis Filtrates—Salt/Bacteriophage,$F_0$: Aliquots was removed from the filtrates and PFUs were determined using the double agar overlay method of Gratia (Gratia A. Des relations numériques entre bactéries lysogènes et particules de bactériophage. Annales de l'Institut Pasteur 57:652-676 (1936), and Gratia J.-P. Andre Gratia: A forerunner in microbial and viral genetics. *Genetics* 156:471-476 (2000). The filtrates were also subjected to UV-analysis with the purpose to determine which portion of admixtures were removed after Steps 1 and 2. Admixtures refer to, for example, both proteins and products of bacterial lysis—debris of nucleic acids (absorb at 260 nm) and proteins (absorb at 280 nm). See, e.g. F.-X. Schmid, *Biological Macromolecules: UV-visible Spectrophotometry. ENCYCLOPEDIA OF LIFE SCIENCES*/& 2001 Macmillan Publishers Ltd, Nature Publishing Group/www.els.net). A wide absorption pick in the region 250-300 nm (see FIGS. 1 and 2) corresponds to a mixture of debris of nucleic acids and proteins.

Desorption of phages from Salt/Bacteriophage, $W_0$: 10.0 g of the wet solid (that corresponds to ca. 3.0 g of the dry adsorbent) and 30.0 mL of saline solution (w/v ratio 1:10 per dry adsorbent—the same as in the Step 1 above) were placed in a 250.0 mL flat-bottom flask, sealed with a stopper and shook for 15 min. The flask was removed from a shaker and kept until the solid was precipitated. Right after the solid was precipitated, an aliquot was carefully removed from the supernatant for the determination of PFUs using the double agar overlay method of Gratia (Gratia A. Des relations numériques entre bactéries lysogènes et particules de bactériophage. Annales de l'Institut Pasteur 57:652-676 (1936), and Gratia J.-P. Andre Gratia: A forerunner in microbial and viral genetics. *Genetics* 156:471-476 (2000)) (see Results section below).

Step 3. Washing of the Obtained Solid Product by Saline Solution (Optional; can be Done for Several Times in Case of Need)

Salt/Bacteriophage,$W_0$ product (ca. 1.0 kg-0.3 kg of the adsorbent+0.7 kg of adsorbed water) obtained after Step 2 was treated by saline (0.9% NaCl solution) similar to the procedure described in the Step 1: to the moist solid (1.0 kg) was added 3.0 L of saline solution and the mixture was thoroughly homogenized by stirring for 20-30 min. The stirring was stopped, the mixture was kept at r.t. for additional 30 min without agitation and filtered off.

The filtrates obtained after washing the Salt/Bacteriophage,$W_0$, were referred below as Salt/Bacteriophage,$F_1$:
$MgCO_3$/Staphylophage,$F_1$
$CaCO_3$/Staphylophage,$F_1$
$Ca_3(PO_4)_2$/Staphylophage,$F_1$
$CaCO_3$/Pyophage,$F_1$
$Ca_3(PO_4)_2$/Pyophage,$F_1$
$CaCO_3$/Intestiphage,$F_1$ The filtrates obtained after Step 3 were analyzed for PFU to determine which portions of phages were adsorbed by the solid adsorbents and which portions were lost with the filtrates.

The wet solid products obtained on the filter were moved to sterile glass vessels. These wet solids obtained after washing were referred below as Salt/Bacteriophage,$W_1$:

$MgCO_3$/Staphylophage,$W_1$
$CaCO_3$/Staphylophage,$W_1$
$Ca_3(PO_4)_2$/Staphylophage,$W_1$
$CaCO_3$/Pyophage,$W_1$
$Ca_3(PO_4)_2$/Pyophage,$W_1$
$CaCO_3$/intestiphage,$W_1$ The obtained wet solids were used for:
(i) quantitative analysis (PFUs determination after desorption of phages), and
(ii) drying (see Step 4).

Analysis

Filtrates: Salt/Bacteriophage,$F_1$: Aliquots was removed from the filtrates and PFUs were determined using the double agar overlay method of Gratia. The filtrates were also subjected to UV-analysis with the purpose to determine which portion of admixtures were removed after the Steps 3 (See Results below).

Desorption of phages from Salt/Bacteriophage,$W_1$: 10.0 g of the wet solid (that corresponds to ca. 3.0 g of the dry adsorbent) and 30.0 mL of saline solution (w/v ratio 1:10 per dry adsorbent—the same as in the Step 1 above) were placed in a 250.0 mL flat-bottom flask, sealed with a stopper and shook for 15 min. The flask was removed from a shaker and kept until the solid precipitated. Right after the solid was precipitated, an aliquot was carefully removed from the supernatant for the determination of PFUs using the double agar overlay method of Gratia (See Results below).

Step 4. Drying of the Obtained Solid Products Salt/Bacterio-Phage,$W_0$ or Salt/Bacteriophage,$W_1$ The wet solids obtained on the filters after the Step 2 or Step 3 were subjected to drying using 3 different methods:
Vacuum drying at 40-45° C. over a water adsorbent (anhydrous $CaCl_2$ or $Na_2SO_4$, or silica gel),
Freeze-drying, and
Spray-drying.

Vacuum drying is the simplest drying method as it does not require the use of complex and expensive equipment. However, vacuum drying requires the use of water adsorbents (anhydrous $CaCl_2$ or $Na_2SO_4$, or silica gel) that should be regenerated (dried at 200-250° C. to remove water) before the repeated use.

Freeze-drying does not require the use of water adsorbent, but freeze-driers are generally more expensive than vacuum-driers. It should be noted that freeze-drying of Salt/Bacteriophage,W wet solids takes about 5-fold less time than freeze-drying of liquid bacteriophages since freeze drying of Salt/Bacteriophage,W wet solids utilizes 5-fold less water.

Spray-drying requires the most expensive equipment, but it is preferable to vacuum drying and freeze-drying for continuous processes.

For freeze-drying, Salt/Bacteriophage,W wet solids are mixed with saline solutions (1.0 kg of wet solid+3.0 L of saline solution—w/v ratio 1:10 per dry adsorbent) to obtain suspensions that are to be supplied (feed) to spray drier. Mild conditions for spray drying bacteriophages are found—air temperature at the inlet 90-95° C., and 50° C. at the outlet; the latter is to be regulated by the selection of suspension's appropriate feed rate. In this case, dry powdery preparations contain NaCl (27 g that comes from 3.0 L of saline solution).

The dried solids to be obtained after drying of Salt/Bacteriophage,$W_0$ are labeled as Salt/Bacteriophage,$W_0$VD (vacuum dried) or Salt/Bacteriophage,$W_0$FD (Freeze-dried)

Results Before Drying

In the tables given below, the results for cases 1-3 were obtained after Step 1, Step 2, and Step 3. The results for cases 4-6 were obtained after Step 1.

| Case 1: MgCO₃ + Staphylophage ||||
| --- | --- | --- | --- |
| Sample # | Liquid bacteriophage sample | PFU | pH |
| 1 | *Staphylococcus aureus* * | $0.9 \times 10^8$ | 7.74 |
| 2 | MgCO$_3$/Staphylophage, F$_0$ | $2.0 \times 10^6$ | 9.47 |
| 3 | MgCO$_3$/Staphylophage, W$_0$ ** | $4.0 \times 10^7$ | 9.48 |
| 4 | MgCO$_3$/Staphylophage, F$_1$ | $1.0 \times 10^2$ | 9.52 |
| 5 | MgCO$_3$/Staphylophage, W$_1$ *** | $0.9 \times 10^7$ | 9.42 |

\* Serial preparation of Biochimpharm, LLC, Tbilisi, Georgia
\*\* Desorbed from MgCO$_3$/Staphylophage, W$_0$
\*\*\* Desorbed from MgCO$_3$/Staphylophage, W$_1$ Degree of the adsorption of Staphylophages after the Step $1=(0.9\times10^8-2.0\times10)/(0.9\times10^8)\times100=97.8\%$.
Degree of the adsorption (retention) of Staphylophages after the Step $3=(0.9\times10^8-2.0\times10^6-1.0\times10^2)/(0.9\times10^8)\times100\approx97.8\%$
Also see FIGS. 1A-C for UV analysis of Sample #1, Sample #2, and Sample #3 in Case 1, respectively.

Case 2: CaCO$_3$+Staphylophage

| Case 2: CaCO₃ + Staphylophage ||||
| --- | --- | --- | --- |
| Sample # | Liquid bacteriophage sample | PFU | pH |
| 1 | *Staphylococcus aureus* * | $2.0 \times 10^8$ | 7.76 |
| 2 | CaCO$_3$/Staphylophage, F$_0$ | $3.0 \times 10^6$ | 7.39 |
| 3 | CaCO$_3$/Staphylophage, W$_0$ ** | $1.0 \times 10^8$ | 7.59 |
| 4 | CaCO$_3$/Staphylophage, F$_1$ | $1.0 \times 10^5$ | 7.31 |
| 5 | CaCO$_3$/Staphylophage, W$_1$ *** | $9.0 \times 10^7$ | 7.38 |

\* Serial preparation of Biochimpharm, LLC, Tbilisi, Georgia
\*\* Desorbed from CaCO$_3$/Staphylophage, W$_0$
\*\*\* Desorbed from CaCO$_3$/Staphylophage, W$_1$ Degree of the adsorption of Staphylophages after Step $1=(2.0\times10^8-3.0\times10^6)/(2.0\times10^8)\times100=98.5\%$.
Degree of the adsorption (retention) of Staphylophages after Step $3=(2.0\times10^8-3.0\times10^1-1.0\times10^5)/(2.0\times10^8)\times100\approx98.0\%$.
Also see FIGS. 2A-C for UV analysis of Sample #1, Sample #2, and Sample #3 in Case 2, respectively.

| Case 3: Ca₃(PO₄)₂ + Staphylophage ||||
| --- | --- | --- | --- |
| Sample # | Liquid bacteriophage sample | PFU | pH |
| 1 | *Staphylococcus aureus* * | $7.0 \times 10^9$ | 7.65 |
| 2 | Ca$_3$(PO$_4$)$_2$/Staphylophage, F$_0$ | $7.0 \times 10^7$ | 7.72 |
| 3 | Ca$_3$(PO$_4$)$_2$/Staphylophage, W$_0$ ** | $4.0 \times 10^9$ | 7.79 |
| 4 | Ca$_3$(PO$_4$)$_2$/Staphylophage, F$_1$ | $1.0 \times 10^7$ | 7.77 |
| 5 | Ca$_3$(PO$_4$)$_2$/Staphylophage, W$_1$ *** | $2.0 \times 10^9$ | 7.58 |

\* Serial preparation of Biochimpharm, LLC, Tbilisi, Georgia
\*\* Desorbed from Ca$_3$(PO$_4$)$_2$/Staphylophage, W$_0$
\*\*\* Desorbed from Ca$_3$(PO$_4$)$_2$/Staphylophage, W$_1$ Degree of the adsorption of Staphylophages after Step $1=(7.0\times10^9-7.0\times10^7)/(7\times10^9)\times100=99.0\%$
Degree of the adsorption (retention) of Staphylophages after Step $3=(7.0\times10^9-7.0\times10^7-1.0\times10^7)/(7\times10^9)\times100\approx99.0\%$.

| Case 4: CaCO3 + Pyophage ||||
| --- | --- | --- | --- |
| Sample # | Liquid bacteriophage sample | PFU | pH |
| 1 | Pyophage* | $7.0 \times 10^9$ | 7.36 |
|  | *E. coli* | $8.0 \times 10^9$ |  |
|  | *Proteus* | $8.0 \times 10^9$ |  |

| Case 4: CaCO₃ + Pyophage ||||
| --- | --- | --- | --- |
| Sample # | Liquid bacteriophage sample | PFU | pH |
|  | *Staphylococcus* | $9.0 \times 10^9$ |  |
|  | *Streptococcus* | $5.0 \times 10^9$ |  |
|  | *Pseudomonas aeruginosa* |  |  |
| 2 | CaCO$_3$/Pyophage, F$_0$ | $2.0 \times 10^6$ | 7.41 |
|  | *E. coli* | $2.0 \times 10^4$ |  |
|  | *Proteus* | $1.0 \times 10^4$ |  |
|  | *Staphylococcus* | $5.0 \times 10^3$ |  |
|  | *Streptococcus Pseudomonas aeruginosa* | $1.0 \times 10^5$ |  |
| 3 | CaCO$_3$/Pyophage, W$_0$** | $2.0 \times 10^8$ | 7.66 |
|  | *E. coli* | $1.0 \times 10^8$ |  |
|  | *Proteus* | $1.0 \times 10^7$ |  |
|  | *Staphylococcus* | $1.0 \times 10^6$ |  |
|  | *Streptococcus Pseudomonas aeruginosa* | $1.0 \times 10^7$ |  |

\*Serial preparation of Biochimpharm, LLC, Tbilisi, Georgia
\*\*Desorbed from CaCO$_3$/Pyophage, W$_0$ Degree of the adsorption of the phages at Step 1:
$E.\ coli=(7.0\times10^9-2.0\times10^6)/(7.0\times10^9)\times100\approx100\%$
$Proteus=(8.0\times10^9-2.0\times10^4)/(8.0\times10^9)\times100\approx100\%$
$Staphylococcus=(8.0\times10^9-1.0\times10^4)/(8.0\times10^9)\times100\approx100\%$
$Streptococcus=(9.0\times10^9-5.0\times10^3)/(9.0\times10^9)\times100\approx100\%$
$Pseudomonas\ aeruginosa=(5.0\times10^9-1.0\times10^5)/(5.0\times10^9)\times100\approx100\%$

| Case 5: Ca₃(PO₄)₂ + Pyophage ||||
| --- | --- | --- | --- |
| Sample # | Liquid bacteriophage sample | PFU | pH |
| 1 | Pyophage* | $5.0 \times 10^9$ | 7.15 |
|  | *E. coli* | $3.0 \times 10^9$ |  |
|  | *Proteus* | $3.0 \times 10^9$ |  |
|  | *Staphylococcus* | $2.0 \times 10^9$ |  |
|  | *Streptococcus Pseudomonas aeruginosa* | $9.0 \times 10^8$ |  |
| 2 | Ca$_3$(PO$_4$)$_2$/Pyophage, F$_0$ | $5.0 \times 10^6$ | 7.59 |
|  | *E. coli* | $9.0 \times 10^7$ |  |
|  | *Proteus* | $2.0 \times 10^7$ |  |
|  | *Staphylococcus* | $3.0 \times 10^6$ |  |
|  | *Streptococcus Pseudomonas aeruginosa* | $1.0 \times 10^6$ |  |
| 3 | Ca$_3$(PO$_4$)$_2$/Pyophage, W$_0$** | $4.0 \times 10^8$ | 7.49 |
|  | *E. coli* | $5.0 \times 10^8$ |  |
|  | *Proteus* | $2.0 \times 10^8$ |  |
|  | *Staphylococcus* | $4.0 \times 10^5$ |  |
|  | *Streptococcus Pseudomonas aeruginosa* | $3.0 \times 10^7$ |  |

\*Serial preparation of Biochimpharm, LLC, Tbilisi, Georgia
\*\*Desorbed from Ca$_3$(PO$_4$)$_2$/Pyophage, W$_0$ Degree of the adsorption of the phages at Step 1:
$E.\ coli=(5.0\times10^9-5.0\times10^6)/(5.0\times10^9)\times100\approx99.9\%$ $Proteus=(3.0\times10^9-9.0\times10^7)/(3.0\times10^9)\times100\approx97.0\%$
$Staphylococcus=(3.0\times10^9-2.0\times10^7)/(3.0\times10^9)\times100\approx99.3\%$ $Streptococcus=(2.0\times10^9-3.0\times10^6)/(2.0\times10^9)\times100\approx99.8\%$ $Pseudomonas\ aeruginosa=(9.0\times10^8-1.0\times10^6)/(9.0\times10^8)\times100\approx99.9\%$

| Case 6: CaCO3 + Intestiphage ||||
| --- | --- | --- | --- |
| Sample # | Liquid bacteriophage sample | PFU | pH |
| 1 | Intestiphage* | $6.0 \times 10^9$ | 7.37 |
|  | *E. coli* | $9.0 \times 10^9$ |  |
|  | *Proteus* | $7.0 \times 10^9$ |  |

-continued

| Case 6: CaCO3 + Intestiphage | | | |
|---|---|---|---|
| Sample # | Liquid bacteriophage sample | PFU | pH |
| | Staphylococcus | $1.0 \times 10^9$ | |
| | Enterococcus | $7.0 \times 10^9$ | |
| | Pseudomonas aeruginosa | $3.0 \times 10^9$ | |
| | Shigella | $1.0 \times 10^9$ | |
| | Salmonella | | |
| 2 | CaCO$_3$/Intestiphage, F$_0$ | $4.0 \times 10^6$ | 7.40 |
| | E. coli | $8.0 \times 10^4$ | |
| | Proteus | $1.0 \times 10^4$ | |
| | Staphylococcus | $7.0 \times 10^7$ | |
| | Enterococcus | $1.0 \times 10^5$ | |
| | Pseudomonas aeruginosa | $2.0 \times 10^5$ | |
| | Salmonella | $8.0 \times 10^7$ | |
| 3 | CaCO$_3$/Intestiphage, W$_0$** | $3.0 \times 10^8$ | 7.60 |
| | E. coli | $2.0 \times 10^8$ | |
| | Proteus | $3.0 \times 10^7$ | |
| | Staphylococcus | $5.0 \times 10^7$ | |
| | Enterococcus | $7.0 \times 10^7$ | |
| | Pseudomonas aeruginosa | $2.0 \times 10^6$ | |
| | Shigella | $7.0 \times 10^7$ | |
| | Salmonella | | |

*Serial preparation of Biochimpharm, LLC, Tbilisi, Georgia
**Desorbed from CaCO$_3$/Intestiphage, W$_0$ Degree of the adsorption of the phages at Step 1:
E. coli=$(6.0\times10^9-4.0\times10^6)/(6.0\times10^9)\times100 \approx 99.9\%$
Proteus=$(9.0\times10^9-8.0\times10^4)/(9.0\times10^9)\times100 \approx 100.0\%$
Staphylococcus=$(7.0\times10^9-1.0\times10^4)/(7.0\times10^9)\times 100 \approx 100.0\%$
Enterococcus=$(1.0\times10^9-7.0\times10^7)/(1.0\times10^9)\times100 \approx 93.0\%$
Pseudomonas aeruginosa=$(7.0\times10^9-1.0\times10^5)/(7.0\times10^9)\times100 \approx 100.0\%$
Shigella=$(3.0\times10^9-2.0\times10^5)/(3.0\times10^9)\times100 \approx 100\%$
Salmonella=$(1.0\times10^9-8.0\times10^7)/(1.0\times10^9)\times100 = 92\%$ The filtrates obtained after Step 2 contained too low quantity (in terms of PFUs) of bacteriophages (Samples #2 of the Cases 1-6) compared to initial PFUs (Samples #1 of the Cases 1-6). This could be connected with either inactivation of phages or their adsorption by the used salts.

To verify that this was connected with the phages adsorption rather than inactivation, desorption of the phages from the wet solids Salt/Bacteriophage,W$_0$ (Samples #3 of the Cases 1-6) with saline solution was carried out. It was found that large quantities of the phages comparable with the initial PFUs were desorbed in all 6 Cases studied. This strongly evidenced that the water-insoluble salts—MgCO$_3$, CaCO$_3$, and Ca$_3$(PO$_4$)$_2$ intensively adsorbed the bacteriophages from the water solutions, and the degree of the adsorption in all cases was over 90% (in some cases almost 100%).

After washing (Step 3) of wet solids Salt/Bacteriophage, W$_0$ with saline solution, some portions of bacteriophages were lost as determined by measuring PFUs of the filtrates Salt/Bacteriophage,F$_1$ (shown for Staphylophage, Samples #4 of the Cases 1-3). However, the basic portions of the phages were retained by the salt adsorbents MgCO$_3$, CaCO$_3$, and Ca$_3$(PO$_4$)$_2$ as proved by high PFUs of the phages desorbed with saline solution from wet solids Salt/Bacteriophage,W$_1$ (Samples #5 of the Cases 1-3).

Among the salts examined as adsorbents, CaCO$_3$ and Ca$_3$(PO$_4$)$_2$ appeared to adsorb phages intensively without influencing the pH of bacteriophage solutions. MgCO$_3$ appeared to be a good adsorbent, however, it appeared to increase the solutions' pH (makes them more alkaline), which can harm phages. Therefore, taking at the same time into account the positive role of Mg++ cations in wound healing (Alimohammad A., Mohammadali M., Mahmod K., Khadijeh S. A Study of the effect of Magnesium hydroxide on the wound healing process in rats, Medical Journal of Islamic World Academy of Sciences, 16(4), 165-170 (2007)) along with Ca++ cations (Lansdown A. B., Calcium: a potential central regulator in wound healing in the skin. Wound Repair Regen. 10(5), 271-85 (2002)), MgCO$_3$ can be added to the dry powdery phage preparation obtained on the basis of Ca-salts.

Results after Drying

A. Vacuum Drying

Protocol of vacuum drying. The wet solid Salt/Bacteriophage,W$_0$ (or Salt/Bacteriophage,W$_1$) was placed in a vacuum drier and dried under reduced pressure at 45° C. over water adsorbent (anhydrous CaCl$_2$) or Na$_2$SO$_4$, or silica gel) up to constant weight.

| Case 7: CaCO$_3$ + Pyophage | | |
|---|---|---|
| Components of serial Pyophage, | PFU | PFU of the phages desorbed from the vacuum-dried powdery preparation CaCO3/Pyophage, W$_0$VD (PFU of the phages desorbed from the wet preparation (desorbed from the wet preparation CaCO$_3$/Pyophage,W$_0$) |
| E. coli | $7.0 \times 10^9$ | $9.0 \times 10^7$ ($2.0 \times 10^8$) |
| Proteus | $8.0 \times 10^9$ | $8.0 \times 10^7$ ($1.0 \times 10^8$) |
| Staphylococcus aureus | $8.0 \times 10^9$ | $8.0 \times 10^6$ ($1.0 \times 10^7$) |
| Streptococcus | $9.0 \times 10^9$ | $8.0 \times 10^5$ ($1.0 \times 10^6$) |
| Pseudomonas aeruginosa | $5.0 \times 10^9$ | $4.0 \times 10^7$ ($7.0 \times 10^7$) |

B. Freeze Drying

Protocol of freeze-drying. The wet solid Salt/Bacteriophage,W$_0$ (or Salt/Bacterio-phage,W$_1$) was frozen and placed in a freeze-drier and dried up to constant weight.

| Case 8: CaCO$_3$ + Pyophage | | |
|---|---|---|
| Components of serial Pyophage, | PFU | PFU of the phages desorbed from the freeze-dried powdery preparation CaCO$_3$/Pyophage, W$_0$FD (PFU of the phages desorbed from the wet preparation (desorbed from the wet preparation CaCO$_3$/Pyophage,W$_0$) |
| E. coli | $7.0 \times 10^9$ | $1.0 \times 10^8$ ($2.0 \times 10^8$) |
| Proteus | $8.0 \times 10^9$ | $1.0 \times 10^8$ ($1.0 \times 10^8$) |
| Staphylococcus aureus | $8.0 \times 10^9$ | $9.0 \times 10^6$ ($1.0 \times 10^7$) |
| Streptococcus | $9.0 \times 10^9$ | $9.0 \times 10^5$ ($1.0 \times 10^6$) |
| Pseudomonas aeruginosa | $5.0 \times 10^9$ | $6.0 \times 10^7$ ($7.0 \times 10^7$) |

To determine the bacteriophages content in the dried preparations, 3.0 g of a powdery (dry) phage preparation and 30.0 mL of saline solution was placed in a 250 mL flat-bottom flask, sealed with a stopper and shook for 15 min. The flask was removed from a shaker and kept until the solid was precipitated. Right after the solid was precipitated, an aliquot, containing desorbed phages, was removed from the supernatants for the determination of PFU using the double agar overlay method of Gratia.

The results given in Cases 7 and 8 above showed that the PFU of the bacteriophages desorbed from the dried preparations CaCO$_3$/Pyophage, WoVD and CaCO$_3$/Pyophage, WoFD with saline solution were somewhat lower compared to the PFU of the bacteriophages desorbed from the wet preparation $CaCO_3$/Pyophage,$W_0$ that were given in parentheses (see also Sample #3 of the Case 4).

In turn, the PFU of the bacteriophages desorbed from the powdery preparation $CaCO_3$/Pyophage, WoFD (Case 8) was a little bit higher than the PFU of the bacteriophages desorbed from the powdery preparation $CaCO_3$/Pyophage, WoVD (Case 7). The obtained results may be connected with either inactivation of bacteriophages during drying (maybe less in case of freeze-drying) or incomplete desorption of bacteriophages under the used conditions (i.e. desorption with saline solution at room temperature)—the latter appeared to be more likely.

C. Spray Drying

Spray drying conditions Spray drier: NIRO MOBILE MINOR™ (Denmark) equipped with a rotary atomizer Bacteriophages: Serial phages of "Biochimpharm, LLC (Georgia) Staph. a. & E. coli Fillers: $NaHCO_3$, $MgCO_3$, and $CaCO_3$ Filler's concentration, w/v: 8.0%

Pump: Peristaltic

Feed rate: 1.0 L/h

Temperature: on the inlet—90-95° C., on the outlet—50° C.

Protocol of spray drying of liquid phages: 80.0 g of one of the fillers ($NaHCO_3$, $MgCO_3$, or $CaCO_3$) was added to 1.0 L of liquid bacteriophage (Staph. a. or E. coli, serial liquid phages, without purification) and thoroughly stirred. Sodium bicarbonate ($NaHCO_3$) formed a homogeneous solution whereas others ($MgCO_3$ or $CaCO_3$), formed suspensions (all are referred to as bacteriophage/salt mixtures).

In a typical procedure a bacteriophage/salt mixture was supplied to NIRO MOBILE MINOR™ spray-drier equipped with a rotary atomizer via peristaltic pump at a feed rate 1.0 L/h. In case of $MgCO_3$ or $CaCO_3$ bacteriophage/salt mixtures (suspensions) was permanently stirred to avoid the precipitation of the solid (salts). Under these conditions, at the inlet air temperature 90-95° C., the temperature on the outlet was kept at 50° C. that was mild for bacteriophage drying that resulted in powdery preparations. The obtained powdery bacteriophage preparations were subjected to the analysis on bacteriophage content.

Analysis: to determine the bacteriophages content in powdery (dry) preparations. 4.0 g of a powdery phage preparation and 50.0 mL of saline solution were placed in a 250.0 mL flat-bottom flask, sealed with a stopper and shook for 15 min. The flask was removed from a shaker and kept until the solid (in case of $MgCO_3$ or $CaCO_3$; in case of $NaHCO_3$ solution is obtained) precipitated. An aliquot was removed from the $MgCO_3$ or $CaCO_3$ supernatants right after the solid precipitated, or from the $NaHCO_3$ solution for the determination of PFU using the double agar overlay method of Gratia.

Results: the results listed as Case 9, showed that, in terms of PFU of the bacteriophages in the dried products, the best filler appeared to be $CaCO_3$ for which PFU for E. coli was either of the same order as initial PFU (decreased 2.5 times only, Sample #1), or for Staphylococcus aureus decreased by less than two orders (ca. 33 times, Sample #2), followed by $MgCO_3$ (PFU decreased by 25 and 60 times, accordingly, Samples ##3 and 4), and $NaHCO_3$ (PFU decreased by 250 and 15,000 times, Samples ##5 and 6). The latter appeared to be the worst one among the used fillers.

Case 9: Spray drying of liquid bacteriophages in the presence of various filler

| # | Bacteriophage | Filler, w/v % | PFU, initial* | PFU, after drying** (desorbed phages) | PFU, initial PFU, after drying |
|---|---|---|---|---|---|
| 1 | E. coli | $CaCO3$, 8.0 | $5.0 \times 10^8$ | $2.0 \times 10^8$ | 2.5 |
| 2 | Staphylococcus aureus | $CaCO3$, 8.0 | $3.0 \times 10^8$ | $9.0 \times 10^6$ | 33.0 |
| 3 | E. coli | $MgCO3$, 8.0 | $5.0 \times 10^8$ | $2.0 \times 10^7$ | 25.0 |
| 4 | Staphylococcus aureus | $MgCO3$, 8.0 | $3.0 \times 10^8$ | $5.0 \times 10^6$ | 60.0 |
| 5 | E. coli | $NaHCO3$, 8.0 | $5.0 \times 10^8$ | $2.0 \times 10^6$ | 250.0 |
| 6 | Staphylococcus aureus | $NaHCO3$, 8.0 | $3.0 \times 10^8$ | $2.0 \times 10^4$ | 15,000.0 |

*PFU of liquid bacteriophages subjected to spray drying
**PFU of the bacteriophages desorbed form the dried preparations The lower results in case of $MgCO_3$ and $NaHCO_3$ could be connected with increasing the solutions' pH that could cause the bacteriophages inactivation in certain extent (higher in case of $NaHCO_3$). In contrast to $MgCO_3$ and $NaHCO_3$, $CaCO_3$ could be neutral and did not influence the solution's pH. Among the used bacteriophages, E. coli appeared to be less tend to the inactivation under the used conditions than S. aureus, though in case of insoluble salts $MgCO_3$ and $CaCO_3$, the lowering of PFU could also be explained by incomplete desorption of phages.

As a whole, due to the mild drying conditions disclosed, the spray drying with rotary atomizer resulted in bacteriophages survival at either the same or even higher level compared to the spray drying with pulse combustion atomizer, which was contrary to the statement given in US Patent Application Publication Number 2009/0093041 A1, published Apr. 9, 2009, that a rotary atomizer kills bacteriophages owing to the action of sharing stress. The good results obtained with rotary atomizer could be connected with the presence of solid particles that could adsorb shock thus protecting bacteriophages from the inactivation. Much better results (in terms of PFU) obtained after drying with $MgCO_3$ as compared with $NaHCO_3$ could speak for this assumption since the solutions' alkalization level in both cases were very close (pH 9.0-9.5).

Protocol of spray drying of wet solids obtained after Steps 2 or 3. For spray-drying Salt/Bacteriophage,$W_0$ or Salt/Bacteriophage,$W_1$, wet solids should be mixed with saline solutions (1.0 kg of wet solid+3.0 L of saline solution—w/v ratio 1:10 per dry adsorbent) to obtain suspensions that could be supplied (feed) to spray drier. The drying conditions were the same as above (inlet air temperature 90-95° C., the temperature on the outlet was kept at 50° C.; feed rate 1.0 L/h). In this case the obtained dry powdery preparations contained NaCl (27 g that came from 3.0 L of saline solution).

In one example, a powdery salt with immobilized Pyophage was prepared (1:10 w/v ratio) by adding 10.0 L of liquid bacteriophage with an activity of $10^8$-$10^9$ PFU (plaque forming units) to 1.0 kg of medical grade calcium carbonate $CaCO_3$ with an average particle size of 50 µm at room temperature. The mixture of calcium carbonate and bacteriophage was thoroughly homogenized by stirring for 20-30 minutes. After cessation of stirring, the mixture was incubated at room temperature for 30 min without agitation. The suspension was then filtered off to obtain separated wet solid and filtrate. The wet solid was dried by either vacuum drying at 40-45° C. over a water adsorbent material (anhydrous $CaCl_2$ or $Na_2SO_4$, or silica gel), freeze-drying, or spray drying as disclosed above.

The resulting dried powder comprised calcium carbonate with immobilized bacteriophages. A powder of medical grade magnesium carbonate with an average particle size of 200 μm was added to the dried powder at a weight ratio of 5/95 ($MgCO_3/CaCO_3$) and thoroughly homogenized. The obtained mixture was labeled as $(Ca_{95}Mg_5)CO_3$/Bacteriophage.

Example 5: Preparation of the Second Composition

To a 8 L solution containing 0.6 kg of the poly (ester urea amide) prepared above was added 0.6 kg of $(Ca_{95}Mg_5)CO_3$/bacteriophage. The resulting solution was thoroughly homogenized. To the resulting polymer/bacteriophage suspension, 0.1 kg of benzocaine (or lidocaine), 0.07 kg of ciprofloxacin, and 0.007 kg α-chymotrypsin were added and thoroughly homogenized again.

The obtained mixture was poured onto a hydrophobic surface (Teflon® dishes (25×26 cm×cm)) and the chloroform was completely evaporated at room temperature under atmospheric pressure. The films were then dried at 40° C. under reduced pressure for 24 hr. The films were removed from the hydrophobic surface, perforated, and packed. See FIG. 4 for illustrative purpose of the perforated films.

Alternatively, serial liquid phages may be used for preparing the second composition. A solution of the poly(ester urea amide) prepared as described above and liquid phage are mixed vigorously until the formation of fine emulsion. Different ingredients such as various Ca and Mg salts or other salts, as well as various bioactive agents can be added to this emulsion. The obtained emulsion is then cast onto a hydrophobic surface, quickly frozen, and subjected to freeze-drying. The films are removed from the hydrophobic base, perforated, and packed.

When grindable poly (ester urea), i.e., LMW-1L6, replaced poly (ester urea amide) to prepare the second composition, the film formed after the evaporation of organic solvent (chloroform, dichloromethane) was brittle. The film was grinded into a fine powder and sieved through the sieve of the desirable mesh-size that can result in microparticles suitable for the application in spray wound dressing.

Example 6: Preparation of a Poly(Ester Urea Amide) $(1L6)_{0.6}$-$(8L6)_{0.4}$

The homo-poly(ester amide) 8L6 composed of L-leucine (L), 1,6-hexanediol (6) and sebacic acids (8), obtained by interfacial polycondensation (IP) of L6 with sebacoyl chloride, may be used for preparing bacteriophage-containing compositions. However, due to its amorphous nature and low glass transition temperature $T_g$ of 37° C. (as described in R. Katsarava, V. Beridze, N. Arabuli, D. Kharadze, C. C. Chu, C. Y. Won. Amino acid based bioanalogous polymers. Synthesis and study of regular poly(ester amide)s based on bis(α-amino acid) α,ω-alkylene diesters and aliphatic dicarboxylic acids. *J. Polym. Sci.: Part A: Polym. Chem.* 37, 391-407 (1999).), 8L6 is too pliable and sticky for many applications. To reduce pliability and stickiness, 8L6 could be modified to contain some relatively rigid fragments to increase $T_g$. In the present example, more rigid fragments of poly(ester urea), composed of L-leucine, 1,6-hexanediol and carbonic acid, referred to herein as 1L6, were incorporated into the poly(ester amide)'s 8L6 backbone. The increase rigidity of the poly(ester urea) fragments may be attributed to their dense intermolecular hydrogen bond networks.

To incorporate poly(ester amide) fragments into the 8L6 backbone, at least one sebacic acid is replaced by at least one carbonic acid in the polymeric backbone. Replacing sebacic acid in the polymeric backbone with carbonic acid may increase the $T_g$ up to 60° C.

In one example, due to the distribution of poly(ester amide) and poly(ester urea) blocks in its backbone, the product poly(ester urea amide) may be labelled $(1L6)_{0.6}$-$(8L6)_{0.4}$. The product poly(ester urea amide) is synthesized by interfacial polycondensation of di-p-toluenesulfonic acid salts of bis-(L-leucine)-1,6-hexylene diester with a mixture of sebacoyl chloride/triphosgene at 60/(40:3) mole/mole ratio. A two phase system dichloromethane/water is used to carry out the interfacial polycondensation, which may be completed in as little as 15 to 20 min. Sodium carbonate is also added to the mixture to catch the byproducts p-toluenesulfonic acid, which comes from amino acid based monomer, and hydrogen chloride, which is produced by the interaction of acid chlorides with primary amino groups. These byproducts are highly water soluble and are retained in the water phase as well as in the excess of sodium carbonate. Following the interfacial synthesis, the target polymer is retained in the organic (dichloromethane) phase. After washing with water, the target polymer in solution may be be used for preparing second compositions described herein without separating the target polymer. Advantageously, dichloromethane is less toxic that many other organic solvents commonly used to synthesize polymers similar to the present example. For example, dichloromethane is considered to be about 10 times less toxic than chloroform.

The amino acid based monomer used in the synthesis described above (di-p-toluenesulfonic acid salts of bis-(L-leucine)-1,6-hexylene dieste) may be prepared by direct condensation of 2.0 moles of L-leucine with 1.0 mole of 1,6-hexanediol in the presence of 2.1 moles of p-toluenesulfonic acid monohydrate in refluxed cyclohexane. Cyclohexane is less toxic than benzene and toluene, two organics solvents used in alternative processes for prearing amino acid based monomers. Another monomer used in the interfacial synthesis is sebacoyl chloride, a readily purchasable product, which facilitates the preparation of the target polymer. In the present example, sebacoyl chloride is used directly for synthesizing the target polymer. Moreover, in the present example, a part of the sebacoyl chloride is substituted by the less expensive triphosgene, making the preparation of the target polymer more cost effective than the synthesis of some alternative amino acid based polymers. Moreover, in contrast to some previously prepared amino acid based polymers, the target polymer does not contain L-phenylalanine. The presence of L-phenylalanine in a polymer may led to adverse events in patients suffering from phenylketonuria.

Example 7: Alternative Preparations of Powdery Bacteriophages (the First Composition)

A. Powdery Salts

Powdery salts with immobilized bacteriophages were prepared by the incubation of at least one salt in a liquid preparation of at least one bacteriophage and subsequent drying using vacuum-drying or freeze-drying.

In one instance, 50.0 g of $CaCO_3$ is added to a 250 mL Erlenmeyer flask though a funnel, followed by the addition of 50 mL of liquid bacteriophage in TMN (Tris-MgCl$_2$—NaCl) buffer to the flask. A Teflon magnetic stirring bar (l=5-6 cm) is placed in the flask containing the mixture, and the flask is then sealed and its contents stirred using a magnetic stirrer for 1.0 hr.

After 1.0 hr, stirring is stopped, the flask is opened, and the contents of the flask are transferred to a porous glass filter. The contents are filtered under reduced pressure, and the resulting wet solid is transferred to a glass vessel using a spatula. The non-sealed glass vessel is placed in a vacuum drier containing a pan with 200 mg anhydrous sodium sulfate (CAS number: 7757-82-6). The wet solid is then dried under pressure at 40° C. or less for 5 hours. Following removal of the vacuum, the glass vessel is removed from the freeze-drier and sealed. The sealed glass vessel containing the powdery salts with immobilized bacteriophages is stored at 4° C. until use.

In another instance, 50.0 g of CaCO$_3$ and 50 mL of liquid bacteriophage in TMN (Tris-MgCl$_2$—NaCl) buffer are placed in a 250 mL round bottom flask. The flask is placed on a rotary evaporator with a joint of the same size as the round bottom flask and rotated without vacuum for 1.0 hr. A vacuum is then applied to the rotary evaporator, and the contents of the flask are dried at 40° C. until dry solid is formed based on visual inspection. Vacuum is removed, and the round bottom flask is removed from the rotary evaporator. The dried product is moved to a sterile vessel, and the mass of the product is determined after sealing of the vessel. The expected mass of the product is 51.3 g.

The sealed vessel containing the powdery salts with immobilized bacteriophages is stored at 4° C. until use.

Sterile, medical grade CaCO$_3$ with a mean particle size of 6-8 μm is used to prepare the powdery salts with immobilized bacteriophages.

B. Freeze-Dried Bacteriophage Compositions

In one instance, 10 mL of liquid bacteriophage (10$^9$ to 10$^{10}$ PFU/mL) in TMN buffer is freeze-dried to prepare freeze-dried TMN buffer with incrusted (impregnated) bacteriophages.

Before freeze drying the liquid bacteriophage in TMN, the freeze-drier is switched on, all stopcock are closed, and a vacuum is applied. The rubber joint of the freeze-drier is cleaned using a sterilizing liquid such as chloroform prior to use.

10 mL of liquid bacteriophage in TMN is transferred to a 100 mL flask. The flask is closed with a stopper and transferred to a cooling bath (−10 to −15° C.). The stopper is loosened on the cooled 100 mL flask, which is placed on the freeze-drier after equilibrating to −10° C. to −15° C. The stopcock on the freeze-drier is then opened, and a vacuum is applied to the flask. The contents of the flask are lyophilized on the freeze-drier until a white crystalline powder forms.

After a white crystalline powder is formed, the vacuum is removed, and the flask is removed from the freeze-drier. The mass of the product is determined, and the freeze-dried powdery bacteriophage is stored in a sealed container at 4° C.

Powdery bacteriophage without salt may be prepared by dialyzing the liquid bacteriophage in TMN in water prior to cooling and freeze-drying the liquid bacteriophage.

C. Alternative Analysis Procedure

To determine the bacteriophages content in powdery (dry) preparations. 1.0 g of a powdery phage preparation and 1.0 mL of saline solution are placed in a test tube, sealed with a cap and shook for 30 min in alaboratory shaker. The test tube was removed from a shaker and centrifuged at 3000 rpm for 15 min. An aliquot is removed from supernatant after centrifugation for the determination of PFU using the double agar overlay method of Gratia.

Powdery bacteriophage compositions prepared by the procedures above are non-immunogenic. In addition, powdery water insoluble carbonate salts with immobilized bacteriophages may protect the bacteriophages when the first composition is used in the treatment of a wound with increased acidity (acidosis).

Example 8: Preparation of the Second Composition

A 4 mL solution containing 13% w/v of poly (ester urea amide) in dichloromethane was poured into a cylindrical sterile glass vessel containing 30 to 35 mg of freeze-dried bacteriophage. The poly(ester urea amide) was prepared as in Examples 3 or 6 above, and the freeze-dried bacteriophages were prepared as described in Example 7. The resulting solution was thoroughly homogenized at a speed to 100 rpm or lower to avoid splashing.

The obtained mixture was poured onto a hydrophobic surface (a sterile Teflon® dish) and the dichloromethane was evaporated at room temperature under atmospheric pressure for 4 days. The films were then dried at 37° C. under reduced pressure until the film reached a constant weight.

Dry films were stored at 4° C. until further use.

Example 9: Preparation of the Biodegradable Poly(Ester Urea)

This example shows how a poly(ester urea) as described above may be prepared. 183.94 g (0.267 mol) of di-p-toluenesulfonic acid salt of bis(L-leucine)-1,6-hexylene diester, L6 (M=688.91), 26.41 g (0.267/3=0.089 mole) of triphosgene (M=296.748 g/mol) Bis-electrophile, 0.267 mol, 84.667 g of anhydrous sodium carbonate (0.8 mol), 0.8 L of amylene-stabilized dichloromethane, 1.6 L of distilled water and 100 g anhydrous sodium sulfate were measured. The bis-electrophilic monomer—di-p-toluenesulfonic acid salt of bis(L-leucine)-1,6-hexylene diester, anhydrous sodium carbonate, and distilled water were combines and stirred until complete dissolution of the ingredients (this takes about 30-40 min). This creates a first solution. Afterwards, the bis-nucleophilic monomer—triphosgene and 0.8 L of amylene-stabilized dichloromethane were mixed until a homogeneous solution is formed. This creates a second solution. The second solution is then mixed into the first solution and stirred, following which stirring is stop to allow a two phase system to clearly form. The goal polymer is dissolved DCM, which represents the lower layer. The upper layer is water with dissolved in it carbonate salts and by-products of the polycondensation (i.e. polymer synthesis) such as sodium chloride (NaCl) and sodium p-toluenesulfonate (NaOTos). This upper layer is removed and thrown away. A first wash is performed by adding to the container containing DCM layer with the dissolved polymer 2.0 L of a fresh portion of distilled water. The mixtured is then mixed again, for example using a stirrer at 100-200 rpm for 30 min. Once again, the resulting mixture is left still until a two phase system is clearly formed and the water phase is removed. Additional similar washes, for example 5 total washes, may also be performed. The DCM layer with dissolved polymer may still contains some water, which can be extracted using the anhydrous sodium sulfate. The resulting DCM solution includes the desired polymer.

Example 10: Preparation of the Biodegradable Poly(Ester Urethane Urea)

This example shows how a poly(ester urethane urea) as described above may be prepared. A copolymer—poly(ester urethane urea), PEURU, $(D6L6)_{0.20n}$-$(1L6)_{0.80n}$, where D6 means the residue of 1,6-hexanediol in ester-urethane blocks—comes from 1,6-hexamethylene bis(chloroformate), 1—the residue of carbonic acid in ester-urea blocks—comes from phosgene (triphosgene) is prepared as follows. The following is prepared: 183.94 g (0.267 mol) of di-p-toluenesulfonic acid salt of bis(L-leucine)-1,6-hexylene diester, L6 (M=688.91); 12.883 g (0.053 mol) of 1,6-Hexamethylene bis(chloroformate) (M=243.08 g/mol); 21.158 g (0.214/3=0.0713 mole) of triphosgene (M=296.748 g/mol Bis-electrophiles—0.053+0.214=0.267 mol; 84.667 g of anhydrous sodium carbonate (0.8 mol); 0.8 L of amylene-stabilized dichloromethane; 1.6 L of distilled water and 100 g anhydrous sodium sulfate. Then, the bis-electrophilic monomer—di-p-toluenesulfonic acid salt of bis(L-leucine)-1,6-hexylene diester, anhydrous sodium carbonate, and distilled water are combined and stirred at room temperature until complete dissolution of the ingredients. This forms a first solution. The bis-nucleophilic monomers—1,6-hexamethylene bis(chloroformate) and triphosgene are then combined and 0.8 L of amylene-stabilized dichloromethane is added, further to which stirring is performed until a homogeneous solution is formed. This forms a second solution. The second solution is then added slowly to the first solution while the latter is stirred, following which the resulting mixture is stirred until the polymerisation reaction is complete, for example an additional 15-20 min. Then, the water and DCM phases are left to separate, the water phase is removed, and multiple washes following by drying are performed as in example 9.

Example 11: Preparation of the Biodegradable Poly(Ester Amide Urethane)

This example shows how a poly(ester amide urethane) as described above may be prepared: PEAUR, $(8L6)_{0.90n}$-$(D6L6)_{0.10n}$, where 8 means the residue of sebacic acid in ester amide block—comes from sebacoyl chloride, D6—the residue of 1,6-hexanediol in ester-urethane blocks—comes from 1,6-hexamethylene bis(chloroformate). The following is prepared: 183.94 g (0.267 mol) of di-p-toluenesulfonic acid salt of bis(L-leucine)-1,6-hexylene diester, L6 (M=688.91); 57.47 g (0.267·0.9) 0.2403 mol of sebacoyl chloride (M=239.14 g/mol); 6.49 g (0.267·0.1)=0.0267 mol of 1,6-hexamethylene bis(chloroformate) (M=243.08 g/mol) Bis-electrophiles—0.2403+0.0267=0.267 mol; 84.667 g of anhydrous sodium carbonate (0.8 mol); 0.8 L of amylene-stabilized dichloromethane; 1.6 L of distilled water; 100 g anhydrous sodium sulfate. The bis-electrophilic monomer—di-p-toluenesulfonic acid salt of bis(L-leucine)-1,6-hexylene diester, anhydrous sodium carbonate, and distilled water are combined and stirred at room temperature until complete dissolution of the ingredients. This forms a first solution. Then, the bis-nucleophilic monomers—sebacoyl chloride and 1,6-hexamethylene bis(chloroformate) are mixed and 0.8 L of amylene-stabilized dichloromethane is added and stirring is performed unto a homogeneous solution is formed, further to which stirring is performed until a homogeneous solution is formed. This forms a second solution. The second solution is then added slowly to the first solution while the latter is stirred, following which the resulting mixture is stirred until the polymerisation reaction is complete, for example an additional 15-20 min. Then, the water and DCM phases are left to separate, the water phase is removed, and multiple washes following by drying are performed as in example 9.

Example 12: Preparation of the Biodegradable Poly(Ester Urethane)

This example shows how a poly(ester urethane) as described above may be prepared: poly(ester urethane), PEUR, D6L6, where D6 means the residue of 1,6-hexanediol in ester-urethane blocks—comes from 1,6-hexamethylene bis(chloroformate). The following is prepared: 183.94 g (0.267 mol) of di-p-toluenesulfonic acid salt of bis(L-leucine)-1,6-hexylene diester, L6 (M=688.91); 64.9 g (0.267 mol) of 1,6-hexamethylene bis(chloroformate) (M=243.08 g/mol) Bis-electrophile—0.267 mol; 84.667 g of anhydrous sodium carbonate (0.8 mol); 0.8 L of amylene-stabilized dichloromethane; 1.6 L of distilled water 100 g anhydrous sodium sulfate. The bis-electrophilic monomer—di-p-toluenesulfonic acid salt of bis(L-leucine)-1,6-hexylene diester, anhydrous sodium carbonate, and distilled water are combined and stirred until complete dissolution of the ingredients. This forms a first solution. Then, the bis-nucleophilic monomer—1,6-hexamethylene bis(chloroformate) is mixed with 0.8 L of amylene-stabilized dichloromethane, further to which stirring is performed until a homogeneous solution is formed. This forms a second solution. The second solution is then added slowly to the first solution while the latter is stirred, following which the resulting mixture is stirred until the polymerisation reaction is complete, for example an additional 15-20 min. Then, the water and DCM phases are left to separate, the water phase is removed, and multiple washes following by drying are performed as in example 9. Put magnetic bar (4 cm of length) into the flask and seal the flask with the glass stopper. Put the flask on a magnetic stirrer at r.t. and stir until a homogeneous solution is formed.

Example 13: Preparation of the Biodegradable Poly(Ester Amide Urethane Urea)

This example shows how a poly(ester amide urethane urea) as described above may be prepared: poly(ester amide urethane urea), PEAURU, $(8L6)_{0.50n}$-$(D6L6)_{0.10n}$-$(1L6)_{0.40n}$, where 8 means the residue of sebacic acid in ester amide block—comes from sebacoyl chlioride, D6—the residue of 1,6-hexanediol in ester-urethane blocks—comes from 1,6-hexamethylene bis(chloroformate), 1—residue of carbonic acid in ester-urea blocks—comes from phosgene (triphosgene). The following is prepared: 183.94 g (0.267 mol) of di-p-toluenesulfonic acid salt of bis(L-leucine)-1,6-hexylene diester, L6 (M=688.91); 31.93 g (0.267·0.5) 0.1335 mol of sebacoyl chloride (M=239.14 g/mol); 6.49 g (0.267·0.1) 0.0267 mol of 1,6-hexamethylene bis(chloroformate) (M=243.08 g/mol); 10.564 g (0.267·0.4)/3=0.1068/3) 0.0356 mol of triphosgene (M=296.748 g/mol) Bis-electrophiles—0.1335+0.0267+0.1068=0.267 mol; 84.667 g of anhydrous sodium carbonate (0.8 mol); 0.8 L of amylene-stabilized dichloromethane; 1.6 L of distilled water and 100 g anhydrous sodium sulfate.The bis-electrophilic monomer—di-p-toluenesulfonic acid salt of bis(L-leucine)-1,6-hexylene diester, anhydrous sodium carbonate, and distilled water are combined and mixed an triphosgene triphosgene at room temperature until complete dissolution of the ingredients. This forms a first solution. Then, the bis-nucleophilic monomers—sebacoyl chloride, 1,6-hexamethylene bis (chloroformate) and triphosgene are mixed and 0.8 L of amylene-stabilized dichloromethane is added, further to which stirring is performed until a homogeneous solution is formed. This forms a second solution. The second solution is then added slowly to the first solution while the latter is stirred, following which the resulting mixture is stirred until the polymerisation reaction is complete, for example an additional 15-20 min. Then, the water and DCM phases are left to separate, the water phase is removed, and multiple washes following by drying are performed as in example 9.

Stirring durations are similar in examples 9 to 14 to the example relating to PEAU synthesis described above.

Example 14: Alternative Preparation of the Biodegradable Poly(Ester Amide Urea)

This example shows how a poly(ester urethane) as described above may be prepared in a manner that has been optimized with respect to the synthesis method described above. Di-p-toluenesulfonic acid salt of bis(L-leucine)-1,6-hexylene diester (2 kg, 2.9 mol) was added to a reactor suitable for interfacial polycondensation. Water (9.5 L) was added to the reactor with stirring. To the obtained suspension, anhydrous sodium carbonate (0.920 kg, 8.7 mol) was added and stirred at room temperature for approximately 30-40 min (the first solution). In a separate vessel, tri-phosgene (0.116 kg, 1.2/3 mol) and sebacoyl chloride (i.e., ClCO—(CH)—COCl, 0.400 kg, 1.7 mol) were dissolved in (6.3 L) of amylene stabilized (dichloromethane (DCM)) (the second solution). The second solution was rapidly added to the first solution at room temperature to produce a water/organic mixture. The water/organic mixture was stirred vigorously for about 15-20 min. Following cessation of stirring, the mixture was allowed to separate completely, resulting in a two-layer system. The lower layer containing poly(ester urea amide) in dichloromethane was separated and washed 2 times (2×5.3 L) with distilled water to remove the salts (sodium chloride, sodium carbonate/bicarbonate, and sodium p-toluene-sulfonate). To the organic layer, 7 kg of brine and 6 L of dichloromethane were added. The dichloromethane layer was separated after each wash step and aqueous top layer was discarded. After 3 hours of the phase separation, the rag layer with aqueous layer was kept and washed with additional 100 mL dichloromethane. After washing, the (dichloromethane) layer was separated again, dried over anhydrous $Na_2SO_4$ (2 kg), and filtered off. The solution was poured in a non-stick metal pan under a heat lamp in the chemical fume hood and was dried until it is no longer tacky (typically 1-2 days). Then, it was dried under vacuum in a Pyrex dish until constant weight (30° C.). Putting the sheet of polymer over parchment paper allows it to dry (and soften) while avoiding sticking to the bottom of the Pyrex dishes. Dichloromethane is considered a relatively safer solvent than chloroform to be used in large scale production of polymers. Moreover, it provides good solubility to the product of interest and it is not miscible with water, which facilities purification processes. The molar concentration of reagents are different in the two methods. Higher reagent concentration leads to the formation of polymer with higher molecular weight, which was observed in laboratory scale by viscosity measurement.

This PEAU can also be used, as the above-described one, to prepare patches or films including bacteriophages dispersed therein by simply mixing the bacteriophages (for example liophilized or adsorbed on salts or other inorganic particles) in the polymer containing DCM, with the addition of any additional patch or film substance that one may want to include, and casting the resulting liquid. In some embodiments, the resulting solution spread on a large surface is left standing until most of the DCM evaporates, and drying is completed in vacuum.

Films for the Treatment and Prevention of Infection in Wounds.

The PEAU polymer, along with the other polymers described in the present application, may be used in a method of treating, reducing or preventing bacterial infection in a wound, the method comprising: applying a film on the wound, the film including a biodegradable polymer (PEAU or the other polymers described in the present application) with bacteriophages dispersed therein. PEAU has been found to be particularly advantageous as it has mechanical properties allowing manufacturing relatively thin films, for example between 100 μm and 1 mm thick, especially when the protocol of example 14 is used to manufacture the film. The film is flexible, meaning that it can conform to the shape of the part of the human body on which it is applied. The film is typically solid when applied, but can be in some embodiments wet.

In some embodiments, the film further includes salt particles dispersed in the polymer, for example $CaCO_3$ particles. The film may further include a buffer, for example TNM, to provide a better environment to the bacteriophages. Additional bactericides, such as, and non-limitingly, antibiotics silversulfadiazine, silver nitrate or nanocrystalline silver may also be either added to the film, or applied to the wound prior to application of the claimed film. The proposed treatment has been observed in vitro to be efficient to reduce bacterial load in antibiotic-resistant bacteria. Also, a synergistic effect has been observed on some bacterial strain between the proposed films including bacteriophages and silver containing products. Surprisingly, the combination of a silver cream component and the proposed film was seen in some embodiments to reduce bacterial load with a much larger efficiency than would be presumed from results obtained with either the silver component or bacteriophages.

The proposed film is relatively thin and designed to be replaced after some time if needed. The proposed film is gradually dissolved by wound exudate, based on one or more of the volume of wound exudate produced and the quantity of cell lysis enzymes naturally present in the wound exudate. Adjustment of the film thickness, molecular weight and salt content allows adjusting the duration over which the film releases the bacteriophages in the wound. For example, each film is applied for a duration of between 1 and 45 days, and in some embodiments for a duration of between 3 and 7 days. After the film is worn down to a significant degree or has disappeared altogether, a new film may be applied to the wound as needed.

Of note, due to its relatively small thickness and to the material used, the film is visually unobtrusive and may even allow visual monitoring of the wound without removing the film, which may be useful in a clinical setting and improve patient comfort as it eliminates repeated removal of the film for inspection. For example, the film is substantially transparent when wet so that light diffusion by the film is very small or non-existant. In a specific example, 95%, 97% or 99% or more of the light going through the film is neither absorbed, reflected nor diffused, or is other words, transmitted in a straight line, according to geometric optics. The patent office image processing system would not allow showing such details in a picture, but films according to the invention have been produced, which, when applied to the skin, still allowed to see hair, veins (as appearing trough the skin), pores and other skin surface details almost unaffected by the presence of the film, even using magnification. Application on wounds also clearly allowed to see wound details, such as redness caused by inflammation and wound depth. All these desired optical properties are achievable while having desirable bacteriophage load in the film and suitable mechanical properties.

In some embodiments, the bacteriophages are delivered in two phases. A first phase, immediately after the film is applied, results in fast (for example 2 hours or less or 4 hours or less) delivery of a predetermined fraction of the bacteriophages. Such delivery is either produced by having a coating of bacteriophages on the film, or by having a film that is porous enough to lead to rapid delivery of bacteriophages close to the surface of the film. This delivery may deliver between 10 and 90 percent of the film's bacteriophage load, or even more if bacteriophages are present on the surface of the film, rapidly and allows to rapidly treat an already present infection efficiently. Afterwards, the remaining bacteriophages are released at a smaller rate, which helps in completing elimination of the infection and in preventing further infections. Of note, the film also forms a physical barrier on the skin that prevents or reduces external contamination. In some embodiments, although the film itself is non-porous, the film is thin enough to allow diffusion of oxygen therethrough, which further helps in wound healing by reducing the likelihood of infection by anaerobic bacteria.

Gradual liberation of bacteriophages in the second phase is regulated by the needs of the patient. Indeed, infections typically result in larger volumes of exudates (which dissolves the salts) and the presence of enzymes (which degrade the matrix), such as elastase and metalloproteinases, in the exudate. As these components of the exudate reach the film in larger quantities, the film releases larger quantities of bacteriophages. To the contrary, if infection is well-controlled, the volume of exudate is small and the relatively thin film may be preserved intact for a longer duration. In some embodiments, a suitable enzyme, such as the enzymes mentioned in this paragraph, is also added in small quantity to the film to provide a slow controlled degradation of the film even in the absence of infection, to act prophylactically.

The proposed film is typically non-woven and non-porous and includes a relatively large bacteriophage load, for example 500,000 PFU/cm^2 or more, which is significant given the relatively small thickness of the film. The proposed film is suitable for the treatment of any wound, and may also be used in some embodiments in surgery inside the body. In such applications, the film would be left inside the body after the surgery is completed to prevent infections. Due to its small size, the film would then disappear relatively quickly to let the natural healing process occur in the patient. Such an application may be useful in contexts in which surgery must be performed in an environment in which sterility is difficult to achieve, such as during military operations, when far from civilization or even during space flight.

The proposed film is also well suited to the treatment of deep wounds, such as pressure ulcers and burn wound, which are traditionally difficult to treat.

Example 15: Animal Studies Showing Synergy Between Silver Compounds and Bacteriophages Exploratory studies were performed to get indicative data pertaining to the safety and efficacy of the an SPK cocktail (including bacteriophages specific to (*P. aeruginosa, S. aureus*, and *K. pneumoniae*) in a murine full thickness infection model. The first study conducted aimed at assessing the in vivo safety of the phage cocktail and provide an indicative dosage for the mouse injury infection model. The Animal host is the CD-1 mice, 6-8 week of age, rendered neutropenic by cyclophosphamide. (5 mice per group were studied. The bacterial strain used is *Klebsiella pneumonia* ATCC 43816. Bacterial challenge was topical application of $1.48 \times 10^5$ CFU/mouse and the test article was a Phagelux phage cocktail SPK, with a total titer of $1.53 \times 10^{10}$ PFU/ml; 1× strength is defined as 1.00E+08 PFU/mice. Treatment regimen was 10 µL topical administration at 0.5, 24, 48, and 72 h post infection. No signs of animal distress, body weight changes, or toxicity were found following repeated topical applications (SPK control group) or subcutaneous injections (SPK quality control group) of the SPK cocktail at 0.5, 24, 48, and 72 hours. All animals in all control group survived. No significant differences in body weight change were found between the two non-injured control groups (i.e. Health control and SPK quality control). No significant differences in wound index were found between the injured control groups (i.e. Injury control and SPK control). Survival curves show that all mice died 2 days post infection for the vehicle control group while SPK cocktail effectively delayed systemic infection and mice death in a dose-dependent fashion, with higher concentration of the SPK cocktail being more effective. For the 1× concentration (SPK 10 log PFU/mL), mice death (96 h; p.i) was observed only following the end of the treatment (72 h).

Survival curves show that treatment with silver sulfadiazine alone could not effectively delay systemic infection with all mice dying on day 3 post-infection for both the infection control and the silver sulfadiazine group. Co-treatment with phage cocktail and silver sulfadiazine was superior to silver sulfadiazine standard of care alone, and effectively delayed mice death due to systemic infection.

A second study was carried where the mouse injury model of bacterial infection was used to evaluate the in vivo efficacy of phage cocktail SPK in preventing mortality for a bis in die dosing regimen. Bacterial challenge was topical application of $4.83 \times 10^4$ CFU/mouse. Challenge concentration was reduced in an effort to delay death in the infection group and monitor mice survival for alonger period. The test article was Phagelux phage cocktail SPK, of a total titer of $1.53 \times 10^{10}$ PFU/ml; 1× strength is defined as $1.00\lambda 10^8$ PFU/mice. Treatment regimen was 10 µL topical administration twice daily for 5 days p.i. Survival curves show that administration of the SPK cocktail twice daily effectively delayed systemic infection and rescued mice for a 1E+10 PFU/mL concentration. Only one mice died 3 days post infection for the SPK 1× group when compared to all 5 mice dying 3 days p.i. for the infection control group. $10^{10}$ PFU/mL was more $10^9$ PFU/mL. Administration of the cocktail twice daily was more effective than once daily. Mice treated with SPK cocktail were able to recover their body weight when compared to the infection control group. Bacterial burdens in major organs and wound sites were assessed post mortem for all animals in the infection control and SPK 1× treatment groups. Bacterial burdens were significantly lower in surviving mice from the group treated with the SPK cocktail when compared to the Infection control group. SPK cocktail is effective in resolving the systemic bacterial infection.

Phages are self-replicating antibacterial agents, because the phage titer increases at the infection site until the bacterial host is present and efficient concentration may be achieved at exact body/tissue location where it is needed. For systemic administrations, bacteriophages are known to be rapidly eliminated from the systemic circulation by reticuloendothelial system clearance (innate immune mechanisms), then accumulated in spleen and liver or/and inactivated by adaptive immune defense mechanisms involving immunoglobulin in the case of repetitive application. In our hands, we saw high phage concentrations at the wound site for all treatments presented, but very low concentrations of phages in the kidney, spleen, and liver of mice that were either rescued by the phage treatment or for which phage treatment delayed the systemic infection.

Example 16: In-Vitro Studies Showing Synergy Between Silver Compounds and Bacteriophages Silver nanoparticles were extracted from commercially available Silverlon™ patches. Various bacteria were cultured in cell wells in the presence of one or more of an antibiotic, silver nanoparticles and bacteriophages, along with control experiments. More specifically, silver nanoparticles were extracted from 10 cm² of Silverlon in 5 mL of TSB media at 37° C. for 4 h. *A. baumannii. K. pneumoniae, P. aeruginosa, S. aureus* and *B. anthracis* specific-strain bacteriophage cocktails were prepared and the following conditions were investigated in standard 96 wells plate (8 replicate for each group): Column 1: 200 µL of TSB (Tryptic soy broth); Column 2: 100 µL of TSB; Column 3: 50 µL of silver extract+50 µL of TSB; Column 4: 50 µL of strain-specific phage cocktail+50 µL of TSB; Column 5: 50 µL of silver extract+50 µL of strain-specific phage cocktail; Column 6: 50 µL of 2× antibiotic 1 (for which bacteria is sensitive)+50 µL of TSB; Column 7: 50 µL of 2× antibiotic 2 (for which bacteria is resistant)+50 µL of TSB. Then, a 1.5 mL tube containing 500 µL of TSB+250 µL of phage cocktail+250 µL of silver extract was prepared.

Figure 6B:
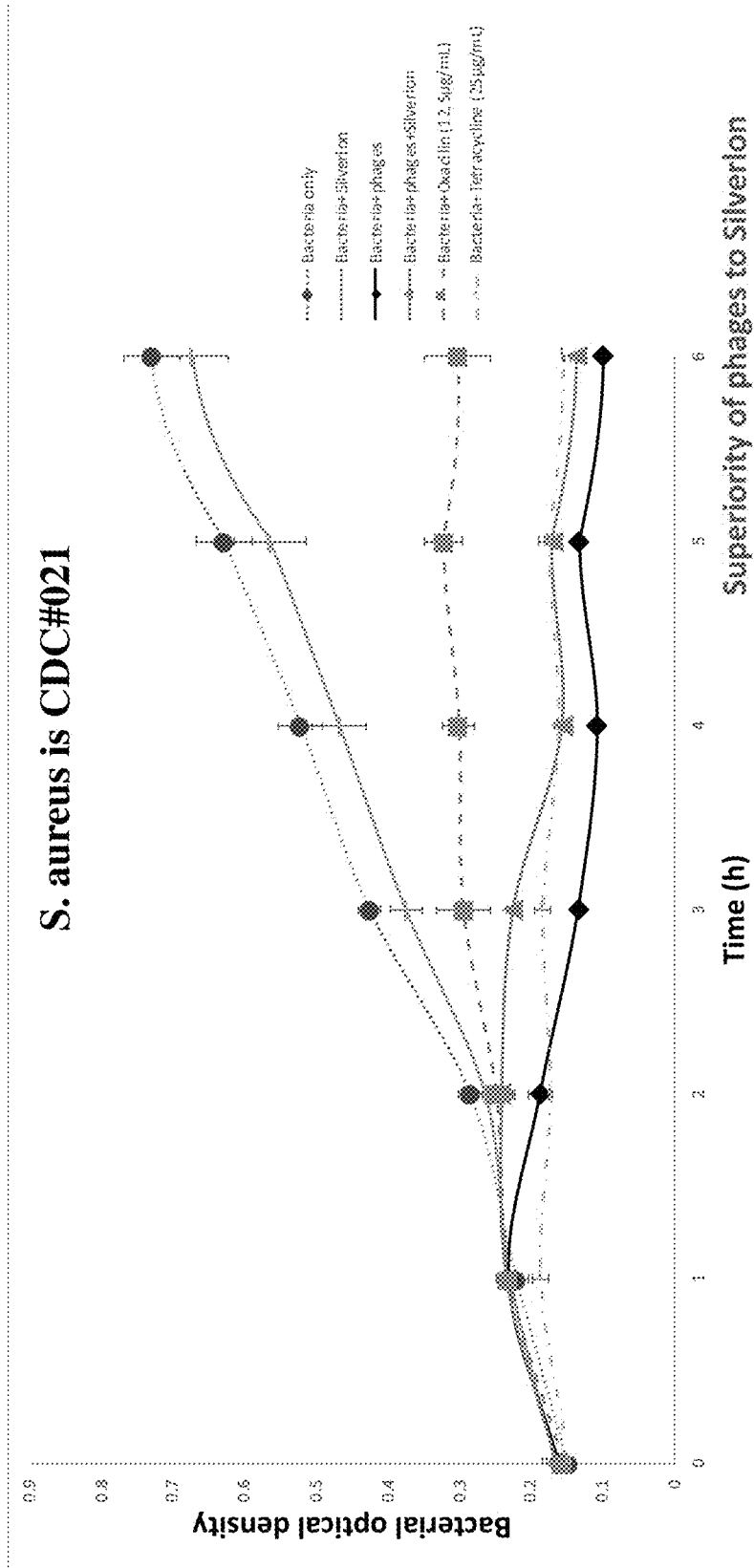
Figure 6C:
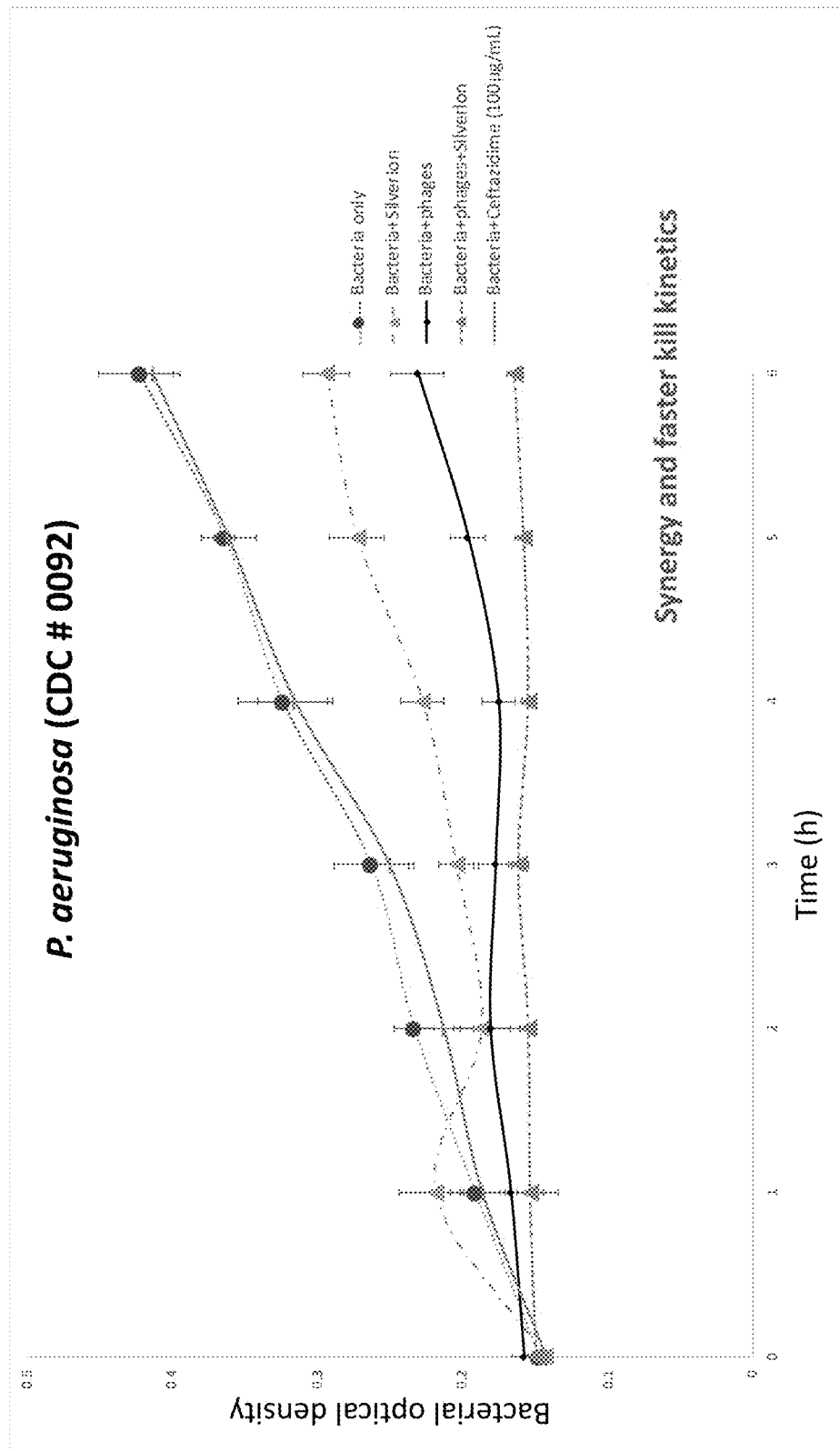
Figure 6D:
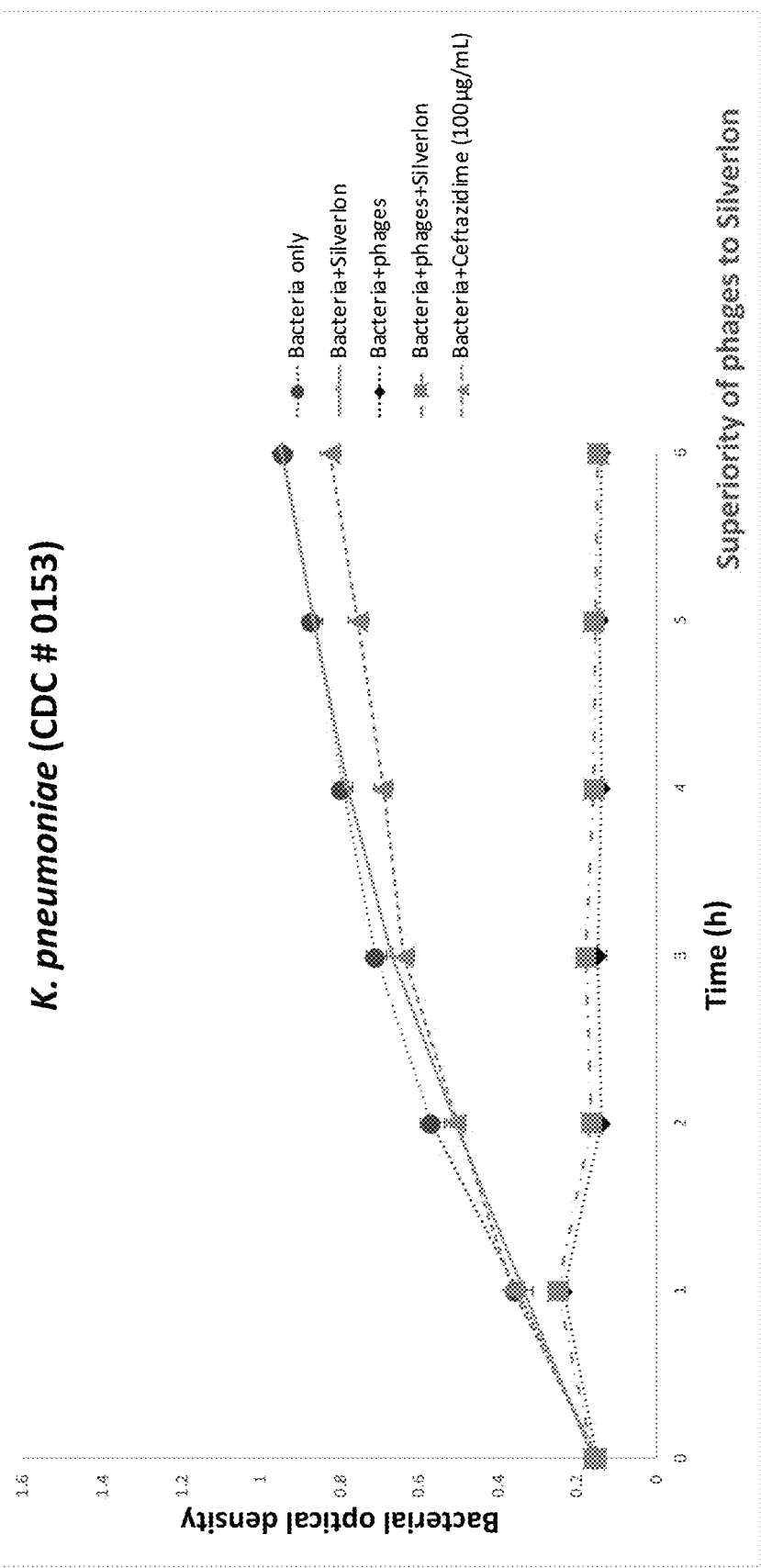
Figure 7:
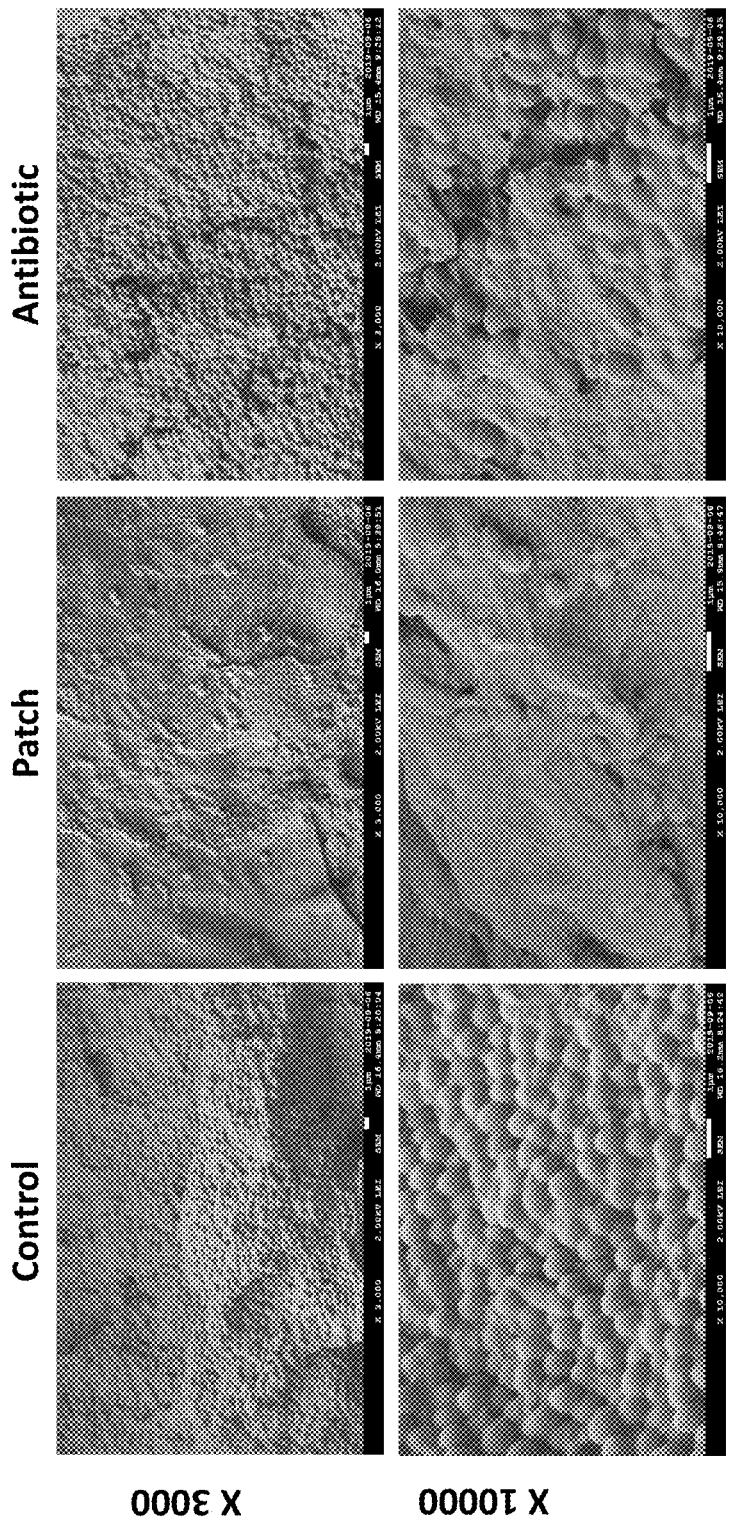
FIG. 7 illustrates the effect of a proposed film including bacteriophage on bacterial growth in wound analogs in vitro.

Bacteria were cultured to reach OD 0.5 and diluted to OD 0.2. 100 µL of bacteria suspension was added in columns 2 to 7, and the plates and 1.5 mL tube were incubated at 37° C. Absorbance at 600 nm was read at the following time-points: 0, 1, 2, 3, 4, 5, 6 h. At each timepoint, 100 µL was removed from the 1.5 mL tube containing silver extract+ phage cocktail with titer on corresponding bacteria according to QC-SOP-005. Results are presented on FIGS. 6A to 6D. It can be seen notably that the bacteriophages were superior to the silver nanoparticles, and that for some bacteria (FIG. 6B), there was a synergy between the bacteriophages and the silver nanoparticle (Silverlon).

Example 17: In-Vitro Treatment of Wounds:Effect of Film and Ceftazidine Antibiotic on *K. pneumoniae* and on Biofilm Formation 12 mm disks of pig skin were prepared using sterile scissors. Using a sterile scalpel, an incision was created in the middle of each pig skin disk and the disks were placed 12 well plates containing TSA (Trypticase soy agar) (1 mL/well), followed by dispensing 10 µL of bacterial daily culture (ATCC43816 *K. pneumoniae*) at $10^5$ cfu/mL. After 10 min, 4 h and overnight static incubation at 37° C., 5 mm*5 mm piece of the proposed film were added on the incision zone containing bacteria. After 24 h of incubation at 37° C., the pig skin was removed from from the TSA layer and fixed using a solution of HEPES+4% PFA+2.5% Glutaraldehyde for 1 h at room temperature, following by washing 3 times with distilled water and subsequent addition of 30% ethanol and incubation for 30 min at room temperature. Afterwards, the sample was washed 3 times with distilled water. Incubation with ethanol and the associated washes were repeated with increases in ethanol concentration (50%, 70%, 90% and 100%). After the last wash, samples were left to dry for 6 h at room temperature and then placed for several days in the vacuum at room temperature. Samples were coated with gold and scanning electron microscope pictures were obtained. Results are shown in FIGS. 7A to 7F. Superiority of the film in reducing bacterial contamination was clearly seen by the very small number of bacteria covering the skin surface, when compared to an almost continuous carpet of bacteria for control samples and films of bacteria for the antibiotic group.

Example 18: Production of Thin Films

Thin film mixture comprised of PEAU polymer, bacteriophage cocktail, salts, and organic solvent with a solid content of 19.5% is constantly mixed in a stirred tank reactor connected to an assembly line. The thin film blend is metered onto a polymer liner (3M ScotchPak 9741 or other appropriate lidding material) using a liquid handler/polymer coater. Tickness is for example 0.1 mm to 1 mm, or 0.1 mm to 0.55 mm. This can be achieved using comma head coating setup. Coating width can be any suitable width, for example from 80 mm to 550 mm. The lidding film can be either pre-cut or cut at alater stage in the process. Coating speed can vary, for example, between 0.25 m/min to 2 m/min. The wet-blend liner is transferred on the conveyer belt into a series of ovens with temperatures varying from 37.8 to 50° C. in order to evaporate the solvent without affecting the activity of the bacteriophages. A backing lid is placed, and if not pre-cut, the dry-blend is passed through a cutter and a packaging unit.

Example 19: Alternative PEAU Synthesis

In some embodiments, triphosgene is replaced diphenyl carbonate in PEAU synthesis according to the reaction:

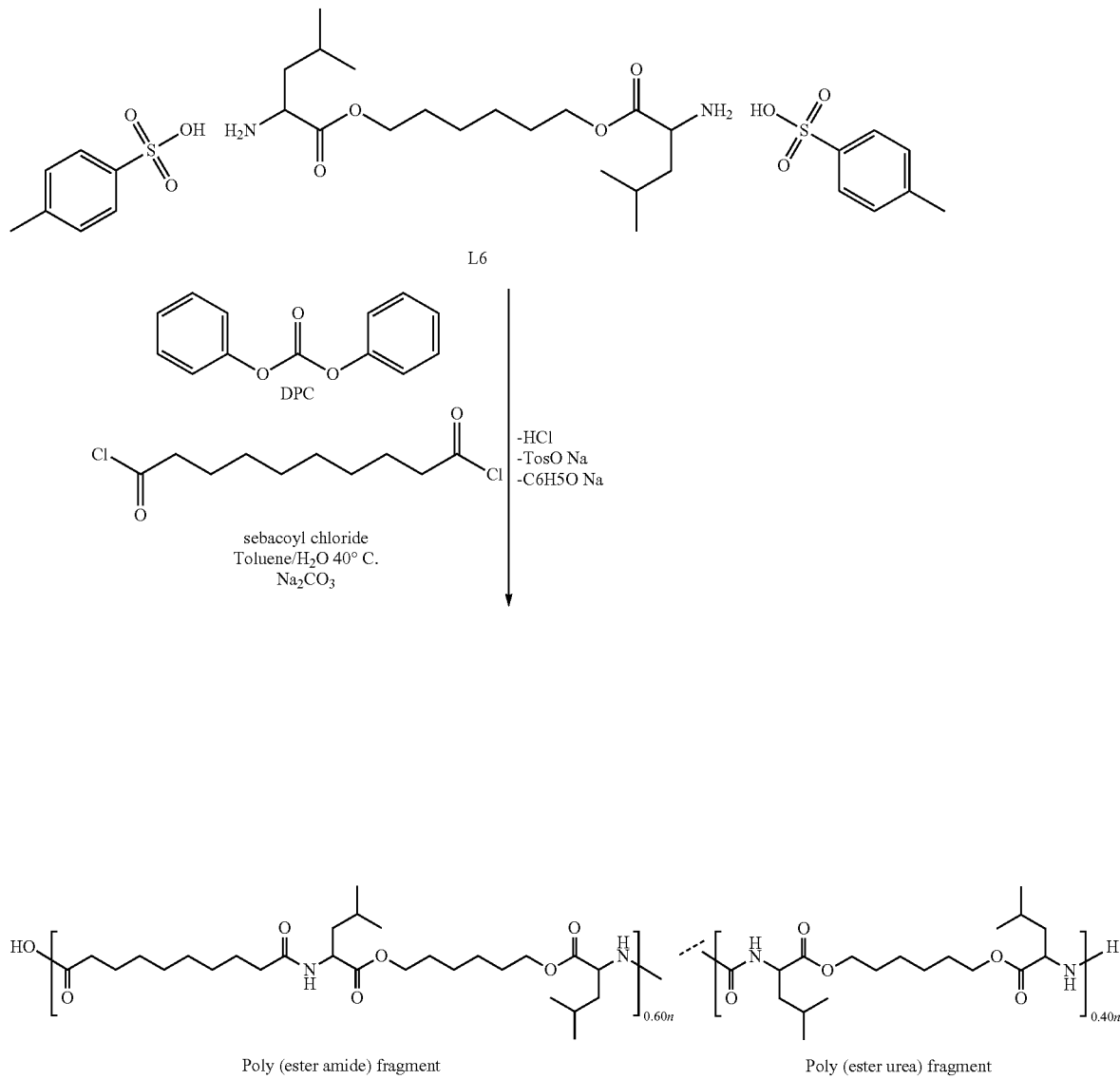

Poly (ester amide) fragment                Poly (ester urea) fragment

Due to the health hazards of using triphosgene (may cause severe skin burns and eye damage, and acute toxicity if inhaled), it is advantageous to replace triphosgene by diphenyl carbonate (DPC), the reaction mixture will then be required to be heated at 40° C. for 20 hours in toluene for the formation of poly ester urea. The change of solvent should not affect the formation of polyester amide, leading to the ultimate formation of poly ester amide urea (PEAU). DPC is less reactive than triphosgene, which reacts with the L6 monomer at room temperature. Therefore, dichloromethane (DCM) should be replaced by another solvent with high boiling point. Toluene with b.p of 111° C. or 2-methyltetrahydrofuran with b.p. of 80° C. could be used as alternatives.

Also, one may replace sebacoyl chloride with sebacid acid:

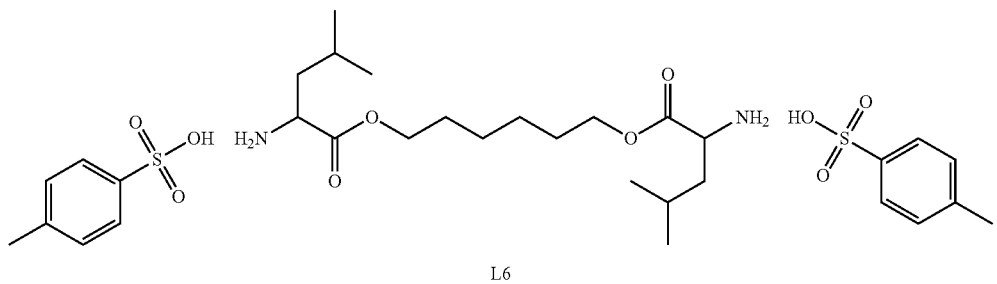

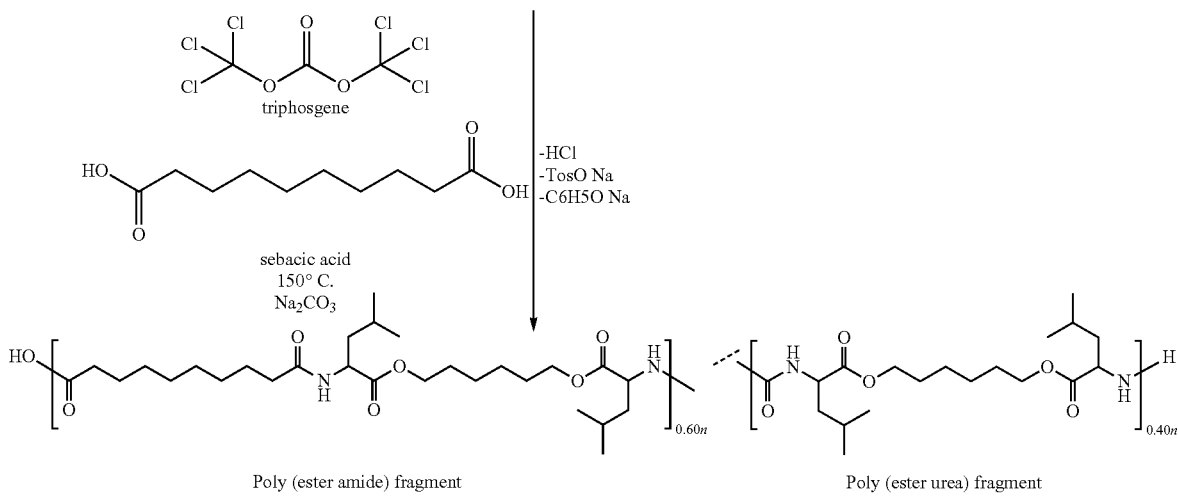

If we use Sebacic Acid instead of Sebacoyl Chloride, the reaction would require much more heat, as this is a dehydration reaction rather than a nucleophilic acyl substitution reaction. The reason that heat is needed when using Sebacic Acid is because the reaction proceeds with an ammonium carboxylate salt intermediate, which requires high temperatures to remove an H₂O group to form an amide. Another option to synthesize the polymer is use sebacic acid instead of sebacoyl chloride and heating the reaction to 150° C. (using DPC or triphosgene), as this is a dehydration reaction rather than a nucleophilic acyl substitution reaction. The reason that heat is needed when using sebacic acid is because the reaction proceeds with an ammonium carboxylate salt intermediate, which requires high temperatures to remove an H₂O to form an amide. In order to avoid heating the reaction at high temperatures, it is to add DCC (N,N'-dicychlohexylcarbodiimide), a coupling agent in the synthesis to enhance the reaction of sebacic acid and L6 monomer.

The reaction then becomes

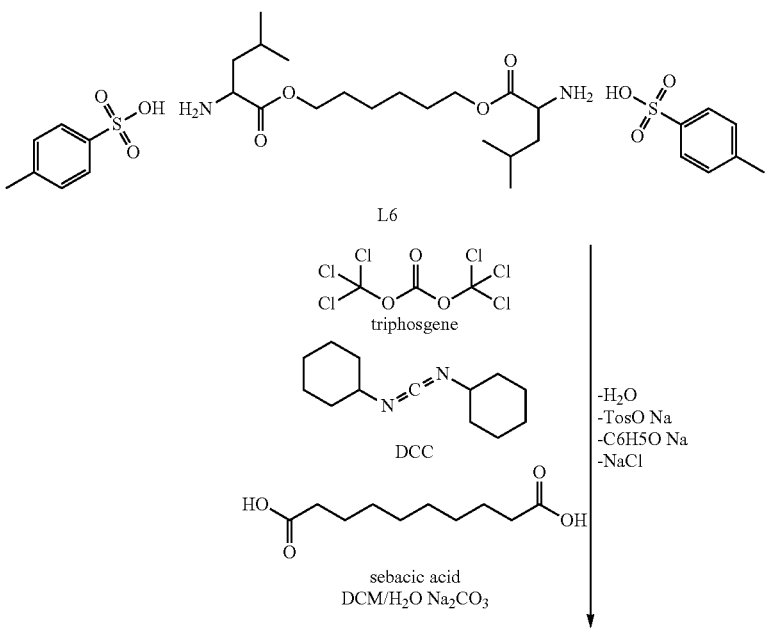

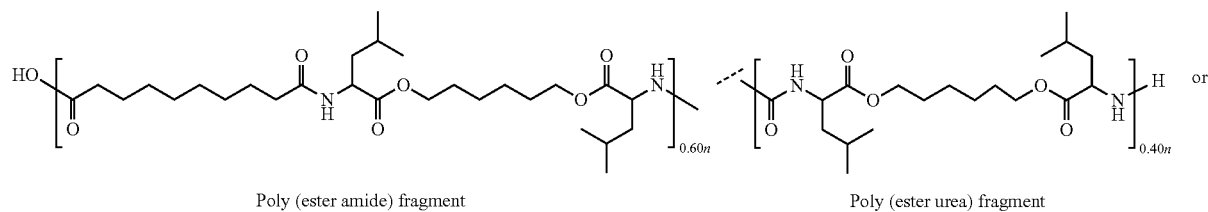

Poly (ester amide) fragment    Poly (ester urea) fragment

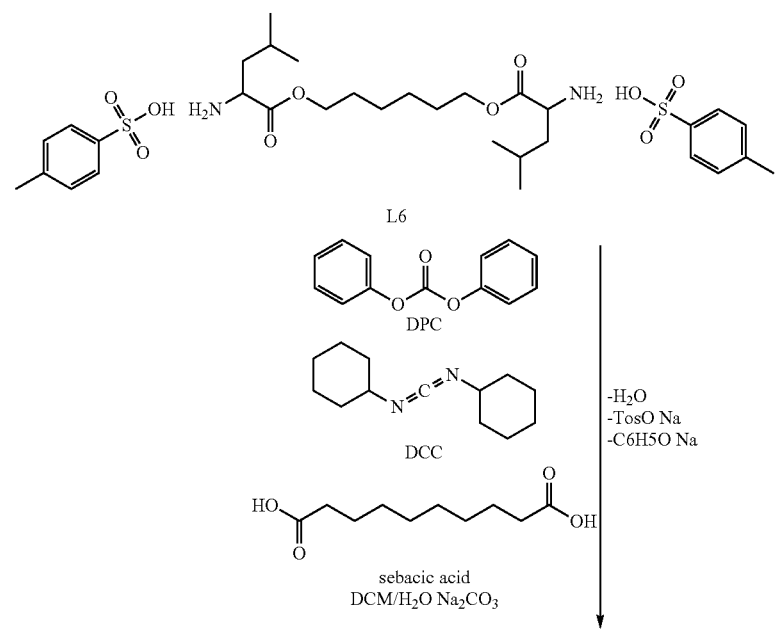

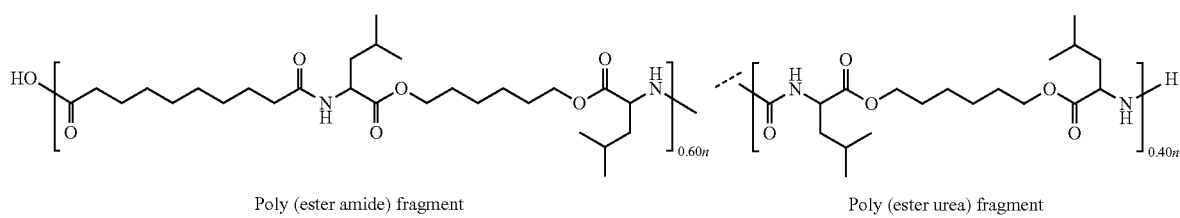

Poly (ester amide) fragment    Poly (ester urea) fragment

Another strategy is to use 1-(3-Dimethylaminopropyl)-3-ethylcarbodiimide hydrochloride, usually known as water soluble carbodiimide, (abbreviated EDCl or EDC), combining with hydroxybenzotriazole (abbreviated HOBt) in one pot synthesis shown in FIG. 2. The advantages of using EDCl and HOBt as coupling agents include enhancement of amide formation, reaction at room temperature and by products of the coupling reaction are readily soluble in water, can be easily removed during the purification process. The reaction then becomes

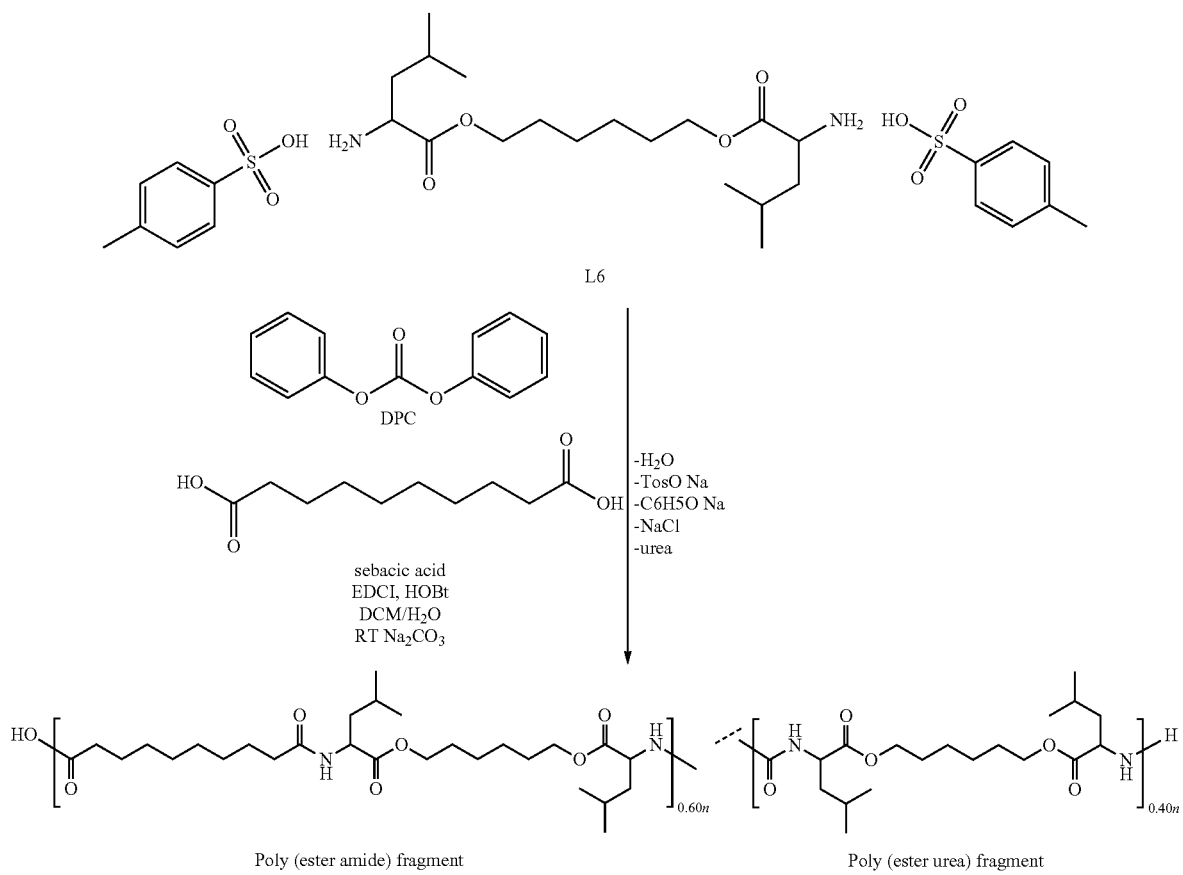

Other Embodiments

The foregoing discussion discloses and describes merely exemplary embodiments of the disclosure. One skilled in the art will readily recognize from such discussion and from the accompanying drawings and claims, that various changes, modifications and variations can be made therein without departing from the spirit and scope of the disclosure as defined in the following embodiments and claims.

1. A polymer selected from
   (1) a poly (ester amide urea) wherein at least one diol, at least one diacid, and at least one amino acid are linked together through an ester bond, an amide bond, and a urea bond,
   (2) a poly (ester urethane urea) wherein at least one diol and at least one amino acid are linked together through an ester bond, a urethane bond, and a urea bond,
   (3) a poly (ester amide urethane urea) wherein at least one diol, at least one diacid, and at least one amino acid are linked together through an ester bond, an amide bond, a urethane bond, and a urea bond,
   (4) a poly (ester amide urethane) wherein at least one diol, at least one diacid, and at least one amino acid are linked together through an ester bond, an amide bond, and a urethane bond,
   (5) a poly (ester urea) wherein at least one diol and at least one amino acid are linked together through an ester bond and a urea bond (in other words, at least one diol, a carbonic acid, and at least one amino acid are linked together through an ester bond and a urea bond), and
   (6) a poly (ester urethane) wherein at least one diol and at least one amino acid are linked together through an ester bond and a urethane bond, further wherein
   the at least one diol is a compound of formula: HO—$R_1$—OH, $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

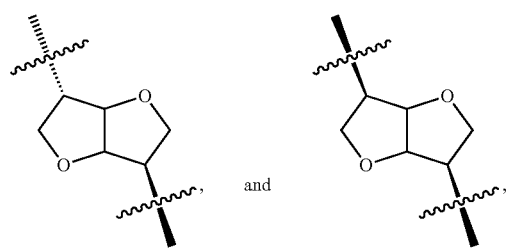

the at least one diacid is a compound of formula:
   HO—(CO)—$R_3$—(CO)—OH,
$R_3$ is $C_1$-$C_{12}$ alkylene,
the at least one amino acid is chosen from a naturally occurring amino acid and non-naturally occurring amino acid.

2. The polymer of embodiment 1, wherein the polymer is selected from
(1) a poly (ester amide urea) wherein at least one diol, at least one diacid, and at least one amino acid are linked together through an ester bond, an amide bond, and a urea bond, (2) a poly (ester urethane urea) wherein at least one diol and at least one amino acid are linked together through an ester bond, a urethane bond, and a urea bond,
(3) a poly (ester amide urethane urea) wherein at least one diol, at least one diacid, and at least one amino acid are linked together through an ester bond, an amide bond, a urethane bond, and a urea bond, and
(4) a poly (ester amide urethane) wherein at least one diol, at least one diacid, and at least one amino acid are linked together through an ester bond, an amide bond, and a urethane bond,
wherein the at least one diol is a compound of formula:

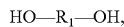

$R_1$ is chosen from $C_2$-$C_{12}$ alkylene optionally interrupted by at least one oxygen, $C_3$-$C_8$ cycloalkylene, $C_3$-$C_{10}$ cycloalkylalkylene,

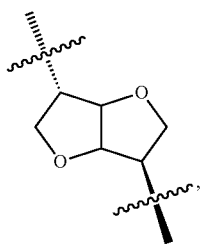 and 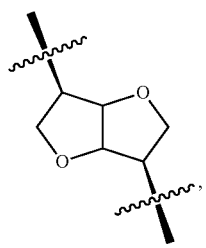

the at least one diacid is a compound of formula:
HO—(CO)—$R_3$—(CO)—OH,
$R_3$ is $C_2$-$C_{12}$ alkylene,
the at least one amino acid is chosen from a naturally occurring amino acid and non-naturally occurring amino acid.

3. The polymer of embodiments 1 or 2, wherein the at least one amino acid is a L- or D-amino acid.

4. The polymer of embodiments 1 or 2, wherein the at least one amino acid is L-glycine, L-alanine, L-valine, L-leucine, L-isoleucine, L-proline, L-methionine, L-phenylalanine, L-tryptophan, or a D isomer thereof.

5. The polymer of embodiments 1 or 2, wherein the polymer is a poly (ester amide urea) comprising the following two blocks with random distribution thereof:

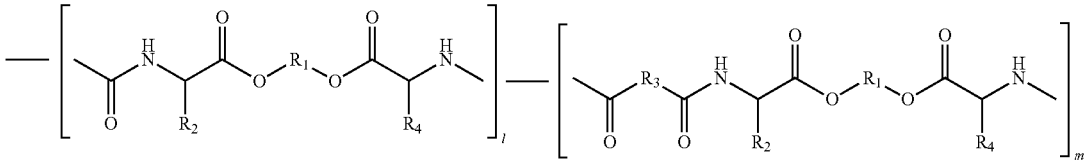

wherein
the ratio of l:m ranges from 0.01:0.99 to 0.99:0.01, l+m=1,
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

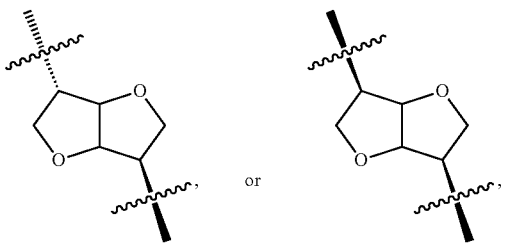

$R_3$ is $C_1$-$C_{12}$ alkylene,
$R_2$ and $R_4$ are independently chosen from the side chains of L- and D-amino acids so that the carbon to which $R_2$ or $R_4$ is attached has L or D chirality.

6. The polymer of embodiments 1 or 2, wherein the polymer is poly (ester urethane urea) comprising the following two blocks with random distribution thereof:

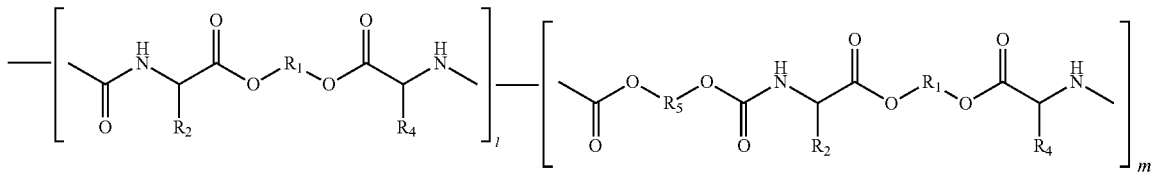

wherein
the ratio of l:m ranges from 0.01:0.99 to 0.99:0.01, l+m=1,
$R_1$ and $R_5$ are independently chosen from $C_1$-$C_{12}$ alkylene optionally interrupted by at least one oxygen, $C_3$-$C_8$ cycloalkylene, $C_3$-$C_1$ cycloalkylalkylene,

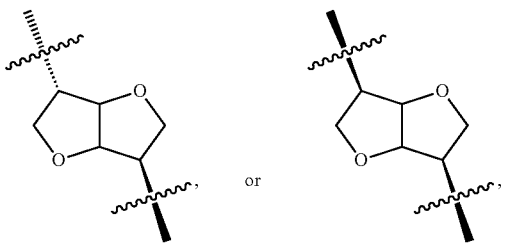

and
R₂ and R₄ are independently chosen from the side chains of L- and D-amino acids so that the carbon to which R₂ or R₄ is attached has L or D chirality.

7. The polymer of embodiments 1 or 2, wherein the polymer is poly (ester amide urethane urea) comprising the following three blocks with random distribution thereof:

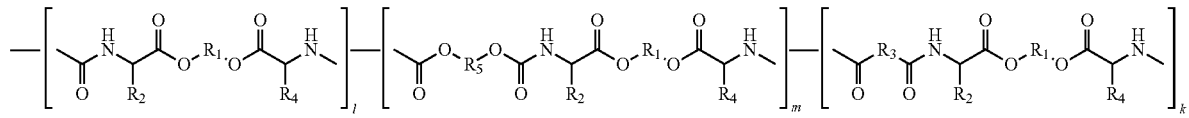

wherein
the ratio of l:m:k ranges from 0.05:0.05:0.90 to 0.90:0.05:0.05, l+m+k=1, $R_1$ and $R_5$ are independently chosen from $C_1$-$C_{12}$ alkylene optionally interrupted by at least one oxygen, $C_3$-$C_8$ cycloalkylene, $C_3$-$C_{10}$ cycloalkylalkylene,

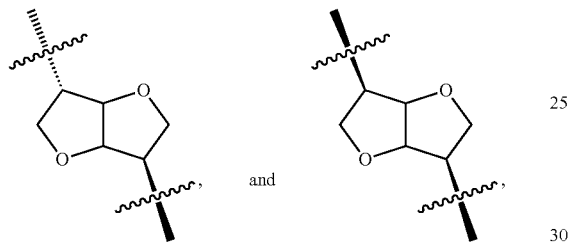

$R_3$ is $C_1$-$C_{12}$ alkylene, and
R₂ and R₄ are independently chosen from the side chains of L- and D-amino acids so that the carbon to which R₂ or R₄ is attached has L or D chirality.

8. The polymer of embodiments 1 or 2, wherein the polymer is (ester amide urethane) comprising the following two blocks with random distribution thereof:

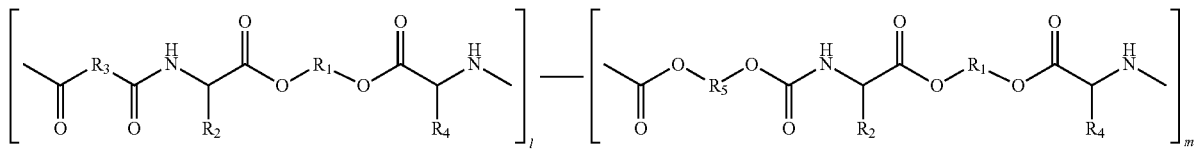

wherein
the ratio of l:m ranges from 0.01:0.99 to 0.99:0.01, l+m=1, $R_1$ and $R_5$ are independently chosen from $C_1$-$C_{12}$ alkylene optionally interrupted by at least one oxygen, $C_3$-$C_8$ cycloalkylene, $C_3$-$C_1$ cycloalkylalkylene,

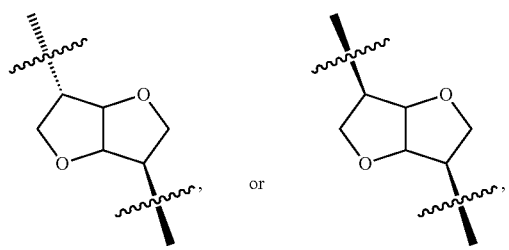

$R_3$ is $C_1$-$C_{12}$ alkylene, and
R₂ and R₄ are the same and selected from the side chains of L- and D-amino acids so that the carbon to which R₂ or R₄ is attached has L or D chirality.

9. The polymer of any one of embodiments 1-8, wherein $R_1$ is —$(CH_2)_6$—.

10. The polymer of any one of embodiments 1, 2, 5, 7, and 8, wherein $R_3$ is —$(CH_2)_8$—.

11. The polymer of any one of embodiments 5-8, wherein both R₂ and R₄ are the side chain of L-leucine.

12. The polymer of embodiment 5, wherein $R_1$ is —$(CH_2)_6$—, $R_3$ is —$(CH_2)_8$—, and both R₂ and R₄ are the side chain of L-leucine.

13. The polymer of embodiment 12, wherein l is 0.6 and m is 0.4.

14. A polymer blend comprising a first polymer and a second polymer, the first polymer being a polymer of any one of embodiments 1-13, and the second polymer being selected from a polymer of any one of embodiments 1-13 and a poly (ester amide) wherein at least one diol, at least one diacid and at least one amino acid are linked together through an ester bond and an amide bond and wherein the at least one diol, at least one diacid, and at least one amino acid are as defined in embodiment 1, and further wherein the first and second polymers are not the same polymer.

15. The polymer blend of embodiment 14, wherein the second polymer is a poly (ester amide) in which at least one diol, at least one diacid, and at least one amino acid are as defined in embodiment 1.

16. The polymer blend of embodiment 14 or 15, wherein the ratio of the first polymer to the second polymer ranges from 0.01:0.99 to 0.99:0.01.

17. The polymer blend of embodiment 14 or 15, wherein the ratio of the first polymer to the second polymer ranges from 0.05:0.95 to 0.95:0.05.

18. The polymer blend of any one of embodiments 14 or 15, wherein the ratio of the first polymer to the second polymer ranges from 0.30:0.70 to 0.70:0.30.

19. The polymer blend of any one of embodiments 14-18, wherein the first polymer is a poly (ester urea) and the second polymer is a poly(ester amide).

20. The polymer blend of embodiment 19, wherein the poly(ester amide) is composed of L-leucine, 1,6-hexanediol, and sebacic acid and the poly(ester urea) is composed of L-leucine, 1,6-hexanediol, and carbonic acid.

21. The polymer blend of embodiment 19, wherein the poly(ester urea) comprises repeating units of:

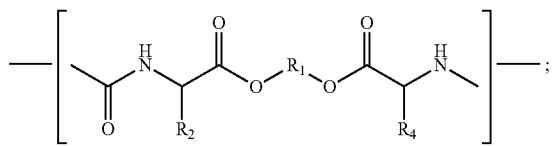

and the poly(ester amide) comprises repeating units of:

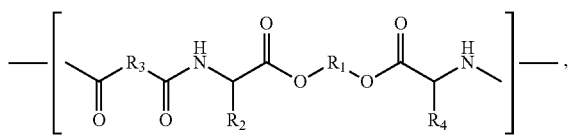

wherein $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

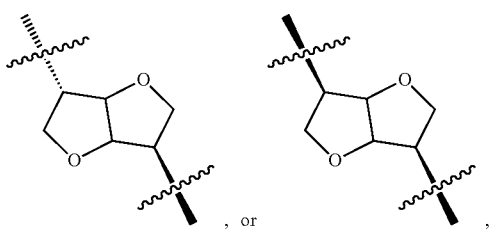

$R_3$ is C $C_{12}$ alkylene,
$R_2$ and $R_4$ are independently chosen from the side chains of L- and D-amino acids so that the carbon to which $R_2$ or $R_4$ is attached has L or D chirality.

22. The polymer blend of any one of embodiments 14-21, wherein the ratio of the first polymer to the second polymer is 0.4:0.6.

23. A composition comprising a polymer of any one of embodiments 1-13 or a polymer blend of any one of embodiments 14-22 and at least one bioactive agent.

24. The composition of embodiment 23, further comprising at least one filler.

25. The composition of embodiment 24, wherein the at least one filler includes at least one of an inorganic salt, sucrose, gelatin, or a buffer.

26. The composition of embodiments 23 or 24, wherein the at least one filler includes at least one of calcium salts, magnesium salts, or mixtures thereof.

27. The composition of any one of embodiments 23-26, wherein the at least one filler is a mixture of calcium carbonate and magnesium carbonate.

28. The composition of embodiment 24, wherein the at least one filler includes TMN buffer.

29. The composition of any one of embodiments 23-28, wherein the at least one bioactive agent is chosen from an antiseptic, an anti-infective, bacteriophage, a bacteriophage-derived product, endolysins, a phage protein, a phage enzyme, an antibiotic, an antibacterial, an antiprotozoal agent, an antiviral, an analgesic, an anti-inflammatory agent, a steroid, a non-steroidal anti-inflammatory agent, Prednisolone, Voltaren, a COX-2 inhibitor, an antineoplastic agent, a contraceptive, a central nervous system (CNS) active drug, an hormone, a vaccine, and mixtures thereof.

30. The composition of any one of embodiments 23-29, comprising at least one of calcium gluconate, a phage stabilizing additive, hyaluronidase, fibrinolysin, a fibrinolytic enzyme, methyluracyl, a metabolic process stimulating agent, sodium hydrocarbonate, L-arginine, a vasodilator, mono- and disaccharides, polysaccharides and mucopolysaccharides, metronidazole, an anti-protozoa drug, clotrimazolum, an anti-fungal drug, thrombin, a hemostatic, a vitamin, or mixtures thereof.

31. The composition of any one of embodiments 23-30, wherein the at least one bioactive agent includes at least one bacteriophage.

32. The composition of any one of embodiments 23-31, wherein the at least one bioactive agent includes a bacteriophage-derived product selected from endolysins, EPS depolymerases, depolymerases, hydrolases, lyases, phage enzymes, phage early proteins, phage holins, and mixtures thereof.

33. The composition of any one of embodiments 23-32, wherein the at least one bioactive agent includes at least one pain reliever.

34. The composition of embodiment 33, wherein the at least one pain reliever is chosen from benzocaine, lidocaine, tetracaine, pramocaine, dibucaine, and mixtures thereof.

35. The composition of any one of embodiments 23-34, wherein the at least one bioactive agent includes at least one antibiotic.

36. The composition of embodiment 35, wherein the at least one antibiotic is chosen from tetracycline, ciprofloxacin, levofloxacin, mupirocin, neomycin, erythromycin, bacitracin, polymyxin, chlorohexidine, mafenide acetate, silver sulfadiazine, silver nitrate, and mixtures thereof.

37. The composition of embodiment 35 or 36, wherein the at least one bioactive agent further includes at least one bacteriophage.

38. The composition of embodiment 37, wherein the at least one bioactive agent further includes at least one pain reliever.

39. The composition of any one of embodiments 23-38, wherein the at least one bioactive agent includes at least one enzyme.

40. The composition of embodiment 39, wherein the at least one enzyme is chosen from papain, collagenase, chymotrypsin, trypsin, elastase, fibrinolysin, hyaluronidase, alpha-chymotrypsin, and mixtures thereof.

41. The composition of any one of embodiments 23-40, wherein the at least one bioactive agent includes at least one anti-bacterial agent.

42. The composition of any one of embodiments 23-40, wherein the at least one bioactive agent includes at least one anti-viral agent.

43. The composition of embodiment 23, comprising a poly (ester amide urea), at least one bacteriophage, calcium carbonate, magnesium carbonate, benzocaine, ciprofloxacin, and chymotrypsin.

44. The composition of any one of embodiments 23-43, wherein the composition is in the form of a non-woven porous material.

45. The composition of embodiment 44, wherein the non-woven porous material is prepared by:
 a. mixing a polymer of any one of embodiments 1-13 or a polymer blend of any one of embodiments 14-22 in a mixture comprising at least one salt and an organic solvent;
 b. casting the resulting mixture from step a onto a hydrophobic surface;
 c. evaporating the organic solvent to obtain a film; and
 d. leaching the at least one salt from the film.

46. The composition of any one of embodiments 23-43, wherein the composition is in the form of perforated film.

47. The composition of any one of embodiments 23-43, wherein the composition is in the form of a film.

48. The composition of any one of embodiments 23-43, wherein the composition is in the form of a spray.

49. The composition of any one of embodiments 23-43, wherein the composition is in the form of an unperforated film.

50. The composition of any one of embodiments 23-43, wherein the composition is in the form of a gel.

51. The composition of any one of embodiments 23-43, wherein the composition is in the form of an hydrogel.

52. The composition of any one of embodiments 23-43, wherein the composition is in the form of an ointment.

53. A composition comprising at least one bacteriophage and at least one salt.

54. The composition of embodiment 53, wherein the at least one salt is inorganic.

55. The composition of embodiment 53 or 54, wherein the at least one salt is chosen from calcium salts, magnesium salts, strontium salts, and barium salts.

56. The composition of any one of embodiments 53-55, wherein the at least one salt is chosen from calcium salts and magnesium salts.

57. The composition of any one of embodiments 53-56, wherein the at least one salt is chosen from calcium carbonate, calcium phosphate, and magnesium carbonate.

58. The composition of any one of embodiments 53-57, wherein the at least one salt is a mixture of calcium carbonate and magnesium carbonate.

59. The composition of any one of embodiments 53-58, wherein the at least one salt is a mixture of calcium carbonate and magnesium carbonate and the weight ratio of $MgCO_3$ to $CaCO_3$ is 5:95.

60. The composition of any one of embodiments 53-59, wherein the composition is in the form of a dry powder.

61. A composition comprising at least one bacteriophage and at least one buffer, wherein the composition is in the form of a dry powder.

62. The composition of embodiment 61, wherein the buffer is TMN (Tris-$MgCl_2$—NaCl) buffer.

63. A wound dressing comprising the composition of any one of embodiments 23-62.

64. An implantable surgical device comprising the composition of any one of embodiments 23-62.

65. A food or animal feed additive comprising the composition of any one of embodiments 23-62.

66. A method for treating agricultural crops, comprising administering the composition of any one of embodiments 23-62 on the agricultural crops.

67. A method of treating a patient having a wound in need thereof comprising inserting into the wound or covering the wound with a composition of any one of embodiments 23-62.

68. The method of embodiment 67, wherein the wound is a superficial wound.

69. The method of embodiment 67, wherein the wound is an ulcerative wound.

70. The method of embodiment 67 or 69, wherein the wound is a deep wound.

71. The method of any one of embodiments 67-70, wherein the wound is open or infected.

72. The method of any one of embodiments 67-71, wherein the wound is treated prophylactically before any infection is detected.

73. The method of any one of embodiments 67-72, wherein the composition also comprises at least one bacteriophage lytic for bacteria found in the wound.

74. The method of any one of embodiments 67-73, wherein the composition also comprises an enzyme capable of hydrolytically cleaving the polymer.

75. A process for preparing the composition of embodiment 61, comprising: mixing at least one bacteriophage and at least one buffer, and drying the mixture through vacuum drying, freeze drying, lyophilization, or spray-drying.

76. The process of embodiment 75, wherein the mixture is dried through freeze-drying.

77. A process for preparing the composition of embodiment 53, comprising
 mixing and holding (incubating) the at least one salt and at least one bacteriophage,
 filtrating the obtained suspension to obtain the at least one bacteriophage adsorbed (immobilized) wet solid product,
 washing the obtained wet solid product with saline solution optionally; and
 drying the obtained wet solid product through vacuum drying, freeze drying, lyophilization, or spray-drying.

78. A process for preparing the composition of embodiment 31, comprising:
 a. mixing the composition of embodiment 53 or 61 with a mixture comprising an organic solvent and a polymer of any one of embodiments 1-13 or a polymer blend of any one of embodiments 14-21; optionally adding at least one other bioactive agent;
 b. casting the resulting mixture from step a onto a hydrophobic surface; and
 c. removing the organic solvent to obtain a film.

79. The process of embodiment 78, wherein removing the organic solvent includes evaporating the organic solvent.

80. A process for preparing the composition of embodiment 23, comprising:
 a. mixing the at least one bioactive agent with a mixture comprising an organic solvent and a polymer of any one of embodiments 1-13 or a polymer blend of any one of embodiments 14-21;

b. casting the resulting mixture from step a onto a hydrophobic surface; and
c. removing the organic solvent to obtain a film.

81. A process for preparing the salt of a diester,

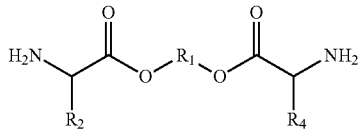

comprising:
heating a mixture comprising

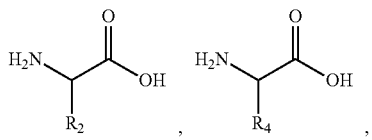

HO—$R_1$—OH, at least one acid that is not an amino acid, and cyclohexane,
wherein
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

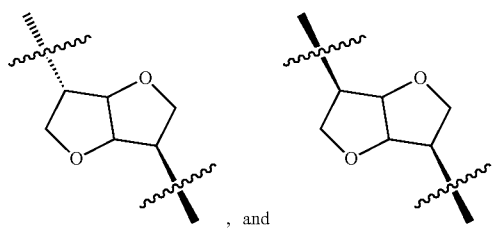

$R_2$ and $R_4$ are independently chosen from the side chains of L- and D-amino acids such that the carbon to which $R_2$ or $R_4$ is attached has L or D chirality;
and the at least one acid that is not an amino acid is chosen from inorganic and organic acids such as sulfonic, sulfuric, and hydrochloric acids.

82. The process of embodiment 81, wherein $R_2$ and $R_4$ are both the side chain of L-leucine.

83. The process of embodiment 81 or 82, wherein $R_1$ is —$(CH_2)_6$—.

84. The process of any one of embodiments 81-83, wherein the at least one acid is p-toluenesulfonic acid.

85. A process for preparing the polymer of any one of embodiments 1-13, comprising
a. mixing a salt of the diester and at least one base in water,
b. mixing at least two bis-electrophiles in an organic solvent,
c. mixing the mixtures from step a and b and stirring vigorously,
d. obtaining the organic layer,
wherein the at least two bis-electrophiles is
a mixture of diacid chloride of formula Cl(CO)—$R_3$—(CO)Cl and tri-phosgene with molar ratio of the diacid chloride:triphosgene ranges from 0.95:(0.05/3) to 0.05:(0.95/3) for preparing poly(ester amide urea), or a mixture of dichloroformate of formula Cl(CO)—O—$R_5$—O—(CO)Cl and triphosgene with molar ratio of the dichloroformate:triphosgene ranging from 0.95:(0.05/3) to 0.05:(0.95/3) for preparing poly(ester urethane urea), or a mixture of diacid chloride of formula Cl(CO)—$R_3$—(CO)Cl, di-chloroformate of formula Cl(CO)—O—$R_5$—O—(CO)Cl, and tri-phosgene with molar ratio of the diacid chloride:dichloroformate:triphosgene ranging from 0.90:0.05:(0.05/3) to 0.05:0.05:(0.90/3) for preparing poly(ester amide urethane urea), or a mixture of diacid chloride of formula Cl(CO)—$R_3$—(CO)Cl and di-chloroformate of formula Cl(CO)—O—$R_5$—O—(CO)Cl with molar ratio of the diacid chloride:di-chloroformate ranging from 0.95:0.05 to 0.05:0.95 for preparing poly(ester amide urethane), the diester has the following formula

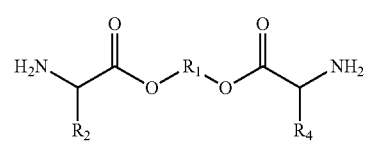

wherein
$R_1$ and $R_5$ are independently chosen from $C_1$-$C_{12}$ alkylene optionally interrupted by at least one oxygen, $C_3$-$C_8$ cycloalkylene, $C_3$-$C_{10}$ cycloalkylalkylene,

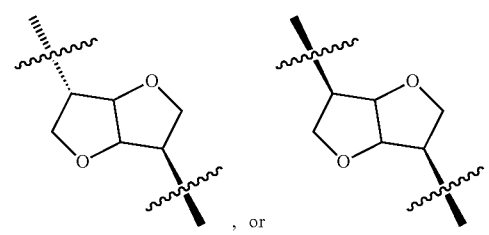

$R_3$ is $C_1$-$C_{12}$ alkylene, and
$R_2$ and $R_4$ are the same and selected from the side chains of L- and D-amino acids so that the carbon to which $R_2$ or $R_4$ is attached has L or D chirality.

86. A process for preparing a poly (ester amide urea) comprising:
a. mixing triphosgene, diacid HO(CO)—$R_3$—(CO)OH, and at least one organic base in an organic solvent, wherein $R_3$ is $C_1$-$C_{12}$ alkylene,
b. mixing a salt of the diester and at least one base in water,
c. mixing the mixtures from step a and b and stirring vigorously, and
d. obtaining an organic layer,
wherein the diester has the following formula:

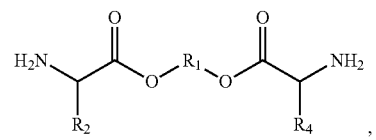

wherein $R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

[structures], and [structure];

$R_3$ is $C_1$-$C_{12}$ alkylene; and
$R_2$ and $R_4$ are independently chosen from the side chains of L- and D-amino acids such that the carbon to which $R_2$ or $R_4$ is attached has L or D chirality.

87. A process for preparing a poly (ester urethane urea) comprising
  a. mixing triphosgene, diol HO—$R_5$—OH, and at least one organic base in an organic solvent,
  b. mixing a salt of the diester and at least one base in water,
  c. mixing the mixtures from step a and b and stirring vigorously, and
  d. obtaining an organic layer, wherein
the diester has the following formula:

[structure: H$_2$N–CR$_2$H–C(O)–O–R$_1$–O–C(O)–CR$_4$H–NH$_2$]

wherein
$R_1$ and $R_5$ are independently chosen from $C_1$-$C_{12}$ alkylene optionally interrupted by at least one oxygen, $C_3$-$C_8$ cycloalkylene, $C_3$-$C_1$ cycloalkylalkylene,

[structures], and [structure];

and
$R_2$ and $R_4$ are independently chosen from the side chains of L- and D-amino acids such that the carbon to which $R_2$ or $R_4$ is attached has L or D chirality.

88. A process for preparing a poly(ester urea) comprising
  a. mixing a salt of the diester and at least one base in water,
  b. mixing triphosgene in an organic solvent,
  c. mixing the mixtures from step a and b and stirring vigorously, and
  d. obtaining an organic layer including the poly (ester urea), wherein
the diester has the following formula:

[structure: H$_2$N–CR$_2$H–C(O)–O–R$_1$–O–C(O)–CR$_4$H–NH$_2$]

wherein
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

[structures], and [structure];

and
$R_2$ and $R_4$ are independently chosen from the side chains of L- and D-amino acids such that the carbon to which $R_2$ or $R_4$ is attached has L or D chirality.

89. The process of any one of embodiments 86-88, wherein the salt of the diester is a p-toluenesulfonic acid salt of bis-(L-leucine)-1,6-hexylene diester.

90. The process of any one of embodiments 86-89, wherein the at least one base is an inorganic base.

91. The process of any one of embodiments 86-90, wherein the at least one base is sodium carbonate.

92. The process of any one of embodiments 86-91, wherein the organic solvent is chloroform, dichloromethane, or ethyl acetate.

93. The process of any one of embodiments 86-92, wherein the salt of the diester is prepared by the process of embodiment 81.

The invention claimed is:

1. A method of treating, reducing or preventing bacterial infection in a wound, the method comprising: applying a flexible film on the wound, the film including a biodegradable polymer with bacteriophages dispersed therein, wherein the polymer is a poly (ester amide urea) comprising the following two blocks with random distribution thereof:

[polymer structure block 1 with subscript $l$]

[polymer structure block 2 with subscript $m$]

wherein
the ratio of l:m ranges from 0.01:0.99 to 0.99:0.01, l+m=1,
$R_1$ is chosen from $C_1$-$C_{12}$ alkylene optionally interrupted by at least one oxygen, $C_3$-$C_8$ cycloalkylene, $C_3$-$C_{10}$ cycloalkylalkylene,

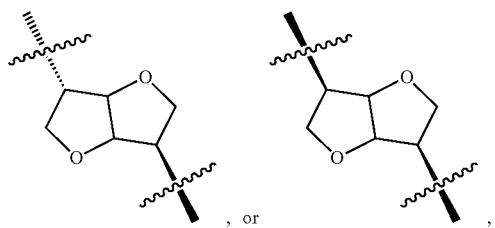
, or , $R_3$ is C1-C12 alkylene,
$R_2$ and $R_4$ are independently chosen from the side chains of L- and D-amino acids so that the carbon to which $R_2$ or $R_4$ is attached has L or D chirality;
further comprising delivering a fraction of the bacteriophages in the wound within a rapid delivery period immediately after applying the film, the rapid delivery period being smaller than 4 hours, and afterwards releasing at least part of the remaining bacteriophages in the wound at a rate smaller than within the rapid delivery period.

2. The method of claim 1, wherein $R_1$ is —(CH2)$_6$—, $R_3$ is —(CH2)$_8$—, and both $R_2$ and $R_4$ are the side chain of L-leucine.

3. The method as defined in claim 1, wherein the film further includes salt particles dispersed in the polymer.

4. The method as defined in claim 3, wherein at least part of the bacteriophages is adsorbed on the salt particles.

5. The method as defined in claim 4, wherein the salt particles include $CaCO_3$ particles.

6. The method as defined in claim 1, wherein the film further includes a buffer.

7. The method as defined in claim 6, wherein the buffer is TMN (Tris-$MgCl_2$—NaCl) buffer.

8. The method as defined in claim 1, wherein the film further includes at least one of silversulfadiazine, silver nitrate and nanocrystalline silver.

9. The method as defined in claim 1, wherein the film further includes an antibiotic.

10. The method as defined in claim 1, where the film is applied for a duration of between 1 day and 20 days.

11. The method as defined in claim 10, wherein the film is applied for a duration of between 3 and 7 days.

12. The method as defined in claim 10, wherein the film is a first film, the method further comprising removing the first film after the duration and applying a second film including the biodegradable polymer with the bacteriophages dispersed therein on the wound.

13. The method as defined in claim 1, wherein the film includes an enzyme operative to degrade the film.

14. The method as defined in claim 13, wherein the enzyme is selected from elastase and a metalloproteinase.

15. The method as defined in claim 1, wherein the bacteriophages are present in the film at 500,000 PFU/cm$^2$ or more.

16. The method as defined in claim 1, wherein the film is non-woven and non-porous.

17. The method as defined in claim 1, wherein the film is between 100 μm and 1000 μm thick.

18. The method as defined in claim 1, wherein the wound is a pressure ulcer.

19. The method as defined in claim 1, wherein the wound is a burn wound.

20. The method as defined in claim 1, wherein a bactericide is applied to the wound before the film is applied.

21. The method as defined in claim 20, wherein the bactericide includes at least one of an antibiotic, silversulfadiazine, silver nitrate and nanocrystalline silver.

22. The method as defined in claim 1, wherein the wound contains at least one of antibiotic-resistant and silver-resistant bacteria, the bacteriophage being specific to the at least one of antibiotic-resistant and silver-resistant bacteria.

23. The method as defined in claim 1, wherein the film is substantially transparent when wet.

24. The method as defined in claim 1, wherein the film is a dry solid film.

25. The method as defined in claim 1, wherein the method is for preventing bacterial infection in the wound.

26. The method as defined in claim 1, wherein the method is for treating bacterial infection in the wound.

27. A method of treating, reducing or preventing bacterial infection in a wound, the method comprising: applying a flexible film on the wound, the film including bacteriophages dispersed in a biodegradable polymer, wherein the polymer is selected from
(1) a poly (ester amide urea) wherein at least one diol, at least one diacid, and at least one amino acid are linked together through an ester bond, an amide bond, and a urea bond,
(2) a poly (ester urethane urea) wherein at least one diol and at least one amino acid are linked together through an ester bond, a urethane bond, and a urea bond,
(3) a poly (ester amide urethane urea) wherein at least one diol, at least one diacid, and at least one amino acid are linked together through an ester bond, an amide bond, a urethane bond, and a urea bond,
(4) a poly (ester amide urethane) wherein at least one diol, at least one diacid, and at least one amino acid are linked together through an ester bond, an amide bond, and a urethane bond,
(5) a poly (ester urea) wherein at least one diol and at least one amino acid are linked together through an ester bond and a urea bond, and
(6) a poly (ester urethane) wherein at least one diol and at least one amino acid are linked together through an ester bond and a urethane bond,
further wherein
the at least one diol is a compound of formula:
HO—$R_1$—OH, $R_1$ is chosen from $C_1$-$C_{12}$ alkylene optionally interrupted by at least one
oxygen, $C_3$-$C_8$ cycloalkylene, $C_3$-$C_{10}$ cycloalkylalkylene,

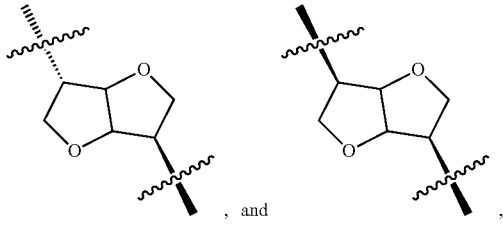
, and , the at least one diacid is a compound of formula:
HO—(CO)—$R_3$—(CO)—OH, $R_3$ is $C_1$-$C_{12}$ alkylene,
   the at least one amino acid is chosen from a naturally occurring amino acid and non-naturally occurring amino acid;
further comprising delivering a fraction of the bacteriophages in the wound within a rapid delivery period immediately after applying the film, the rapid delivery period being smaller than 4 hours, and afterwards releasing at least part of the remaining bacteriophages in the wound at a rate smaller than within the rapid delivery period.

* * * * *